US007794979B2

(12) United States Patent
Cheng et al.

(10) Patent No.: US 7,794,979 B2
(45) Date of Patent: Sep. 14, 2010

(54) SOLUBILITY TAGS FOR THE EXPRESSION AND PURIFICATION OF BIOACTIVE PEPTIDES

(75) Inventors: Qiong Cheng, Wilmington, DE (US); Linda Jane Decarolis, Wilmington, DE (US); Stephen R. Fahnestock, Wilmington, DE (US); Tanja Maria Gruber, Media, PA (US); Lisa Diane Reiss, Wilmington, DE (US); Pierre E. Rouviere, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/692,665

(22) Filed: Jan. 25, 2010

(65) Prior Publication Data
US 2010/0136621 A1 Jun. 3, 2010

Related U.S. Application Data

(62) Division of application No. 11/782,836, filed on Jul. 25, 2007, now Pat. No. 7,678,883.

(51) Int. Cl.
C12P 21/06 (2006.01)
C07H 21/04 (2006.01)
(52) U.S. Cl. .................. 435/69.1; 435/71.1; 435/320.1; 435/252.3; 536/23.4
(58) Field of Classification Search .................. None
See application file for complete search history.

(56) References Cited

U.S. PATENT DOCUMENTS

| | | | |
|---|---|---|---|
| 5,206,154 A | 4/1993 | Lai et al. | |
| 5,215,896 A | 6/1993 | Keck et al. | |
| 5,223,409 A | 6/1993 | Ladner et al. | |
| 5,302,526 A | 4/1994 | Keck et al. | |
| 5,330,902 A | 7/1994 | Keck et al. | |
| 5,403,484 A | 4/1995 | Lander et al. | |
| 5,449,754 A | 9/1995 | Nishioka | |
| 5,480,971 A | 1/1996 | Houghten et al. | |
| 5,571,698 A | 11/1996 | Ladner et al. | |
| 5,585,275 A | 12/1996 | Hudson et al. | |
| 5,639,603 A | 6/1997 | Dower et al. | |
| 5,643,768 A | 7/1997 | Kawasaki | |
| 5,648,244 A | 7/1997 | Kuliopulos et al. | |
| 5,658,754 A | 8/1997 | Kawasaki | |
| 5,837,500 A | 11/1998 | Ladner et al. | |
| 6,037,145 A | 3/2000 | Yabuta et al. | |
| 6,207,446 B1 | 3/2001 | Szostak et al. | |
| 6,214,553 B1 | 4/2001 | Szostak et al. | |
| 6,242,219 B1 | 6/2001 | Better et al. | |
| 6,258,558 B1 | 7/2001 | Szostak et al. | |
| 6,261,804 B1 | 7/2001 | Szostak et al. | |
| 6,281,344 B1 | 8/2001 | Szostak et al. | |
| 6,312,927 B1 | 11/2001 | Hammond | |
| 6,416,950 B1 | 7/2002 | Lohse et al. | |
| 6,429,300 B1 | 8/2002 | Lurz et al. | |
| 6,436,665 B1 | 8/2002 | Kuimelis | |
| 6,518,018 B1 | 2/2003 | Szostak et al. | |
| 6,602,685 B1 | 8/2003 | Lohse | |
| 6,613,548 B1 | 9/2003 | Chu | |
| 6,620,419 B1 | 9/2003 | Lintner | |
| 6,846,655 B1 | 1/2005 | Wagner et al. | |
| 7,074,557 B2 | 7/2006 | Osbourn et al. | |
| 7,078,197 B2 | 7/2006 | Lurz et al. | |
| 2003/0152976 A1 | 8/2003 | Janssen et al. | |
| 2003/0185870 A1 | 10/2003 | Grinstaff et al. | |
| 2005/0221444 A1 | 10/2005 | Williams et al. | |

FOREIGN PATENT DOCUMENTS

| | | | |
|---|---|---|---|
| WO | WO 94/04688 A2 | | 3/1994 |
| WO | 03/006494 | * | 1/2003 |
| WO | 2004/007532 | * | 1/2004 |

OTHER PUBLICATIONS

U.S. Appl. No. 10/935,642, filed Sep. 7, 2004, Xueying Huang.
U.S. Appl. No. 10/935,254, filed Sep. 4, 2004, John P. O'Brien et al.
U.S. Appl. No. 11/641,936, filed Dec. 19, 2006, Linda Jane Decarolis et al.
U.S. Appl. No. 11/641,273, filed Dec. 19, 2006, Linda Jane Decarolis et al.
U.S. Appl. No. 11/516,362, filed Sep. 5, 2006, Linda Jane Decarolis et al.
D.J. Kemp, Direct Immunoassay for Detecting *Escherichia coli* Colonies That Contain Polypeptides Encoded by Cloned DNA Segments, Proc. Natl. Acad. Sci., 1981, vol. 78:4520-4524.
Chien et al., The Two-Hybrid System: A Method to Identify and Clone Genes for Proteins That Interact With a Protein of Interest, Proc. Natl. Acad. Sci., 1991, vol. 88:9578-9582.
Dykes et al., Expression of Atrial Natriuretic Factor as a Cleavable Fusion Protein With Chloramphenicol Acetyltransferase in *Escherichia coli*, Eur. J. Biochem., 1988, vol. 174:411-416.
Schellenberger et al., Peptide Production by a Combination of Gene Expression, Chemical Synthesis, and Protease-Catalyzed Conversion, Int. J. Peptide Protein Res., 1993, vol. 41:326-332.
Shen et al., Multiple Joined Genes Prevent Product Degradation in *Escherichia coli*, Proc. Natl. Acad. Sci., 1984, vol. 281:4627-4631.
Kempe et al., Multiple-Copy Genes: Production and Modification of Monomeric Peptides From Large Multimeric Fusion Proteins, Gene, 1985, vol. 39:239.
Ray et al., Production of Recombinant Salmon Calcitonin by In Vitro Amidation of an *Escherichia coli* Produced Precursor Peptide, Bio/Technology, 1993, vol. 11:64-70.

(Continued)

Primary Examiner—Patricia A Duffy

(57) ABSTRACT

Peptide tags, referred to here as inclusion body tags, are disclosed useful for the generation of insoluble fusion peptides. The fusion peptides comprise at least one inclusion body tag operably linked to a peptide of interest. Expression of the fusion peptide in a host cell results in a product that is insoluble and contained within inclusion bodies in the cell and/or cell lysate. The inclusion bodies may then be purified and the protein of interest may be isolated after cleavage from the inclusion body tag.

15 Claims, 3 Drawing Sheets

OTHER PUBLICATIONS

Callaway et al., Modification of the C Terminus of Cecropin is Essebtial for Broad-Spectrum Antimicrobial Activity, Antimicrob. Agents & Chemo., 1993, vol. 37:1614.

Gram et al., A Novel Approach for High Level Production of a Recombinant Human Parathyroid Hormone Fragment in *Escherichia coli*, Bio/Technology, 1994, vol. 12:1017-1023.

Kuliopulos et al., Production, Purification, and Cleavage of Tandem Repeats of Recpmbinant Peptides, J. Am. Chem. Soc., 1994, vol. 116:4599.

Pilon et al., Ubiquitin Fusion Technology: Bioprocessing of Peptides, Biotechnol. Prog., 1997, vol. 13:374-379.

Haught et al., Recombinant Production and Purification of Novel Antisense Antimicrobial Peptide in *Escherichia coli*, Biotechnol. Bioengineer, 1998, vol. 57:55-61.

International Search Report and Written Opinion of corresponding International Patent Application No. PC/US2008/070802.

\* cited by examiner

```
CLUSTAL W (1.83) multiple sequence alignment

IBT136          ---------------------------QQRFQWQFEQQ----------------------   (SEQ ID NO: 17)
IBT138          ---------------------------QQRFQWQFEQQPE-GQQRFQWQFEQQ--------   (SEQ ID NO: 19)
IBT139          QQRFQWQFEQQPRGQQRFQWQFEQQPR-GQQRFQWQFEQQPE-GQQRFQWQFEQQ--------   (SEQ ID NO: 21)
IBT103          --------------QQRFQWQFEQQPR-GQQRFQWQFEQQPE-GQQRFQWQFEQQ--------   (SEQ ID NO: 15)
IBT139_CCPGCC   QQRFQWQFEQQPRGQQRFQWQFEQQPR-GQQRFQWQFEQQPE-GQQRFQWQFEQQGSCCPGCC   (SEQ ID NO: 31)
IBT182          --------------QQHFHWHFQQQPR-GQQHFHWHFQQQPE-GQQHFHWHFQQQ--------   (SEQ ID NO: 39)
IBT183          --------------QQHFHWHFQQQPR-GQQKFKWKFQQQPE-GQQHFHWHFQQQ--------   (SEQ ID NO: 41)
IBT184          --------------QQKFHWHFQQQPR-GQQKFHWHFQQQPE-GQQKFHWHFQQQ--------   (SEQ ID NO: 43)
IBT185          --------MASPCGQQRFQWQFEQQPC-GQQRFQWQFEQQPC-GQQRFQWQFEQQPCG-----   (SEQ ID NO: 45)
IBT186          --------MASCGQQRFQWQFEQQPRCGQQRFQWQFEQQPECGQQRFQWQFEQQPC-------   (SEQ ID NO: 27)
IBT187a         --------------QQKFKWKFQQQPR-GQQKFKWKFQQQPE-GQQKFKWKFQQQ--------   (SEQ ID NO: 47)
IBT187b         QQKFKWKFQQQPRGQQKFKWKFQQQPR-GQQKFKWKFQQQPE-GQQKFKWKFQKQ--------   (SEQ ID NO: 49)
```

FIG. 1

SEQUENCE LISTING

```
<160> NUMBER OF SEQ ID NOS: 262

<210> SEQ ID NO 1
<211> LENGTH: 4945
<212> TYPE: DNA
<213> ORGANISM: artificial sequence
<220> FEATURE:
<223> OTHER INFORMATION: plasmid

<400> SEQUENCE: 1
agatctcgat cccgcgaaat taatacgact cactataggg agaccacaac ggtttccctc      60
tagaaataat tttgtttaac tttaagaagg agatatacat atgtcgtact accatcacca     120
tcaccatcac ctcgaatcaa caagtttgta caaaaaagca ggctccgcgg ccgccccctt     180
```

-continued

```
caccggatcc atcgatccac gtttccacga aaactggccg tctgccggcg gtacctctac    240
ttccaaagct tccaccacta cgacttctag caaaaccacc actacatcct ctaagactac    300
cacgactacc tccaaaacct ctactacctc tagctcctct acgggcggcg ccactcacaa    360
gacctctact cagcgtctgc tggctgcata atgaaagggt gggcgcgccg acccagcttt    420
cttgtacaaa gtggttgatt cgaggctgct aacaaagccc gaaaggaagc tgagttggct    480
gctgccaccg ctgagcaata actagcataa cccctgggg cctctaaacg ggtcttgagg    540
ggttttttgc tgaaaggagg aactatatcc ggatatccac aggacgggtg tggtcgccat    600
gatcgcgtag tcgatagtgg ctccaagtag cgaagcgagc aggactgggc ggcggccaaa    660
gcggtcggac agtgctccga gaacgggtgc gcatagaaat tgcatcaacg catatagcgc    720
tagcagcacg ccatagtgac tggcgatgct gtcggaatgg acgatatccc gcaagaggcc    780
cggcagtacc ggcataacca agcctatgcc tacagcatcc agggtgacgg tgccgaggat    840
gacgatgagc gcattgttag atttcataca cggtgcctga ctgcgttagc aatttaactg    900
tgataaacta ccgcattaaa gcttatcgat gataagctgt caaacatgag aattcttgaa    960
gacgaaaggg cctcgtgata cgcctatttt tataggttaa tgtcatgata ataatggttt   1020
cttagacgtc aggtggcact tttcggggaa atgtgcgcgg aaccctatt tgtttatttt   1080 tctaaataca ttcaaatatg tatccgctca tgagacaata accctgataa atgcttcaat   1140
aatattgaaa aaggaagagt atgagtattc aacatttccg tgtcgccctt attcccttt    1200 ttgcggcatt ttgccttcct gttttgctc acccagaaac gctggtgaaa gtaaaagatg   1260
ctgaagatca gttgggtgca cgagtgggtt acatcgaact ggatctcaac agcggtaaga   1320
tccttgagag ttttcgcccc gaagaacgtt ttccaatgat gagcactttt aaagttctgc   1380
tatgtggcgc ggtattatcc cgtgttgacg ccgggcaaga gcaactcggt cgccgcatac   1440
actattctca gaatgacttg gttgagtact caccagtcac agaaaagcat cttacggatg   1500
gcatgacagt aagagaatta tgcagtgctg ccataaccat gagtgataac actgcggcca   1560
acttacttct gacaacgatc ggaggaccga aggagctaac cgcttttttg cacaacatgg   1620
gggatcatgt aactcgcctt gatcgttggg aaccggagct gaatgaagcc ataccaaacg   1680
acgagcgtga caccacgatg cctgcagcaa tggcaacaac gttgcgcaaa ctattaactg   1740
gcgaactact tactctagct tcccggcaac aattaataga ctggatggag gcggataaag   1800
ttgcaggacc acttctgcgc tcggcccttc cggctggctg gtttattgct gataaatctg   1860
gagccggtga gcgtgggtct cgcggtatca ttgcagcact ggggccagat ggtaagccct   1920
cccgtatcgt agttatctac acgacgggga gtcaggcaac tatggatgaa cgaaatagac   1980
agatcgctga gataggtgcc tcactgatta agcattggta actgtcagac caagtttact   2040
catatatact ttagattgat ttaaaacttc attttaatt taaaggatc taggtgaaga   2100 tccttttga taatctcatg accaaaatcc cttaacgtga gttttcgttc cactgagcgt   2160 cagacccgt agaaaagatc aaaggatctt cttgagatcc ttttttctg cgcgtaatct   2220 gctgcttgca aacaaaaaaa ccaccgctac cagcggtggt ttgtttgccg gatcaagagc   2280
taccaactct ttttccgaag gtaactggct tcagcagagc gcagatacca atactgtcc    2340 ttctagtgta gccgtagtta ggccaccact tcaagaactc tgtagcaccg cctacatacc   2400
tcgctctgct aatcctgtta ccagtggctg ctgccagtgg cgataagtcg tgtcttaccg   2460
ggttggactc aagacgatag ttaccggata aggcgcagcg gtcgggctga acggggggtt   2520
```

-continued

```
cgtgcacaca gcccagcttg gagcgaacga cctacaccga actgagatac ctacagcgtg    2580
agctatgaga aagcgccacg cttcccgaag ggagaaaggc ggacaggtat ccggtaagcg    2640
gcagggtcgg aacaggagag cgcacgaggg agcttccagg gggaaacgcc tggtatcttt    2700
atagtcctgt cgggtttcgc cacctctgac ttgagcgtcg attttttgtga tgctcgtcag   2760
gggggcggag cctatggaaa aacgccagca acgcggcctt tttacggttc ctggcctttt    2820
gctggccttt tgctcacatg ttctttcctg cgttatcccc tgattctgtg gataaccgta    2880
ttaccgcctt tgagtgagct gataccgctc gccgcagccg aacgaccgag cgcagcgagt    2940
cagtgagcga ggaagcggaa gagcgcctga tgcggtattt tctccttacg catctgtgcg    3000
gtatttcaca ccgcatatat ggtgcactct cagtacaatc tgctctgatg ccgcatagtt    3060
aagccagtat acactccgct atcgctacgt gactgggtca tggctgcgcc ccgacacccg    3120
ccaacacccg ctgacgcgcc ctgacgggct tgtctgctcc cggcatccgc ttacagacaa    3180
gctgtgaccg tctccgggag ctgcatgtgt cagaggtttt caccgtcatc accgaaacgc    3240
gcgaggcagc tgcggtaaag ctcatcagcg tggtcgtgaa gcgattcaca gatgtctgcc    3300
tgttcatccg cgtccagctc gttgagtttc tccagaagcg ttaatgtctg gcttctgata    3360
aagcgggcca tgttaagggc ggttttttcc tgtttggtca ctgatgcctc cgtgtaaggg    3420
ggatttctgt tcatgggggt aatgataccg atgaaacgag agaggatgct cacgatacgg    3480
gttactgatg atgaacatgc ccggttactg gaacgttgtg agggtaaaca actggcggta    3540
tggatgcggc gggaccagag aaaaatcact cagggtcaat gccagcgctt cgttaataca    3600
gatgtaggtg ttccacaggg tagccagcag catcctgcga tgcagatccg gaacataatg    3660
gtgcagggcg ctgacttccg cgtttccaga ctttacgaaa cacggaaacc gaagaccatt    3720
catgttgttg ctcaggtcgc agacgttttg cagcagcagt cgcttcacgt tcgctcgcgt    3780
atcggtgatt cattctgcta accagtaagg caaccccgcc agcctagccg ggtcctcaac    3840
gacaggagca cgatcatgcg cacccgtggc caggacccaa cgctgcccga tgcgccgc    3900
gtgcggctgc tggagatggc ggacgcgatg gatatgttct gccaagggtt ggtttgcgca    3960
ttcacagttc tccgcaagaa ttgattggct ccaattcttg gagtggtgaa tccgttagcg    4020
aggtgccgcc ggcttccatt caggtcgagg tggcccggct ccatgcaccg cgacgcaacg    4080
cggggaggca gacaaggtat agggcggcgc ctacaatcca tgccaacccg ttccatgtgc    4140
tcgccgaggc ggcataaatc gccgtgacga tcagcggtcc agtgatcgaa gttaggctgg    4200
taagagccgc gagcgatcct tgaagctgtc cctgatggtc gtcatctacc tgcctggaca    4260
gcatggcctg caacgcgggc atcccgatgc cgccggaagc gagaagaatc ataatgggga    4320
aggccatcca gcctcgcgtc gcgaacgcca gcaagacgta gcccagcgcg tcggccgcca    4380
tgccggcgat aatggcctgc ttctcgccga acgtttggt ggcgggacca gtgacgaagg    4440
cttgagcgag ggcgtgcaag attccgaata ccgcaagcga caggccgatc atcgtcgcgc    4500
tccagcgaaa gcggtcctcg ccgaaaatga cccagagcgc tgccggcacc tgtcctacga    4560
gttgcatgat aaagaagaca gtcataagtg cggcgacgat agtcatgccc cgcgcccacc    4620
ggaaggagct gactggttg aaggctctca agggcatcgg tcgatcgacg ctctccctta    4680
tgcgactcct gcattaggaa gcagcccagt agtaggttga ggccgttgag caccgccgcc    4740
gcaaggaatg gtgcatgcaa ggagatggcg cccaacagtc ccccggccac ggggcctgcc    4800
accatacccca cgccgaaaca agcgctcatg agcccgaagt ggcgagcccg atcttcccca    4860
tcggtgatgt cggcgatata ggcgccagca accgcacctg tggcgccggt gatgccggcc    4920
```
acgatgcgtc cggcgtagag gatcg                                         4945

<210> SEQ ID NO 2
<211> LENGTH: 5113
<212> TYPE: DNA
<213> ORGANISM: artificial sequence
<220> FEATURE:
<223> OTHER INFORMATION: plasmid

<400> SEQUENCE: 2

```
aagaaaccaa ttgtccatat tgcatcagac attgccgtca ctgcgtcttt tactggctct     60
tctcgctaac caaaccggta accccgctta ttaaaagcat tctgtaacaa agcgggacca    120
aagccatgac aaaaacgcgt aacaaaagtg tctataatca cggcagaaaa gtccacattg    180
attatttgca cggcgtcaca ctttgctatg ccatagcatt tttatccata agattagcgg    240
atcttacctg acgctttttta tcgcaactct ctactgtttc tccatacccg tttttttgggc   300
taacaggagg aattacatat gcataccccca gaacacatca ccgccgtggt acagcgcttt    360
gtggctgcgc tcaatgccgg cgatctggac ggcatcgtcg cgctgtttgc cgatgacgcc    420
acggtggaag agcccgtggg ttccgagccc aggtccggta cggctgcgtg tcgtgagttt    480
tacgccaact cgctcaaact gccttttggcg gtggagctga cgcaggagtg ccgcgcggtc    540
gccaacgaag cggccttcgc tttcaccgtc agcttcgagt atcagggccg caagaccgta    600
gttgcgccct gtgatcactt tcgcttcaat ggcgccggca aggtggtgag catccgcgcc    660
ttgtttggcg agaagaatat tcacgcatgc cagggatccg acccaggtaa tacttctcaa    720
ctgtccactg gtaaaggtaa cacctctcag ctgtctaccg gcaaaggtaa tacctctcaa    780
ctgagcacgg gtaaaggctg gggtgatccg gtaacacca gccagctgtc tacgggtaaa    840
ggtaacacgt cccagctgag cactggcaaa ggtaacactt ctcagctgtc cacgggcaaa    900
ggttggggtg actaataagg cgcgccgacc cagctttctt gtacaaagtg gttgattcga    960
ggctgctaac aaagcccgaa aggaagctga gttggctgct gccaccgctg agcaataact   1020
agcataaccc cttggggcct ctaaacgggt cttgaggggt ttttgctga aggaggaac     1080
tatatccgga tatccacagg acgggtgtgg tcgccatgat cgcgtagtcg atagtggctc   1140
caagtagcga agcgagcagg actgggcggc ggccaaagcg gtcggacagt gctccgagaa   1200
cgggtgcgca tagaaattgc atcaacgcat atagcgctag cagcacgcca tagtgactgg   1260
cgatgctgtc ggaatggacg atatcccgca agaggcccgg cagtaccggc ataaccaagc   1320
ctatgcctac agcatccagg gtgacggtgc cgaggatgac gatgagcgca ttgttagatt   1380
tcatacacgg tgcctgactg cgttagcaat ttaactgtga taaactaccg cattaaagct   1440
tatcgatgat aagctgtcaa acatgagaat tcgaagcttg gctgttttgg cggatgagag   1500
aagattttca gcctgataca gattaaatca gaacgcagaa gcggtctgat aaaacagaat   1560
ttgcctggcg gcagtagcgc ggtggtccca cctgacccca tgccgaactc agaagtgaaa   1620
cgccgtagcg ccgatggtag tgtggggtct ccccatgcga gagtagggaa ctgccaggca   1680
tcaaataaaa cgaaaggctc agtcgaaaga ctgggccttt cgttttatct gttgtttgtc   1740
ggtgaacgct ctcctgagta ggacaaatcc gccgggagcg gatttgaacg ttgcgaagca   1800
acggcccgga gggtggcggg caggacgccc gccataaact gccaggcatc aaattaagca   1860
gaaggccatc ctgacggatg gcctttttgc gttctacaa actctttgt ttattttct    1920
aaatacattc aaatatgtat ccgctcatga gacaataacc ctgataaatg cttcaataat   1980
```

```
attgaaaaag gaagagtatg agtattcaac atttccgtgt cgcccttatt ccctttttg    2040
cggcattttg ccttcctgtt tttgctcacc cagaaacgct ggtgaaagta aaagatgctg   2100
aagatcagtt gggtgcacga gtgggttaca tcgaactgga tctcaacagc ggtaagatcc   2160
ttgagagttt tcgccccgaa gaacgttttc caatgatgag cacttttaaa gttctgctat   2220
gtggcgcggt attatcccgt gttgacgccg gcaagagca actcggtcgc cgcatacact    2280
attctcagaa tgacttggtt gagtactcac cagtcacaga aaagcatctt acggatggca   2340
tgacagtaag agaattatgc agtgctgcca taaccatgag tgataacact gcggccaact   2400
tacttctgac aacgatcgga ggaccgaagg agctaaccgc ttttttgcac aacatggggg   2460
atcatgtaac tcgccttgat cgttgggaac cggagctgaa tgaagccata ccaaacgacg   2520
agcgtgacac cacgatgcct gtagcaatgg caacaacgtt gcgcaaacta ttaactggcg   2580
aactacttac tctagcttcc cggcaacaat taatagactg gatggaggcg gataaagttg   2640
caggaccact tctgcgctcg gcccttccgg ctggctggtt tattgctgat aaatctggag   2700
ccggtgagcg tgggtctcgc ggtatcattg cagcactggg gccagatggt aagccctccc   2760
gtatcgtagt tatctacacg acggggagtc aggcaactat ggatgaacga atagacaga   2820
tcgctgagat aggtgcctca ctgattaagc attggtaact gtcagaccaa gtttactcat   2880
atatacttta gattgattta aacttcatt tttaatttaa aaggatctag gtgaagatcc    2940
tttttgataa tctcatgacc aaaatccctt aacgtgagtt ttcgttccac tgagcgtcag   3000
accccgtaga aaagatcaaa ggatcttctt gagatccttt ttttctgcgc gtaatctgct   3060
gcttgcaaac aaaaaaacca ccgctaccag cggtggtttg tttgccggat caagagctac   3120
caactctttt tccgaaggta actggcttca gcagagcgca gataccaaat actgtccttc   3180
tagtgtagcc gtagttaggc caccacttca agaactctgt agcaccgcct acatacctcg   3240
ctctgctaat cctgttacca gtggctgctg ccagtggcga taagtcgtgt cttaccgggt   3300
tggactcaag acgatagtta ccggataagg cgcagcggtc gggctgaacg gggggttcgt   3360
gcacacagcc cagcttggag cgaacgacct acaccgaact gagatacct cagcgtgagc    3420
tatgagaaag cgccacgctt cccgaaggga gaaaggcgga caggtatccg gtaagcggca   3480
gggtcggaac aggagagcgc acgagggagc ttccagggg aaacgcctgg tatctttata   3540
gtcctgtcgg gtttcgccac ctctgacttg agcgtcgatt tttgtgatgc tcgtcagggg   3600
ggcggagcct atgaaaaac gccagcaacg cggccttttt acggttcctg ccttttgct    3660
ggccttttgc tcacatgttc tttcctgcgt tatcccctga ttctgtggat aaccgtatta   3720
ccgcctttga gtgagctgat accgctcgcc gcagccgaac gaccgagcgc agcgagtcag   3780
tgagcgagga agcggaagag cgcctgatgc ggtattttct ccttacgcat ctgtgcggta   3840
tttcacaccg catatatggt gcactctcag tacaatctgc tctgatgccg catagttaag   3900
ccagtataca ctccgctatc gctacgtgac tgggtcatgg ctgcgccccg acacccgcca   3960
acacccgctg acgcgccctg acgggcttgt ctgctcccgg catccgctta cagacaagct   4020
gtgaccgtct ccgggagctg catgtgtcag aggttttcac cgtcatcacc gaaacgcgcg   4080
aggcagcaga tcaattcgcg cgcgaaggcg aagcggcatg cataatgtgc ctgtcaaatg   4140
gacgaagcag ggattctgca aaccctatgc tactccgtca agccgtcaat tgtctgattc   4200
gttaccaatt atgacaactt gacggctaca tcattcactt tttcttcaca accggcacgg   4260
aactcgctcg gctggccccc ggtgcatttt taaataccc gcgagaaata gagttgatcg    4320
tcaaaaccaa cattgcgacc gacggtggcg ataggcatcc gggtggtgct caaaagcagc   4380
```

-continued

```
ttcgcctggc tgatacgttg gtcctcgcgc cagcttaaga cgctaatccc taactgctgg    4440
cggaaaagat gtgacagacg cgacggcgac aagcaaacat gctgtgcgac gctggcgata    4500
tcaaaattgc tgtctgccag gtgatcgctg atgtactgac aagcctcgcg tacccgatta    4560
tccatcggtg gatggagcga ctcgttaatc gcttccatgc gccgcagtaa caattgctca    4620
agcagattta cgccagcag ctccgaatag cgcccttccc cttgcccggc gttaatgatt     4680
tgcccaaaca ggtcgctgaa atgcggctgg tgcgcttcat ccgggcgaaa gaaccccgta    4740
ttggcaaata ttgacggcca gttaagccat tcatgccagt aggcgcgcgg acgaaagtaa    4800
acccactggt gataccattc gcgagcctcc ggatgacgac cgtagtgatg aatctctcct    4860
ggcgggaaca gcaaaatatc acccggtcgg caaacaaatt ctcgtccctg attttcacc     4920 accccctgac cgcgaatggt gagattgaga atataacctt tcattcccag cggtcggtcg    4980
ataaaaaaat cgagataacc gttggcctca atcggcgtta aacccgccac cagatgggca    5040
ttaaacgagt atcccggcag cagggatca ttttgcgctt cagccatact tttcatactc     5100
ccgccattca gag                                                      5113
```

```
<210> SEQ ID NO 3
<211> LENGTH: 12
<212> TYPE: PRT
<213> ORGANISM: artificial sequence
<220> FEATURE:
<223> OTHER INFORMATION: Hair-binding peptide

<400> SEQUENCE: 3

Ile Pro Trp Trp Asn Ile Arg Ala Pro Leu Asn Ala
1               5                   10

<210> SEQ ID NO 4
<211> LENGTH: 7
<212> TYPE: PRT
<213> ORGANISM: artificial sequence
<220> FEATURE:
<223> OTHER INFORMATION: Hair-binding peptide

<400> SEQUENCE: 4

Asn Thr Ser Gln Leu Ser Thr
1               5

<210> SEQ ID NO 5
<211> LENGTH: 8
<212> TYPE: PRT
<213> ORGANISM: artificial sequence
<220> FEATURE:
<223> OTHER INFORMATION: Hair-binding peptide

<400> SEQUENCE: 5

Arg Thr Asn Ala Ala Asp His Pro
1               5

<210> SEQ ID NO 6
<211> LENGTH: 210
<212> TYPE: DNA
<213> ORGANISM: artificial sequence
<220> FEATURE:
<223> OTHER INFORMATION: Synthetic construct. Nucleic acid sequence
      encoding a multi-block hair-binding peptide

<400> SEQUENCE: 6
ggatccgatc cgaacaccag tcagctgagt accggcggcg ccgcaccaa cgccgcggat     60
```

```
catccgaaat gtggcggcgg caacaccagc cagctgagca ccggtggcgg ccgtaccaat      120
gcggcggatc atccgaaatg tggtggtggc aatacctctc agctgagcac gggcggcggc      180
cgtaccaatg ccgcggatca tccgaaatgc                                       210
```

```
<210> SEQ ID NO 7
<211> LENGTH: 70
<212> TYPE: PRT
<213> ORGANISM: artificial sequence
<220> FEATURE:
<223> OTHER INFORMATION: Synthetic construct. Multi-block hair-binding
      peptide

<400> SEQUENCE: 7
```

```
Gly Ser Asp Pro Asn Thr Ser Gln Leu Ser Thr Gly Gly Gly Arg Thr
 1               5                  10                  15

Asn Ala Ala Asp His Pro Lys Cys Gly Gly Gly Asn Thr Ser Gln Leu
             20                  25                  30

Ser Thr Gly Gly Gly Arg Thr Asn Ala Ala Asp His Pro Lys Cys Gly
         35                  40                  45

Gly Gly Asn Thr Ser Gln Leu Ser Thr Gly Gly Gly Arg Thr Asn Ala
     50                  55                  60

Ala Asp His Pro Lys Cys
65                  70
```

```
<210> SEQ ID NO 8
<211> LENGTH: 219
<212> TYPE: DNA
<213> ORGANISM: artificial sequence
<220> FEATURE:
<223> OTHER INFORMATION: Synthetic construct. Nucleic acid sequence
      encoding a multi-block hair-binding peptide

<400> SEQUENCE: 8
```

```
ggatccgacc caggtaatac ttctcaactg tccactggta aaggtaacac ctctcagctg       60
tctaccggca aaggtaatac ctctcaactg agcacgggta aaggctgggg tgatccgggt      120
aacaccagcc agctgtctac gggtaaaggt aacacgtccc agctgagcac tggcaaaggt      180
aacacttctc agctgtccac gggcaaaggt tggggtgac                             219
```

```
<210> SEQ ID NO 9
<211> LENGTH: 73
<212> TYPE: PRT
<213> ORGANISM: artificial sequence
<220> FEATURE:
<223> OTHER INFORMATION: hair-binding peptide

<400> SEQUENCE: 9
```

```
Gly Ser Asp Pro Gly Asn Thr Ser Gln Leu Ser Thr Gly Lys Gly Asn
 1               5                  10                  15

Thr Ser Gln Leu Ser Thr Gly Lys Gly Asn Thr Ser Gln Leu Ser Thr
             20                  25                  30

Gly Lys Gly Trp Gly Asp Pro Gly Asn Thr Ser Gln Leu Ser Thr Gly
         35                  40                  45

Lys Gly Asn Thr Ser Gln Leu Ser Thr Gly Lys Gly Asn Thr Ser Gln
     50                  55                  60

Leu Ser Thr Gly Lys Gly Trp Gly Asp
65                  70
```

```
<210> SEQ ID NO 10
<211> LENGTH: 195
```

<212> TYPE: DNA
<213> ORGANISM: artificial sequence
<220> FEATURE:
<223> OTHER INFORMATION: Synthetic construct. Nucleic acid sequence
    encoding a multi-block hair-binding peptide

<400> SEQUENCE: 10

```
ggatccgacc ctggtatccc gtggtggaac attcgcgcac ctctgaatgc tggtgctggt    60
attccgtggt ggaacatccg tgctcctctg aacgcgggtg ctccggtcc gggctccggt    120
ggcaacacga gccaactgag caccggtggt ggcaacactt cccagctgtc caccggcggt    180
ccgaaaaagt aataa                                                     195
```

<210> SEQ ID NO 11
<211> LENGTH: 63
<212> TYPE: PRT
<213> ORGANISM: artificial sequence
<220> FEATURE:
<223> OTHER INFORMATION: hair-binding peptide

<400> SEQUENCE: 11

```
Gly Ser Asp Pro Gly Ile Pro Trp Trp Asn Ile Arg Ala Pro Leu Asn
1               5                  10                   15

Ala Gly Ala Gly Ile Pro Trp Trp Asn Ile Arg Ala Pro Leu Asn Ala
            20                  25                  30

Gly Gly Ser Gly Pro Gly Ser Gly Gly Asn Thr Ser Gln Leu Ser Thr
        35                  40                  45

Gly Gly Gly Asn Thr Ser Gln Leu Ser Thr Gly Gly Pro Lys Lys
    50                  55                  60
```

<210> SEQ ID NO 12
<211> LENGTH: 120
<212> TYPE: DNA
<213> ORGANISM: artificial sequence
<220> FEATURE:
<223> OTHER INFORMATION: Synthetic construct. Nucleic acid sequence
    encoding a multi-block hair-binding peptide

<400> SEQUENCE: 12

```
ggatccgacc ctaatacttc tcaactgtct actggtggtg gtggtcatgg ccaccagaaa    60
cagcatggtc tgggccacgg ccacaaacac ggccacggtc acggtcatgg ccacggcaaa   120
```

<210> SEQ ID NO 13
<211> LENGTH: 40
<212> TYPE: PRT
<213> ORGANISM: artificial sequence
<220> FEATURE:
<223> OTHER INFORMATION: hair-binding peptide

<400> SEQUENCE: 13

```
Gly Ser Asp Pro Asn Thr Ser Gln Leu Ser Thr Gly Gly Gly Gly His
1               5                  10                   15

Gly His Gln Lys Gln His Gly Leu Gly His Gly His Lys His Gly His
            20                  25                  30

Gly His Gly His Gly His Gly Lys
        35                  40
```

<210> SEQ ID NO 14
<211> LENGTH: 117
<212> TYPE: DNA
<213> ORGANISM: artificial sequence
<220> FEATURE:
<223> OTHER INFORMATION: Synthetic construct. Nucleic acid sequence encoding inclusion body tag IBT103

<400> SEQUENCE: 14
cagcagcgtt tccagtggca gttcgaacag cagccgcgtg gtcagcagcg tttccagtgg    60
cagttcgaac agcagccgga aggtcagcag cgtttccagt ggcagttcga acagcag      117

<210> SEQ ID NO 15
<211> LENGTH: 39
<212> TYPE: PRT
<213> ORGANISM: artificial sequence
<220> FEATURE:
<223> OTHER INFORMATION: inclusion body tag IBT103

<400> SEQUENCE: 15

Gln Gln Arg Phe Gln Trp Gln Phe Glu Gln Gln Pro Arg Gly Gln Gln
1               5                   10                  15

Arg Phe Gln Trp Gln Phe Glu Gln Gln Pro Glu Gly Gln Gln Arg Phe
            20                  25                  30

Gln Trp Gln Phe Glu Gln Gln
        35

<210> SEQ ID NO 16
<211> LENGTH: 36
<212> TYPE: DNA
<213> ORGANISM: artificial sequence
<220> FEATURE:
<223> OTHER INFORMATION: Synthetic construct. Nucleic acid sequence
      encoding inclusion body tag IBT136

<400> SEQUENCE: 16
atgcagcagc gtttccagtg gcagttcgaa cagcag                              36

<210> SEQ ID NO 17
<211> LENGTH: 11
<212> TYPE: PRT
<213> ORGANISM: artificial sequence
<220> FEATURE:
<223> OTHER INFORMATION: inclusion body tag IBT136

<400> SEQUENCE: 17

Gln Gln Arg Phe Gln Trp Gln Phe Glu Gln Gln
1               5                   10

<210> SEQ ID NO 18
<211> LENGTH: 78
<212> TYPE: DNA
<213> ORGANISM: artificial sequence
<220> FEATURE:
<223> OTHER INFORMATION: Synthetic construct. Nucleic acid sequence
      encoding inclusion body tag IBT138

<400> SEQUENCE: 18
atgcagcagc gtttccagtg gcagttcgaa cagcagccgg aaggtcagca gcgtttccag    60
tggcagttcg aacagcag                                                  78

<210> SEQ ID NO 19
<211> LENGTH: 25
<212> TYPE: PRT
<213> ORGANISM: artificial sequence
<220> FEATURE:
<223> OTHER INFORMATION: inclusion body tag IBT138

<400> SEQUENCE: 19

Gln Gln Arg Phe Gln Trp Gln Phe Glu Gln Gln Pro Glu Gly Gln Gln

```
1               5              10              15

Arg Phe Gln Trp Gln Phe Glu Gln Gln
         20              25
```

<210> SEQ ID NO 20
<211> LENGTH: 162
<212> TYPE: DNA
<213> ORGANISM: artificial sequence
<220> FEATURE:
<223> OTHER INFORMATION: Synthetic construct. Nucleic acid sequence
      encoding inclusion body tag IBT139

<400> SEQUENCE: 20

```
atgcagcagc gtttccagtg gcagttcgaa cagcagccgc gtggtcagca gcgtttccag    60
tggcagttcg aacagcagcc gcgtggtcag cagcgtttcc agtggcagtt cgaacagcag   120
ccggaaggtc agcagcgttt ccagtggcag ttcgaacagc ag                      162
```

<210> SEQ ID NO 21
<211> LENGTH: 53
<212> TYPE: PRT
<213> ORGANISM: artificial sequence
<220> FEATURE:
<223> OTHER INFORMATION: inclusion body tag IBT139

<400> SEQUENCE: 21

```
Gln Gln Arg Phe Gln Trp Gln Phe Glu Gln Gln Pro Arg Gly Gln Gln
1               5                   10                  15

Arg Phe Gln Trp Gln Phe Glu Gln Gln Pro Arg Gly Gln Gln Arg Phe
            20                  25                  30

Gln Trp Gln Phe Glu Gln Gln Pro Glu Gly Gln Gln Arg Phe Gln Trp
        35                  40                  45

Gln Phe Glu Gln Gln
    50
```

<210> SEQ ID NO 22
<211> LENGTH: 387
<212> TYPE: DNA
<213> ORGANISM: artificial sequence
<220> FEATURE:
<223> OTHER INFORMATION: Synthetic construct. Nucleic acid sequence
      encoding multi-block hair binding peptide

<400> SEQUENCE: 22

```
gaccctggca ttccgtggtg gaacattcgt gctcctctga atgcaggtgc gggcatccct    60
tggtggaata ttcgtgctcc gctgaacgcc ggtggttccg gtccgggtag cggtggtaat   120
acttctcagc tgtccacggg tggcggtaac actagccagc tgagcacggg cggccctaaa   180
aagccgggcg acccgggtat ccgtggtgg aatatccgtg ccccgctgaa cgcaggtgcc    240
ggcatcccgt ggtggaacat tcgtgcacct ctgaatgctg tggttccgg tccaggctct    300 ggcggcaaca cttcccagct gtccaccggc ggtggcaaca ccagccagct gtctactggt   360
ggtccgaaga aaccgggtga ctaataa                                       387
```

<210> SEQ ID NO 23
<211> LENGTH: 129
<212> TYPE: PRT
<213> ORGANISM: artificial sequence
<220> FEATURE:
<223> OTHER INFORMATION: Synthetic construct. Multi-block hair-binding
      peptide

<400> SEQUENCE: 23

```
Gly Ser Asp Pro Gly Ile Pro Trp Trp Asn Ile Arg Ala Pro Leu Asn
1               5                   10                  15

Ala Gly Ala Gly Ile Pro Trp Trp Asn Ile Arg Ala Pro Leu Asn Ala
            20                  25                  30

Gly Gly Ser Gly Pro Gly Ser Gly Gly Asn Thr Ser Gln Leu Ser Thr
        35                  40                  45

Gly Gly Gly Asn Thr Ser Gln Leu Ser Thr Gly Gly Pro Lys Lys Pro
    50                  55                  60

Gly Asp Pro Gly Ile Pro Trp Trp Asn Ile Arg Ala Pro Leu Asn Ala
65              70                  75                  80

Gly Ala Gly Ile Pro Trp Trp Asn Ile Arg Ala Pro Leu Asn Ala Gly
            85                  90                  95

Gly Ser Gly Pro Gly Ser Gly Gly Asn Thr Ser Gln Leu Ser Thr Gly
        100                 105                 110

Gly Gly Asn Thr Ser Gln Leu Ser Thr Gly Gly Pro Lys Lys Pro Gly
    115                 120                 125

Asp
```

```
<210> SEQ ID NO 24
<211> LENGTH: 555
<212> TYPE: DNA
<213> ORGANISM: artificial sequence
<220> FEATURE:
<223> OTHER INFORMATION: Synthetic construct - chimeric gene encoding
      fusion peptide IBT139-HC776124

<400> SEQUENCE: 24
atgcagcagc gtttccagtg gcagttcgaa cagcagccgc gtggtcagca gcgtttccag    60
tggcagttcg aacagcagcc gcgtggtcag cagcgtttcc agtggcagtt cgaacagcag   120
ccggaaggtc agcagcgttt ccagtggcag ttcgaacagc agggatccga ccctggcatt

-continued

```
Arg Ala Pro Leu Asn Ala Gly Ala Gly Ile Pro Trp Trp Asn Ile Arg
 65                  70                  75                  80

Ala Pro Leu Asn Ala Gly Gly Ser Gly Pro Gly Ser Gly Gly Asn Thr
                 85                  90                  95

Ser Gln Leu Ser Thr Gly Gly Gly Asn Thr Ser Gln Leu Ser Thr Gly
            100                 105                 110

Gly Pro Lys Lys Pro Gly Asp Pro Gly Ile Pro Trp Trp Asn Ile Arg
        115                 120                 125

Ala Pro Leu Asn Ala Gly Ala Gly Ile Pro Trp Trp Asn Ile Arg Ala
    130                 135                 140

Pro Leu Asn Ala Gly Gly Ser Gly Pro Gly Ser Gly Gly Asn Thr Ser
145                 150                 155                 160

Gln Leu Ser Thr Gly Gly Gly Asn Thr Ser Gln Leu Ser Thr Gly Gly
                165                 170                 175

Pro Lys Lys Pro Gly Asp
            180
```

<210> SEQ ID NO 26
<211> LENGTH: 144
<212> TYPE: DNA
<213> ORGANISM: artificial sequence
<220> FEATURE:
<223> OTHER INFORMATION: Synthetic construct. Nucleic acid sequence encoding inclusion body tag IBT186

<400> SEQUENCE: 26

```
atggcttctt gtggtcagca acgtttccaa tggcaatttg aacagcagcc tcgctgcggt      60
caacagcgct tccagtggca gtttgaacag cagccagaat gcggtcagca acgctttcag     120
tggcaatttg aacaacaacc gtgc                                            144
```

<210> SEQ ID NO 27
<211> LENGTH: 48
<212> TYPE: PRT
<213> ORGANISM: artificial sequence
<220> FEATURE:
<223> OTHER INFORMATION: Synthetic construct. Inclusion body tag IBT186

<400> SEQUENCE: 27

```
Met Ala Ser Cys Gly Gln Gln Arg Phe Gln Trp Gln Phe Glu Gln Gln
  1               5                  10                  15

Pro Arg Cys Gly Gln Gln Arg Phe Gln Trp Gln Phe Glu Gln Gln Pro
                 20                  25                  30

Glu Cys Gly Gln Gln Arg Phe Gln Trp Gln Phe Glu Gln Gln Pro Cys
             35                  40                  45
```

<210> SEQ ID NO 28
<211> LENGTH: 534
<212> TYPE: DNA
<213> ORGANISM: artificial sequence
<220> FEATURE:
<223> OTHER INFORMATION: Synthetic construct - chimeric gene encoding fusion peptide IBT186-HC776124

<400> SEQUENCE: 28

```
atggctagct gtggtcagca acgtttccaa tggcaatttg aacagcagcc tcgctgcggt      60
caacagcgct tccagtggca gtttgaacag cagccagaat gcggtcagca acgctttcag     120
tggcaatttg aacaacaacc gtgcggatcc gaccctggca ttccgtggtg aacattcgt      180 gctc

```
ggtggttccg gtccgggtag cggtggtaat acttctcagc tgtccacggg tggcggtaac    300
actagccagc tgagcacggg cggccctaaa aagccgggcg acccgggtat tccgtggtgg    360
aatatccgtg ccccgctgaa cgcaggtgcc ggcatcccgt ggtggaacat tcgtgcacct    420
ctgaatgctg gtggttccgg tccaggctct ggcggcaaca cttcccagct gtccaccggc    480
ggtggcaaca ccagccagct gtctactggt ggtccgaaga accgggtga ctaa           534
```

```
<210> SEQ ID NO 29
<211> LENGTH: 177
<212> TYPE: PRT
<213> ORGANISM: artificial sequence
<220> FEATURE:
<223> OTHER INFORMATION: Synthetic construct - fusion peptide
      IBT186-HC776124

<400> SEQUENCE: 29
```

```
Met Ala Ser Cys Gly Gln Gln Arg Phe Gln Trp Gln Phe Glu Gln Gln
1               5                   10                  15

Pro Arg Cys Gly Gln Gln Arg Phe Gln Trp Gln Phe Glu Gln Gln Pro
                20                  25                  30

Glu Cys Gly Gln Gln Arg Phe Gln Trp Gln Phe Glu Gln Gln Pro Cys
            35                  40                  45

Gly Ser Asp Pro Gly Ile Pro Trp Trp Asn Ile Arg Ala Pro Leu Asn
        50                  55                  60

Ala Gly Ala Gly Ile Pro Trp Trp Asn Ile Arg Ala Pro Leu Asn Ala
65                  70                  75                  80

Gly Gly Ser Gly Pro Gly Ser Gly Gly Asn Thr Ser Gln Leu Ser Thr
                85                  90                  95

Gly Gly Gly Asn Thr Ser Gln Leu Ser Thr Gly Gly Pro Lys Lys Pro
            100                 105                 110

Gly Asp Pro Gly Ile Pro Trp Trp Asn Ile Arg Ala Pro Leu Asn Ala
        115                 120                 125

Gly Ala Gly Ile Pro Trp Trp Asn Ile Arg Ala Pro Leu Asn Ala Gly
    130                 135                 140

Gly Ser Gly Pro Gly Ser Gly Gly Asn Thr Ser Gln Leu Ser Thr Gly
145                 150                 155                 160

Gly Gly Asn Thr Ser Gln Leu Ser Thr Gly Pro Lys Lys Pro Gly
                165                 170                 175

Asp
```

```
<210> SEQ ID NO 30
<211> LENGTH: 186
<212> TYPE: DNA
<213> ORGANISM: artificial sequence
<220> FEATURE:
<223> OTHER INFORMATION: Synthetic construct. Nucleic acid sequence
      encoding inclusion body tag IBT139.CCPGCC

<400> SEQUENCE: 30
```

```
atgcagcagc gtttccagtg gcagttcgaa cagcagccgc gtggtcagca gcgtttccag    60
tggcagttcg aacagcagcc gcgtggtcag cagcgtttcc agtggcagtt cgaacagcag    120
ccggaaggtc agcagcgttt ccagtggcag ttcgaacagc aggatcttg ctgtccgggc    180 tgttgc                                                              186
```

```
<210> SEQ ID NO 31
<211> LENGTH: 61
```

-continued

<210> SEQ ID NO 31
<211> LENGTH: 61
<212> TYPE: PRT
<213> ORGANISM: artificial sequence
<220> FEATURE:
<223> OTHER INFORMATION: Synthetic construct - inclusion body tag
      IBT139.CCPGCC

<400> SEQUENCE: 31

Gln Gln Arg Phe Gln Trp Gln Phe Glu Gln Gln Pro Arg Gly Gln Gln
1               5                   10                  15

Arg Phe Gln Trp Gln Phe Glu Gln Gln Pro Arg Gly Gln Gln Arg Phe
            20                  25                  30

Gln Trp Gln Phe Glu Gln Gln Pro Arg Gly Gln Gln Arg Phe Gln Trp
        35                  40                  45

Gln Phe Glu Gln Gln Gly Ser Cys Cys Pro Gly Cys Cys
        50                  55                  60

<210> SEQ ID NO 32
<211> LENGTH: 18
<212> TYPE: DNA
<213> ORGANISM: artificial sequence
<220> FEATURE:
<223> OTHER INFORMATION: Synthetic construct - nucleic acid sequence
      encoding tetracysteine tag

<400> SEQUENCE: 32
tgctgtccgg gctgttgc                                              18

<210> SEQ ID NO 33
<211> LENGTH: 6
<212> TYPE: PRT
<213> ORGANISM: artificial sequence
<220> FEATURE:
<223> OTHER INFORMATION: Synthetic construct - tetracysteine tag

<400> SEQUENCE: 33

Cys Cys Pro Gly Cys Cys
1               5

<210> SEQ ID NO 34
<211> LENGTH: 24
<212> TYPE: DNA
<213> ORGANISM: artificial sequence
<220> FEATURE:
<223> OTHER INFORMATION: Primer

<400> SEQUENCE: 34
gatcttgctg tccgggctgt tgcg                                       24

<210> SEQ ID NO 35
<211> LENGTH: 24
<212> TYPE: DNA
<213> ORGANISM: artificial sequence
<220> FEATURE:
<223> OTHER INFORMATION: Primer

<400> SEQUENCE: 35
gatccgcaac agcccggaca gcaa                                       24

<210> SEQ ID NO 36
<211> LENGTH: 579
<212> TYPE: DNA
<213> ORGANISM: artificial sequence
<220> FEATURE:
<223> OTHER INFORMATION: Synthetic construct - chimeric gene encoding
      fusion peptide IBT139.CCPGCC-HC776124

```
<400> SEQUENCE: 36
atgcagcagc gtttccagtg gcagttcgaa cagcagccgc gtggtcagca gcgtttccag      60
tggcagttcg aacagcagcc gcgtggtcag cagcgtttcc agtggcagtt cgaacagcag     120
ccggaaggtc agcagcgttt ccagtggcag ttcgaacaga gggatcttgc tgtccgggc      180 tgttgcggat ccgaccctgg cattccgtgg tggaacattc gtgctcctct gaatgcaggt     240
gcgggcatcc cttggtggaa tattcgtgct ccgctgaacg ccggtggttc cggtccgggt     300
agcggtggta atacttctca gctgtccacg ggtggcggta acactagcca gctgagcacg     360
ggcggcccta aaaagccggg cgacccgggt attccgtggt ggaatatccg tgccccgctg     420
aacgcaggtg ccggcatccc gtggtggaac attcgtgcac ctctgaatgc tggtggttcc     480
ggtccaggct ctggcggcaa cacttcccag ctgtccaccg gcggtggcaa caccagccag     540
ctgtctactg gtggtccgaa gaaaccgggt gactaataa                            579
```

```
<210> SEQ ID NO 37
<211> LENGTH: 190
<212> TYPE: PRT
<213> ORGANISM: artificial sequence
<220> FEATURE:
<223> OTHER INFORMATION: Synthetic construct - fusion peptide
      IBT139.CCPGCC-HC776124

<400> SEQUENCE: 37
```

```
Gln Gln Arg Phe Gln Trp Gln Phe Glu Gln Gln Pro Arg Gly Gln Gln
1               5                   10                  15

Arg Phe Gln Trp Gln Phe Glu Gln Gln Pro Arg Gly Gln Gln Arg Phe
            20                  25                  30

Gln Trp Gln Phe Glu Gln Gln Pro Glu Gly Gln Gln Arg Phe Gln Trp
        35                  40                  45

Gln Phe Glu Gln Gln Gly Ser Cys Cys Pro Gly Cys Cys Gly Ser Asp
    50                  55                  60

Pro Gly Ile Pro Trp Trp Asn Ile Arg Ala Pro Leu Asn Ala Gly Ala
65                  70                  75                  80

Gly Ile Pro Trp Trp Asn Ile Arg Ala Pro Leu Asn Ala Gly Gly Ser
                85                  90                  95

Gly Pro Gly Ser Gly Gly Asn Thr Ser Gln Leu Ser Thr Gly Gly Gly
            100                 105                 110

Asn Thr Ser Gln Leu Ser Thr Gly Gly Pro Lys Lys Pro Gly Asp Pro
        115                 120                 125

Gly Ile Pro Trp Trp Asn Ile Arg Ala Pro Leu Asn Ala Gly Ala Gly
    130                 135                 140

Ile Pro Trp Trp Asn Ile Arg Ala Pro Leu Asn Ala Gly Gly Ser Gly
145                 150                 155                 160

Pro Gly Ser Gly Gly Asn Thr Ser Gln Leu Ser Thr Gly Gly Gly Asn
                165                 170                 175

Thr Ser Gln Leu Ser Thr Gly Gly Pro Lys Lys Pro Gly Asp
            180                 185                 190
```

```
<210> SEQ ID NO 38
<211> LENGTH: 120
<212> TYPE: DNA
<213> ORGANISM: artificial sequence
<220> FEATURE:
<223> OTHER INFORMATION: Synthetic construct. Nucleic acid sequence
      encoding inclusion body tag IBT182

<400> SEQUENCE: 38
```

```
atgcagcagc attttcattg cattttcag cagcagccgc gcggccagca gcattttcat    60
tggcattttc agcagcagcc ggaaggccag cagcattttc attggcattt tcagcagcag   120
```

<210> SEQ ID NO 39
<211> LENGTH: 39
<212> TYPE: PRT
<213> ORGANISM: artificial sequence
<220> FEATURE:
<223> OTHER INFORMATION: Synthetic construct. Inclusion body tag IBT182

<400> SEQUENCE: 39

```
Gln Gln His Phe His Trp His Phe Gln Gln Gln Pro Arg Gly Gln Gln
1               5                   10                  15

His Phe His Trp His Phe Gln Gln Gln Pro Glu Gly Gln Gln His Phe
            20                  25                  30

His Trp His Phe Gln Gln Gln
        35
```

<210> SEQ ID NO 40
<211> LENGTH: 120
<212> TYPE: DNA
<213> ORGANISM: artificial sequence
<220> FEATURE:
<223> OTHER INFORMATION: Synthetic construct. Nucleic acid sequence
      encoding inclusion body tag IBT183

<400> SEQUENCE: 40

```
atgcagcagc attttcattg cattttcag cagcagccgc gcggccagca gaaatttaaa    60
tggaaatttc agcagcagcc ggaaggccag cagcattttc attggcattt tcagcagcag   120
```

<210> SEQ ID NO 41
<211> LENGTH: 39
<212> TYPE: PRT
<213> ORGANISM: artificial sequence
<220> FEATURE:
<223> OTHER INFORMATION: Synthetic construct. Inclusion body tag IBT183

<400> SEQUENCE: 41

```
Gln Gln His Phe His Trp His Phe Gln Gln Gln Pro Arg Gly Gln Gln
1               5                   10                  15

Lys Phe Lys Trp Lys Phe Gln Gln Gln Pro Glu Gly Gln Gln His Phe
            20                  25                  30

His Trp His Phe Gln Gln Gln
        35
```

<210> SEQ ID NO 42
<211> LENGTH: 120
<212> TYPE: DNA
<213> ORGANISM: artificial sequence
<220> FEATURE:
<223> OTHER INFORMATION: Synthetic construct. Nucleic acid sequence
      encoding inclusion body tag IBT184

<400> SEQUENCE: 42

```
atgcagcaga atttcattg cattttcag cagcagccgc gcggccagca gaaatttcat    60
tggcattttc agcagcagcc ggaaggccag cagaaatttc attggcattt tcagcagcag   120
```

<210> SEQ ID NO 43
<211> LENGTH: 39
<212> TYPE: PRT
<213> ORGANISM: artificial sequence
<220> FEATURE:

<223> OTHER INFORMATION: Synthetic construct. Inclusion body tag IBT184

<400> SEQUENCE: 43

Gln Gln Lys Phe His Trp His Phe Gln Gln Gln Pro Arg Gly Gln Gln
1               5                   10                  15

Lys Phe His Trp His Phe Gln Gln Gln Pro Glu Gly Gln Gln Lys Phe
            20                  25                  30

His Trp His Phe Gln Gln Gln
        35

<210> SEQ ID NO 44
<211> LENGTH: 144
<212> TYPE: DNA
<213> ORGANISM: artificial sequence
<220> FEATURE:
<223> OTHER INFORMATION: Synthetic construct. Nucleic acid sequence
      encoding inclusion body tag IBT185

<400> SEQUENCE: 44
atggctagcc cttgtggtca gcaacgtttc caatggcaat ttgaacagca gccttgcggt      60
caacagcgct tccagtggca gtttgaacag cagccatgcg gtcagcaacg ctttcagtgg     120
caatttgaac aacaaccgtg cggc                                            144

<210> SEQ ID NO 45
<211> LENGTH: 48
<212> TYPE: PRT
<213> ORGANISM: artificial sequence
<220> FEATURE:
<223> OTHER INFORMATION: Synthetic construct. Inclusion body tag IBT185

<400> SEQUENCE: 45

Met Ala Ser Pro Cys Gly Gln Gln Arg Phe Gln Trp Gln Phe Glu Gln
1               5                   10                  15

Gln Pro Cys Gly Gln Gln Arg Phe Gln Trp Gln Phe Glu Gln Gln Pro
            20                  25                  30

Cys Gly Gln Gln Arg Phe Gln Trp Gln Phe Glu Gln Gln Pro Cys Gly
        35                  40                  45

<210> SEQ ID NO 46
<211> LENGTH: 120
<212> TYPE: DNA
<213> ORGANISM: artificial sequence
<220> FEATURE:
<223> OTHER INFORMATION: Synthetic construct. Nucleic acid sequence
      encoding inclusion body tag IBT187a

<400> SEQUENCE: 46
atgcagcaga aatttaaatg gaaatttcag cagcagccgc gcggccagca gaaatttaaa      60
tggaaatttc agcagcagcc ggaaggccag cagaaattta atggaaatt tcagcagcag      120

<210> SEQ ID NO 47
<211> LENGTH: 39
<212> TYPE: PRT
<213> ORGANISM: artificial sequence
<220> FEATURE:
<223> OTHER INFORMATION: Synthetic construct. Inclusion body tag
      IBT187a

<400> SEQUENCE: 47

Gln Gln Lys Phe Lys Trp Lys Phe Gln Gln Gln Pro Arg Gly Gln Gln
1               5                   10                  15

Lys Phe Lys Trp Lys Phe Gln Gln Gln Pro Glu Gly Gln Gln Lys Phe

Lys Trp Lys Phe Gln Gln Gln
        35

<210> SEQ ID NO 48
<211> LENGTH: 162
<212> TYPE: DNA
<213> ORGANISM: artificial sequence
<220> FEATURE:
<223> OTHER INFORMATION: Synthetic construct. Nucleic acid sequence
      encoding inclusion body tag IBT187b

<400> SEQUENCE: 48
atgcagcaga aatttaaatg gaaatttcag cagcagccgc gcggccagca gaaatttaaa      60
tggaaatttc agcagcagcc gcgcggccag cagaaattta atggaaatt tcagcagcag     120 ccggaaggcc agcagaaatt taaatggaaa tttcagaagc ag                        162

<210> SEQ ID NO 49
<211> LENGTH: 53
<212> TYPE: PRT
<213> ORGANISM: artificial sequence
<220> FEATURE:
<223> OTHER INFORMATION: Synthetic construct. Inclusion body tag
      IBT187b

<400> SEQUENCE: 49

Gln Gln Lys Phe Lys Trp Lys Phe Gln Gln Gln Pro Arg Gly Gln Gln
1               5                   10                  15

Lys Phe Lys Trp Lys Phe Gln Gln Gln Pro Arg Gly Gln Gln Lys Phe
            20                  25                  30

Lys Trp Lys Phe Gln Gln Gln Pro Glu Gly Gln Gln Lys Phe Lys Trp
        35                  40                  45

Lys Phe Gln Lys Gln
    50

<210> SEQ ID NO 50
<211> LENGTH: 5214
<212> TYPE: DNA
<213> ORGANISM: artificial sequence
<220> FEATURE:
<223> OTHER INFORMATION: Plasmid

<400> SEQUENCE: 50
agatctcgat cccgcgaaat taatacgact cactataggg agaccacaac ggtttccctc      60
tagaaataat tttgtttaac tttaagaagg agatatacat atgcataccc agaacacat     120 caccgccgtg gtacagcgct tgtggctgc gctcaatgcc ggcgatctgg acggcatcgt     180
cgcgctgttt gccgatgacg ccacggtgga agagcccgtg ggttccgagc caggtccgg     240 tacggctgcg tgtcgtgagt tttacgccaa ctcgctcaaa ctgcctttgg cggtggagct     300
gacgcaggag tgccgcgcgg tcgccaacga agcggcttc gctttcaccg tcagcttcga     360
gtatcagggc cgcaagaccg tagttgcgcc ctgtgatcac tttcgcttca atggcgccgg     420
caaggtggtg agcatccgcg ccttgtttgg cgagaagaat attcacgcat gccagggatc     480
cgaccctggt atcccgtggt ggaacattcg cgcacctctg aatgctggtg ctggtattcc     540
gtggtggaac atccgtgctc ctctgaacgc gggtggctcc ggtccgggct ccggtggcaa     600
cacgagccaa ctgagcaccg tggtggcaa cacttcccag ctgtccaccg gcggtccgaa     660
aaagtaataa ggcgcgccga cccagctttc ttgtacaaag tggttgattc gaggctgcta     720

```
acaaagcccg aaaggaagct gagttggctg ctgccaccgc tgagcaataa ctagcataac    780
cccttggggc ctctaaacgg gtcttgaggg gttttttgct gaaaggagga actatatccg    840
gatatccaca ggacgggtgt ggtcgccatg atcgcgtagt cgatagtggc tccaagtagc    900
gaagcgagca ggactgggcg gcggccaaag cggtcggaca gtgctccgag aacgggtgcg    960
catagaaatt gcatcaacgc atatagcgct agcagcacgc catagtgact ggcgatgctg   1020
tcggaatgga cgatatcccg caagaggccc ggcagtaccg gcataaccaa gcctatgcct   1080
acagcatcca gggtgacggt gccgaggatg acgatgagcg cattgttaga tttcatacac   1140
ggtgcctgac tgcgttagca atttaactgt gataaactac cgcattaaag cttatcgatg   1200
ataagctgtc aaacatgaga attcttgaag acgaaagggc ctcgtgatac gcctattttt   1260
ataggttaat gtcatgataa taatggtttc ttagacgtca ggtggcactt ttcggggaaa   1320
tgtgcgcgga accctatttt gtttattttt ctaaatacat tcaaatatgt atccgctcat   1380
gagacaataa ccctgataaa tgcttcaata atattgaaaa aggaagagta tgagtattca   1440
acatttccgt gtcgccctta ttcccttttt tgcggcattt tgccttcctg ttttgctca    1500
cccagaaacg ctggtgaaag taaaagatgc tgaagatcag ttgggtgcac gagtgggtta   1560
catcgaactg gatctcaaca gcggtaagat ccttgagagt tttcgccccg aagaacgttt   1620
tccaatgatg agcacttta aagttctgct atgtggcgcg gtattatccc gtgttgacgc    1680
cgggcaagag caactcggtc gccgcataca ctattctcag aatgacttgg ttgagtactc   1740
accagtcaca gaaaagcatc ttacggatgg catgacagta agagaattat gcagtgctgc   1800
cataaccatg agtgataaca ctgcggccaa cttacttctg acaacgatcg gaggaccgaa   1860
ggagctaacc gcttttttgc acaacatggg ggatcatgta actcgccttg atcgttggga   1920
accggagctg aatgaagcca taccaaacga cgagcgtgac accacgatgc ctgcagcaat   1980
ggcaacaacg ttgcgcaaac tattaactgg cgaactactt actctagctt cccggcaaca   2040
attaatagac tggatggagg cggataaagt tgcaggacca cttctgcgct cggcccttcc   2100
ggctggctgg tttattgctg ataaatctgg agccggtgag cgtgggtctc gcggtatcat   2160
tgcagcactg gggccagatg gtaagccctc ccgtatcgta gttatctaca cgacggggag   2220
tcaggcaact atggatgaac gaaatagaca gatcgctgag ataggtgcct cactgattaa   2280
gcattggtaa ctgtcagacc aagtttactc atatatactt tagattgatt taaaacttca   2340
tttttaattt aaaaggatct aggtgaagat cctttttgat aatctcatga ccaaaatccc   2400
ttaacgtgag ttttcgttcc actgagcgtc agaccccgta gaaaagatca aggatcttc    2460
ttgagatcct ttttttctgc gcgtaatctg ctgcttgcaa acaaaaaaac caccgctacc   2520
agcggtggtt tgtttgccgg atcaagagct accaactctt tttccgaagg taactggctt   2580
cagcagagcg cagataccaa atactgtcct tctagtgtag ccgtagttag gccaccactt   2640
caagaactct gtagcaccgc ctacatacct cgctctgcta atcctgttac cagtggctgc   2700
tgccagtggc gataagtcgt gtcttaccgg gttggactca agacgatagt taccggataa   2760
ggcgcagcgg tcgggctgaa cggggggttc gtgcacacag cccagcttgg agcgaacgac   2820
ctacaccgaa ctgagatacc tacagcgtga gctatgagaa agcgccacgc ttcccgaagg   2880
gagaaaggcg gacaggtatc cggtaagcgg cagggtcgga acaggagagc gcacgaggga   2940
gcttccaggg ggaaacgcct ggtatcttta tagtcctgtc gggtttcgcc acctctgact   3000
tgagcgtcga tttttgtgat gctcgtcagg ggggcggagc ctatggaaaa acgccagcaa   3060
cgcggccttt ttacggttcc tggccttttg ctggcttttt gctcacatgt tctttcctgc   3120
```

```
gttatccctt gattctgtgg ataaccgtat taccgccttt gagtgagctg ataccgctcg    3180
ccgcagccga acgaccgagc gcagcgagtc agtgagcgag gaagcggaag agcgcctgat    3240
gcggtatttt ctccttacgc atctgtgcgg tatttcacac cgcatatatg gtgcactctc    3300
agtacaatct gctctgatgc cgcatagtta agccagtata cactccgcta tcgctacgtg    3360
actgggtcat ggctgcgccc cgacacccgc caacacccgc tgacgcgccc tgacgggctt    3420
gtctgctccc ggcatccgct tacagacaag ctgtgaccgt ctccgggagc tgcatgtgtc    3480
agaggttttc accgtcatca ccgaaacgcg cgaggcagct gcggtaaagc tcatcagcgt    3540
ggtcgtgaag cgattcacag atgtctgcct gttcatccgc gtccagctcg ttgagtttct    3600
ccagaagcgt taatgtctgg cttctgataa agcgggccat gttaagggcg gttttttcct    3660
gtttggtcac tgatgcctcc gtgtaagggg gatttctgtt catggggta atgataccga    3720 tgaaacgaga ggatgctc acgatacggg ttactgatga tgaacatgcc cggttactgg    3780
aacgttgtga gggtaaacaa ctggcggtat ggatgcggcg ggaccagaga aaaatcactc    3840
agggtcaatg ccagcgcttc gttaatacag atgtaggtgt tccacagggt agccagcagc    3900
atcctgcgat gcagatccgg aacataatgg tgcagggcgc tgacttccgc gtttccagac    3960
tttacgaaac acgaaaaccg aagaccattc atgttgttgc tcaggtcgca gacgttttgc    4020
agcagcagtc gcttcacgtt cgctcgcgta tcggtgattc attctgctaa ccagtaaggc    4080
aaccccgcca gcctagccgg gtcctcaacg acaggagcac gatcatgcgc acccgtggcc    4140
aggacccaac gctgcccgag atgcgccgcg tgcggctgct ggagatggcg gacgcgatgg    4200
atatgttctg ccaagggttg gtttgcgcat tcacagttct ccgcaagaat tgattggctc    4260
caattcttgg agtggtgaat ccgttagcga ggtgccgccg gcttccattc aggtcgaggt    4320
ggcccggctc catgcaccgc gacgcaacgc ggggaggcag acaaggtata gggcggcgcc    4380
tacaatccat gccaacccgt tccatgtgct cgccgaggcg gcataaatcg ccgtgacgat    4440
cagcggtcca gtgatcgaag ttaggctggt aagagccgcg agcgatcctt gaagctgtcc    4500
ctgatggtcg tcatctacct gcctggacag catggcctgc aacgcgggca tcccgatgcc    4560
gccggaagcg agaagaatca taatggggaa ggccatccag cctcgcgtcg cgaacgccag    4620
caagacgtag cccagcgcgt cggccgccat gccggcgata atggcctgct tctcgccgaa    4680
acgtttggtg gcgggaccag tgacgaaggc ttgagcgagg gcgtgcaaga ttccgaatac    4740
cgcaagcgac aggccgatca tcgtcgcgct ccagcgaaag cggtcctcgc cgaaaatgac    4800
ccagagcgct gccggcacct gtcctacgag ttgcatgata aagaagacag tcataagtgc    4860
ggcgacgata gtcatgcccc gcgcccaccg gaaggagctg actgggttga aggctctcaa    4920
gggcatcggt cgatcgacgc tctcccttat gcgactcctg cattaggaag cagcccagta    4980
gtaggttgag gccgttgagc accgccgccg caaggaatgg tgcatgcaag gagatggcgc    5040
ccaacagtcc cccggccacg gggcctgcca ccatacccac gccgaaacaa gcgctcatga    5100
gcccgaagtg gcgagcccga tcttccccat cggtgatgtc ggcgatatag gcgccagcaa    5160
ccgcacctgt ggcgccggtg atgccggcca cgatgcgtcc ggcgtagagg atcg          5214
```

<210> SEQ ID NO 51
<211> LENGTH: 6010
<212> TYPE: DNA
<213> ORGANISM: artificial sequence
<220> FEATURE:
<223> OTHER INFORMATION: Plasmid

<400> SEQUENCE: 51

```
aagaaaccaa ttgtccatat tgcatcagac attgccgtca ctgcgtcttt tactggctct     60
tctcgctaac caaaccggta accccgctta ttaaaagcat tctgtaacaa agcgggacca    120
aagccatgac aaaaacgcgt aacaaaagtg tctataatca cggcagaaaa gtccacattg    180
attatttgca cggcgtcaca ctttgctatg ccatagcatt tttatccata agattagcgg    240
atcttacctg acgcttttta tcgcaactct ctactgtttc tccatacccg ttttttgggc    300
taacaggagg aattacatat gcagcagcgt ttccagtggc agttcgaaca gcagccgcgt    360
ggtcagcagc gtttccagtg gcagttcgaa cagcagccgc gtggtcagca gcgtttccag    420
tggcagttcg aacagcagcc ggaaggtcag cagcgtttcc agtggcagtt cgaacagcag    480
ggatccgacc ctggcattcc gtggtggaac attcgtgctc ctctgaatgc aggtgcgggc    540
atcccttggt ggaatattcg tgctccgctg aacgccggtg gttccggtcc gggtagcggt    600
ggtaatactt ctcagctgtc cacgggtggc ggtaacacta gccagctgag cacgggcggc    660
cctaaaaagc cgggcgaccc gggtattccg tggtggaata ccgtgccccc gctgaacgca    720
ggtgccggca tcccgtggtg gaacattcgt gcacctctga atgctggtgg ttccggtcca    780
ggctctggcg gcaacacttc ccagctgtcc accggcggtg gcaacaccag ccagctgtct    840
actggtggtc cgaagaaacc gggtgactaa taaggcgcgc cgacccagct ttcttgtaca    900
aagtggttga ttcgaggctg ctaacaaagc ccgaaaggaa gctgagttgg ctgctgccac    960
cgctgagcaa taactagcat aacccccttgg ggcctctaaa cgggtcttga ggggttttt   1020
gctgaaagga ggaactatat ccggatatcc acaggacggg tgtggtcgcc atgatcgcgt   1080
agtcgatagt ggctccaagt agcgaagcga caggactgg cggcggcca aagcggtcgg   1140
acagtgctcc gagaacgggt gcgcatagaa attgcatcaa cgcatatagc gctagcagca   1200
cgccatagtg actggcgatg ctgtcggaat ggacgatatc ccgcaagagg cccggcagta   1260
ccggcataac caagcctatg cctacagcat ccagggtgac ggtgccgagg atgacgatga   1320
gcgcattgtt agatttcata cacggtgcct gactgcgtta gcaatttaac tgtgataaac   1380
taccgcatta aagcttgcag tggcggtttt catggcttgt tatgactgtt tttttgggt   1440
acagtctatg cctcgggcat ccaagcagca agcgcgttac gccgtgggtc gatgtttgat   1500
gttatggagc agcaacgatg ttacgcagca gggcagtcgc cctaaaacaa agttaaacat   1560
catgagggaa gcggtgatcg ccgaagtatc gactcaacta tcagaggtag ttggcgtcat   1620
cgagcgccat ctcgaaccga cgttgctggc cgtacatttg tacggctccg cagtggatgg   1680
cggcctgaag ccacacagtg atattgattt gctggttacg gtgaccgtaa ggcttgatga   1740
aacaacgcgg cgagctttga tcaacgacct tttggaaact tcggcttccc ctggagagag   1800
cgagattctc cgcgctgtag aagtcaccat tgttgtgcac gacgacatca ttccgtggcg   1860
ttatccagct aagcgcgaac tgcaatttgg agaatggcag cgcaatgaca ttcttgcagg   1920
tatcttcgag ccagccacga tcgacattga tctggctatc ttgctgacaa agcaagaga   1980
acatagcgtt gccttggtag gtccagcggc ggaggaactc tttgatccgg ttcctgaaca   2040
ggatctattt gaggcgctaa atgaaacctt aacgctatgg aactcgccgc ccgactgggc   2100
tggcgatgag cgaaatgtag tgcttacgtt gtcccgcatt tggtacagcg cagtaaccgg   2160
caaaatcgcg ccgaaggatg tcgctgccga ctgggcaatg gagcgcctgc cggcccagta   2220
tcagcccgtc atacttgaag ctagacaggc ttatcttgga caagaagaag atcgcttggc   2280
ctcgcgcgca gatcagttgg aagaatttgt ccactacgtg aaaggcgaga tcaccaaggt   2340
```

```
agtcggcaaa taatgtctaa caattcgttc aagcttggct gttttggcgg atgagagaag    2400
attttcagcc tgatacagat taaatcagaa cgcagaagcg gtctgataaa acagaatttg    2460
cctggcggca gtagcgcggt ggtcccacct gaccccatgc cgaactcaga agtgaaacgc    2520
cgtagcgccg atggtagtgt ggggtctccc catgcgagag tagggaactg ccaggcatca    2580
aataaaacga aaggctcagt cgaaagactg ggcctttcgt tttatctgtt gtttgtcggt    2640
gaacgctctc ctgagtagga caaatccgcc gggagcggat ttgaacgttg cgaagcaacg    2700
gcccggaggg tggcgggcag gacgcccgcc ataaactgcc aggcatcaaa ttaagcagaa    2760
ggccatcctg acggatggcc ttttgcgtt tctacaaact cttttgttta tttttctaaa     2820
tacattcaaa tatgtatccg ctcatgagac aataaccctg ataaatgctt caataatatt    2880 gaaaaggaa gagtatgagt attcaacatt tccgtgtcgc ccttattccc ttttttgcgg     2940
cattttgcct tcctgttttt gctcacccag aaacgctggt gaaagtaaaa gatgctgaag    3000
atcagttggg tgcacgagtg ggttacatcg aactggatct caacagcggt aagatccttg    3060
agagttttcg ccccgaagaa cgttttccaa tgatgagcac ttttaaagtt ctgctatgtg    3120
gcgcggtatt atcccgtgtt gacgccgggc aagagcaact cggtcgccgc atacactatt    3180
ctcagaatga cttggttgag tactcaccag tcacagaaaa gcatcttacg gatggcatga    3240
cagtaagaga attatgcagt gctgccataa ccatgagtga taacactgcg gccaacttac    3300
ttctgacaac gatcggagga ccgaaggagc taaccgcttt tttgcacaac atgggggatc    3360
atgtaactcg ccttgatcgt tgggaaccgg agctgaatga agccatacca aacgacgagc    3420
gtgacaccac gatgcctgta gcaatggcaa caacgttgcg caaactatta actggcgaac    3480
tacttactct agcttcccgg caacaattaa tagactggga ggaggcggat aaagttgcag    3540
gaccacttct gcgctcggcc cttccggctg gctggtttat tgctgataaa tctggagccg    3600
gtgagcgtgg gtctcgcggt atcattgcag cactggggcc agatggtaag ccctcccgta    3660
tcgtagttat ctacacgacg gggagtcagg caactatgga tgaacgaaat agacagatcg    3720
ctgagatagg tgcctcactg attaagcatt ggtaactgtc agaccaagtt tactcatata    3780
tactttagat tgatttaaaa cttcattttt aatttaaaag gatctaggtg aagatccttt    3840
ttgataatct catgaccaaa atcccttaac gtgagttttc gttccactga gcgtcagacc    3900
ccgtagaaaa gatcaaagga tcttcttgag atcctttttt tctgcgcgta atctgctgct    3960
tgcaaacaaa aaaaccaccg ctaccagcgg tggtttgttt gccggatcaa gagctaccaa    4020
ctctttttcc gaaggtaact ggcttcagca gagcgcagat accaaatact gtccttctag    4080
tgtagccgta gttaggccac cacttcaaga actctgtagc accgcctaca tacctcgctc    4140
tgctaatcct gttaccagtg gctgctgcca gtggcgataa gtcgtgtctt accgggttgg    4200
actcaagacg atagttaccg gataaggcgc agcggtcggg ctgaacgggg gttcgtgca    4260 cacagcccag cttggagcga acgacctaca ccgaactgag atacctacag cgtgagctat    4320
gagaaagcgc cacgcttccc gaagggagaa aggcggacag gtatccggta agcggcaggg    4380
tcggaacagg agagcgcacg agggagcttc caggggggaaa cgcctggtat ctttatagtc    4440
ctgtcgggtt tcgccacctc tgacttgagc gtcgattttt gtgatgctcg tcagggggggc   4500 ggagcctatg gaaaaacgcc agcaacgcgg ccttttttacg gttcctggcc ttttgctggc    4560
cttttgctca catgttcttt cctgcgttat cccctgattc tgtggataac cgtattaccg    4620
cctttgagtg agctgatacc gctcgccgca gccgaacgac cgagcgcagc gagtcagtga    4680
```

-continued

```
gcgaggaagc ggaagagcgc ctgatgcggt attttctcct tacgcatctg tgcggtattt        4740
cacaccgcat atatggtgca ctctcagtac aatctgctct gatgccgcat agttaagcca        4800
gtatacactc cgctatcgct acgtgactgg gtcatggctg cgccccgaca cccgccaaca        4860
cccgctgacg cgccctgacg ggcttgtctg ctcccggcat ccgcttacag acaagctgtg        4920
accgtctccg ggagctgcat gtgtcagagg ttttcaccgt catcaccgaa acgcgcgagg        4980
cagcagatca attcgcgcgc gaaggcgaag cggcatgcat aatgtgcctg tcaaatggac        5040
gaagcaggga ttctgcaaac cctatgctac tccgtcaagc cgtcaattgt ctgattcgtt        5100
accaattatg caacttgacg gctacatca ttcactttt cttcacaacc ggcacggaac         5160
tcgctcgggc tggccccggt gcatttttta aatacccgcg agaaatagag ttgatcgtca        5220
aaaccaacat tgcgaccgac ggtggcgata ggcatccggg tggtgctcaa aagcagcttc        5280
gcctggctga tacgttggtc ctcgcgccag cttaagacgc taatccctaa ctgctggcgg        5340
aaaagatgtg acagacgcga cggcgacaag caaacatgct gtgcgacgct ggcgatatca        5400
aaattgctgt ctgccaggtg atcgctgatg tactgacaag cctcgcgtac ccgattatcc        5460
atcggtggat ggagcgactc gttaatcgct tccatgcgcc gcagtaacaa ttgctcaagc        5520
agatttatcg ccagcagctc cgaatagcgc ccttcccctt gcccggcgtt aatgatttgc        5580
ccaaacaggt cgctgaaatg cggctggtgc gcttcatccg ggcgaaagaa ccccgtattg        5640
gcaaatattg acggccagtt aagccattca tgccagtagg cgcgcggacg aaagtaaacc        5700
cactggtgat accattcgcg agcctccgga tgacgaccgt agtgatgaat ctctcctggc        5760
gggaacagca aaatatcacc cggtcggcaa acaaattctc gtccctgatt tttcaccacc        5820
ccctgaccgc gaatggtgag attgagaata aaccttcca ttcccagcgg tcggtcgata        5880
aaaaaatcga gataaccgtt ggcctcaatc ggcgttaaac ccgccaccag atgggcatta       5940
aacgagtatc ccggcagcag gggatcattt tgcgcttcag ccatactttt catactcccg        6000
ccattcagag                                                              6010
```

<210> SEQ ID NO 52
<211> LENGTH: 381
<212> TYPE: DNA
<213> ORGANISM: artificial sequence
<220> FEATURE:
<223> OTHER INFORMATION: Synthetic construct. Nucleic acid sequence encoding KSI(C4)

<400> SEQUENCE: 52

```
atgcataccc cagaacacat caccgccgtg gtacagcgct tgtggctgc gctcaatgcc           60 ggcgatctgg acggcatcgt cgcgctgttt gccgatgacg ccacggtgga agagcccgtg         120
ggttccgagc ccaggtccgg tacggctgcg tgtcgtgagt tttacgccaa ctcgctcaaa         180
ctgcctttgg cggtggagct gacgcaggag tgccgcgcgg tcgccaacga agcggccttc         240
gctttcaccg tcagcttcga gtatcagggc cgcaagaccg tagttgcgcc ctgtgatcac         300
tttcgcttca atggcgccgg caaggtggtg agcatccgcg ccttgtttgg cgagaagaat         360
attcacgcat gccagggatc c                                                 381
```

<210> SEQ ID NO 53
<211> LENGTH: 125
<212> TYPE: PRT
<213> ORGANISM: artificial sequence
<220> FEATURE:
<223> OTHER INFORMATION: Synthetic construct. KSI(C4)

-continued

<400> SEQUENCE: 53

Met His Thr Pro Glu His Ile Thr Ala Val Val Gln Arg Phe Val Ala
1               5                   10                  15

Ala Leu Asn Ala Gly Asp Leu Asp Gly Ile Val Ala Leu Phe Ala Asp
            20                  25                  30

Asp Ala Thr Val Glu Glu Pro Val Gly Ser Glu Pro Arg Ser Gly Thr
        35                  40                  45

Ala Ala Cys Arg Glu Phe Tyr Ala Asn Ser Leu Lys Leu Pro Leu Ala
    50                  55                  60

Val Glu Leu Thr Gln Glu Cys Arg Ala Val Ala Asn Glu Ala Ala Phe
65                  70                  75                  80

Ala Phe Thr Val Ser Phe Glu Tyr Gln Gly Arg Lys Thr Val Val Ala
                85                  90                  95

Pro Cys Asp His Phe Arg Phe Asn Gly Ala Gly Lys Val Val Ser Ile
            100                 105                 110

Arg Ala Leu Phe Gly Glu Lys Asn Ile His Ala Cys Gln
        115                 120                 125

<210> SEQ ID NO 54
<211> LENGTH: 570
<212> TYPE: DNA
<213> ORGANISM: artificial sequence
<220> FEATURE:
<223> OTHER INFORMATION: Synthetic construct. Chimeric gene encoding
      fusion peptide KSI(C4)-HC77643

<400> SEQUENCE: 54
atgcataccc cagaacacat caccgccgtg gtacagcgct ttgtggctgc gctcaatgcc      60
ggcgatctgg acggcatcgt cgcgctgttt gccgatgacg ccacggtgga agagcccgtg    120
ggttccgagc ccaggtccgg tacggctgcg tgtcgtgagt tttacgccaa ctcgctcaaa    180
ctgcctttgg cggtggagct gacgcaggag tgccgcgcgg tcgccaacga agcggccttc    240
gctttcaccg tcagcttcga gtatcagggc cgcaagaccg tagttgcgcc ctgtgatcac    300
tttcgcttca atggcgccgg caaggtggtg agcatccgcg ccttgtttgg cgagaagaat    360
attcacgcat gccagggatc cgaccctggt atcccgtggt ggaacattcg cgcacctctg    420
aatgctggtg ctggtattcc gtggtggaac atccgtgctc ctctgaacgc gggtggctcc    480
ggtccgggct ccggtggcaa cacgagccaa ctgagcaccg tggtggcaa cacttcccag    540 ctgtccaccg gcggtccgaa aaagtaataa                                     570

<210> SEQ ID NO 55
<211> LENGTH: 188
<212> TYPE: PRT
<213> ORGANISM: artificial sequence
<220> FEATURE:
<223> OTHER INFORMATION: Synthetic construct. Fusion peptide
      KSI(C4)-HC77643

<400> SEQUENCE: 55

Met His Thr Pro Glu His Ile Thr Ala Val Val Gln Arg Phe Val Ala
1               5                   10                  15

Ala Leu Asn Ala Gly Asp Leu Asp Gly Ile Val Ala Leu Phe Ala Asp
            20                  25                  30

Asp Ala Thr Val Glu Glu Pro Val Gly Ser Glu Pro Arg Ser Gly Thr
        35                  40                  45

Ala Ala Cys Arg Glu Phe Tyr Ala Asn Ser Leu Lys Leu Pro Leu Ala
    50                  55                  60

```
Val Glu Leu Thr Gln Glu Cys Arg Ala Val Ala Asn Glu Ala Ala Phe
 65                  70                  75                  80

Ala Phe Thr Val Ser Phe Glu Tyr Gln Gly Arg Lys Thr Val Ala
                 85                  90                  95

Pro Cys Asp His Phe Arg Phe Asn Gly Ala Gly Lys Val Val Ser Ile
                100                 105                 110

Arg Ala Leu Phe Gly Lys Asn Ile His Ala Cys Gln Gly Ser Asp
            115                 120                 125

Pro Gly Ile Pro Trp Trp Asn Ile Arg Ala Pro Leu Asn Ala Gly Ala
            130                 135                 140

Gly Ile Pro Trp Trp Asn Ile Arg Ala Pro Leu Asn Ala Gly Ser
145                 150                 155                 160

Gly Pro Gly Ser Gly Gly Asn Thr Ser Gln Leu Ser Thr Gly Gly
                165                 170                 175

Asn Thr Ser Gln Leu Ser Thr Gly Gly Pro Lys Lys
            180                 185

<210> SEQ ID NO 56
<211> LENGTH: 4
<212> TYPE: PRT
<213> ORGANISM: artificial sequence
<220> FEATURE:
<223> OTHER INFORMATION: Synthetic construct. Spacer

<400> SEQUENCE: 56

Pro Arg Cys Gly
1

<210> SEQ ID NO 57
<211> LENGTH: 4
<212> TYPE: PRT
<213> ORGANISM: artificial sequence
<220> FEATURE:
<223> OTHER INFORMATION: Synthetic construct. Spacer

<400> SEQUENCE: 57

Pro Glu Cys Gly
1

<210> SEQ ID NO 58
<211> LENGTH: 11
<212> TYPE: PRT
<213> ORGANISM: artificial sequence
<220> FEATURE:
<223> OTHER INFORMATION: Synthetic Construct. Repeated Core Sequence
<220> FEATURE:
<221> NAME/KEY: MISC_FEATURE
<222> LOCATION: (3)..(3)
<223> OTHER INFORMATION: Xaa = Arg, His, or Lys
<220> FEATURE:
<221> NAME/KEY: MISC_FEATURE
<222> LOCATION: (5)..(5)
<223> OTHER INFORMATION: Xaa = Gln, His, or Lys
<220> FEATURE:
<221> NAME/KEY: MISC_FEATURE
<222> LOCATION: (7)..(7)
<223> OTHER INFORMATION: Xaa = Gln, His, or Lys
<220> FEATURE:
<221> NAME/KEY: MISC_FEATURE
<222> LOCATION: (9)..(9)
<223> OTHER INFORMATION: Xaa = Glu or Gln
<220> FEATURE:
<221> NAME/KEY: MISC_FEATURE
<222> LOCATION: (10)..(10)
<223> OTHER INFORMATION: Xaa = Gln or Lys
```

```
<400> SEQUENCE: 58

Gln Gln Xaa Phe Xaa Trp Xaa Phe Xaa Xaa Gln
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 59

Tyr Pro Ser Phe Ser Pro Thr Tyr Arg Pro Ala Phe
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 60

Ala Leu Pro Arg Ile Ala Asn Thr Trp Ser Pro Ser
1               5                   10

<210> SEQ ID NO 61
<211> LENGTH: 8
<212> TYPE: PRT
<213> ORGANISM: Artificial Sequence
<220> FEATURE:
<223> OTHER INFORMATION: Hair Binding Peptide Domain

<400> SEQUENCE: 61

Leu Glu Ser Thr Pro Lys Met Lys
1               5

<210> SEQ ID NO 62
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 62

Ser Val Ser Val Gly Met Lys Pro Ser Pro Arg Pro
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 63

Leu Asp Val Glu Ser Tyr Lys Gly Thr Ser Met Pro
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 64
```

Arg Val Pro Asn Lys Thr Val Thr Val Asp Gly Ala
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 65

Asp Arg His Lys Ser Lys Tyr Ser Ser Thr Lys Ser
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 66

Lys Asn Phe Pro Gln Gln Lys Glu Phe Pro Leu Ser
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 67

Gln Arg Asn Ser Pro Pro Ala Met Ser Arg Arg Asp
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 68

Thr Arg Lys Pro Asn Met Pro His Gly Gln Tyr Leu
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 69

Lys Pro Pro His Leu Ala Lys Leu Pro Phe Thr Thr
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 70

```
Asn Lys Arg Pro Pro Thr Ser His Arg Ile His Ala
1               5                   10
```

<210> SEQ ID NO 71
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 71

```
Asn Leu Pro Arg Tyr Gln Pro Pro Cys Lys Pro Leu
1               5                   10
```

<210> SEQ ID NO 72
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 72

```
Arg Pro Pro Trp Lys Lys Pro Ile Pro Pro Ser Glu
1               5                   10
```

<210> SEQ ID NO 73
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 73

```
Arg Gln Arg Pro Lys Asp His Phe Phe Ser Arg Pro
1               5                   10
```

<210> SEQ ID NO 74
<211> LENGTH: 12
<212> TYPE: PRT
<213> ORGANISM: Artificial Sequence
<220> FEATURE:
<223> OTHER INFORMATION: Hair Binding Peptide Domain
<220> FEATURE:
<221> NAME/KEY: MISC_FEATURE
<222> LOCATION: (6)..(6)
<223> OTHER INFORMATION: X= T or P
<220> FEATURE:
<221> NAME/KEY: MISC_FEATURE
<222> LOCATION: (12)..(12)
<223> OTHER INFORMATION: X= E or A

<400> SEQUENCE: 74

```
Ser Val Pro Asn Lys Xaa Val Thr Val Asp Gly Xaa
1               5                   10
```

<210> SEQ ID NO 75
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 75

```
Thr Thr Lys Trp Arg His Arg Ala Pro Val Ser Pro
1               5                   10
```

<210> SEQ ID NO 76
<211> LENGTH: 12

<212> TYPE: PRT
<213> ORGANISM: Artificial Sequence
<220> FEATURE:
<223> OTHER INFORMATION: Hair Binding Peptide Domain

<400> SEQUENCE: 76

Trp Leu Gly Lys Asn Arg Ile Lys Pro Arg Ala Ser
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 77

Ser Asn Phe Lys Thr Pro Leu Pro Leu Thr Gln Ser
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 78

Lys Glu Leu Gln Thr Arg Asn Val Val Gln Arg Glu
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 79

Gly Met Pro Ala Met His Trp Ile His Pro Phe Ala
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 80

Thr Pro Thr Ala Asn Gln Phe Thr Gln Ser Val Pro
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 81

Ala Ala Gly Leu Ser Gln Lys His Glu Arg Asn Arg
1               5                   10

<210> SEQ ID NO 82
<211> LENGTH: 12
<212> TYPE: PRT

```
<213> ORGANISM: Artificial Sequence
<220> FEATURE:
<223> OTHER INFORMATION: Hair Binding Peptide Domain

<400> SEQUENCE: 82

Glu Thr Val His Gln Thr Pro Leu Ser Asp Arg Pro
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 83

Leu Pro Ala Leu His Ile Gln Arg His Pro Arg Met
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 84

Gln Pro Ser His Ser Gln Ser His Asn Leu Arg Ser
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 85

Arg Gly Ser Gln Lys Ser Lys Pro Pro Arg Pro Pro
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 86

Thr His Thr Gln Lys Thr Pro Leu Leu Tyr Tyr His
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 87

Thr Lys Gly Ser Ser Gln Ala Ile Leu Lys Ser Thr
1               5                   10

<210> SEQ ID NO 88
<211> LENGTH: 7
<212> TYPE: PRT
<213> ORGANISM: Artificial Sequence
```

```
<220> FEATURE:
<223> OTHER INFORMATION: Hair Binding Peptide Domain

<400> SEQUENCE: 88

Asp Leu His Thr Val Tyr His
1               5

<210> SEQ ID NO 89
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 89

His Ile Lys Pro Pro Thr Arg
1               5

<210> SEQ ID NO 90
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 90

His Pro Val Trp Pro Ala Ile
1               5

<210> SEQ ID NO 91
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 91

Met Pro Leu Tyr Tyr Leu Gln
1               5

<210> SEQ ID NO 92
<211> LENGTH: 26
<212> TYPE: PRT
<213> ORGANISM: Artificial Sequence
<220> FEATURE:
<223> OTHER INFORMATION: Hair Binding Peptide Domain

<400> SEQUENCE: 92

His Leu Thr Val Pro Trp Arg Gly Gly Gly Ser Ala Val Pro Phe Tyr
1               5                   10                  15
Ser His Ser Gln Ile Thr Leu Pro Asn His
            20                  25

<210> SEQ ID NO 93
<211> LENGTH: 41
<212> TYPE: PRT
<213> ORGANISM: Artificial Sequence
<220> FEATURE:
<223> OTHER INFORMATION: Hair Binding Peptide Domain

<400> SEQUENCE: 93

Gly Pro His Asp Thr Ser Ser Gly Gly Val Arg Pro Asn Leu His His
1               5                   10                  15
Thr Ser Lys Lys Glu Lys Arg Glu Asn Arg Lys Val Pro Phe Tyr Ser
            20                  25                  30
```

His Ser Val Thr Ser Arg Gly Asn Val
        35                  40

<210> SEQ ID NO 94
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 94

Lys His Pro Thr Tyr Arg Gln
1               5

<210> SEQ ID NO 95
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 95

His Pro Met Ser Ala Pro Arg
1               5

<210> SEQ ID NO 96
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 96

Met Pro Lys Tyr Tyr Leu Gln
1               5

<210> SEQ ID NO 97
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 97

Met His Ala His Ser Ile Ala
1               5

<210> SEQ ID NO 98
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 98

Thr Ala Ala Thr Thr Ser Pro
1               5

<210> SEQ ID NO 99
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 99

Leu Gly Ile Pro Gln Asn Leu

```
<210> SEQ ID NO 100
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 100

Ala Lys Pro Ile Ser Gln His Leu Gln Arg Gly Ser
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 101

Ala Pro Pro Thr Pro Ala Ala Ala Ser Ala Thr Thr
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 102

Asp Pro Thr Glu Gly Ala Arg Arg Thr Ile Met Thr
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 103

Glu Gln Ile Ser Gly Ser Leu Val Ala Ala Pro Trp
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 104

Leu Asp Thr Ser Phe Pro Pro Val Pro Phe His Ala
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Hair Binding Peptide Domain

<400> SEQUENCE: 105

Leu Pro Arg Ile Ala Asn Thr Trp Ser Pro Ser
1               5                   10
```

```
<210> SEQ ID NO 106
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 106

Arg Thr Asn Ala Ala Asp His Pro Ala Ala Val Thr
1               5                   10

<210> SEQ ID NO 107
<211> LENGTH: 12
<212> TYPE: PRT
<213> ORGANISM: Artificial Sequence
<220> FEATURE:
<223> OTHER INFORMATION: HairBinding Peptide Domain

<400> SEQUENCE: 107

Ser Leu Asn Trp Val Thr Ile Pro Gly Pro Lys Ile
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 108

Thr Asp Met Gln Ala Pro Thr Lys Ser Tyr Ser Asn
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 109

Thr Ile Met Thr Lys Ser Pro Ser Leu Ser Cys Gly
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 110

Thr Pro Ala Leu Asp Gly Leu Arg Gln Pro Leu Arg
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 111

Thr Tyr Pro Ala Ser Arg Leu Pro Leu Leu Ala Pro
1               5                   10
```

<210> SEQ ID NO 112
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 112

Thr Tyr Pro Ala Ser Arg Leu Pro Leu Leu Ala Pro
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 113

Thr Asp Pro Thr Pro Phe Ser Ile Ser Pro Glu Arg
1               5                   10

<210> SEQ ID NO 114
<211> LENGTH: 20
<212> TYPE: PRT
<213> ORGANISM: Artificial Sequence
<220> FEATURE:
<223> OTHER INFORMATION: Hair Binding Peptide Domain

<400> SEQUENCE: 114

Cys Ala Ala Gly Cys Cys Thr Cys Ala Gly Cys Gly Ala Cys Cys Gly
1               5                   10                  15

Ala Ala Thr Ala
            20

<210> SEQ ID NO 115
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 115

Trp His Asp Lys Pro Gln Asn Ser Ser Lys Ser Thr
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 116

Asn Glu Val Pro Ala Arg Asn Ala Pro Trp Leu Val
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Hair Binding Peptide Domain

<400> SEQUENCE: 117

Asn Ser Pro Gly Tyr Gln Ala Asp Ser Val Ala Ile Gly

-continued

```
<210> SEQ ID NO 118
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 118

Thr Gln Asp Ser Ala Gln Lys Ser Pro Ser Pro Leu
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 119

Thr Pro Pro Glu Leu Leu His Gly Asp Pro Arg Ser
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 120

Thr Pro Pro Thr Asn Val Leu Met Leu Ala Thr Lys
1               5                   10

<210> SEQ ID NO 121
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 121

Asn Thr Pro Lys Glu Asn Trp
1               5

<210> SEQ ID NO 122
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 122

Asn Thr Pro Ala Ser Asn Arg
1               5

<210> SEQ ID NO 123
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 123

Pro Arg Gly Met Leu Ser Thr
1               5
```

<210> SEQ ID NO 124
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 124

Pro Pro Thr Tyr Leu Ser Thr
1               5

<210> SEQ ID NO 125
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 125

Thr Ile Pro Thr His Arg Gln His Asp Tyr Arg Ser
1               5                   10

<210> SEQ ID NO 126
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 126

Thr Pro Pro Thr His Arg Leu
1               5

<210> SEQ ID NO 127
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 127

Leu Pro Thr Met Ser Thr Pro
1               5

<210> SEQ ID NO 128
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 128

Leu Gly Thr Asn Ser Thr Pro
1               5

<210> SEQ ID NO 129
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 129

Thr Pro Leu Thr Gly Ser Thr Asn Leu Leu Ser Ser
1               5                   10

```
<210> SEQ ID NO 130
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 130

Thr Pro Leu Thr Lys Glu Thr
1               5

<210> SEQ ID NO 131
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 131

Gln Gln Ser His Asn Pro Pro
1               5

<210> SEQ ID NO 132
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 132

Thr Gln Pro His Asn Pro Pro
1               5

<210> SEQ ID NO 133
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 133

Ser Thr Asn Leu Leu Arg Thr Ser Thr Val His Pro
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 134

His Thr Gln Pro Ser Tyr Ser Ser Thr Asn Leu Phe
1               5                   10

<210> SEQ ID NO 135
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 135

Ser Leu Leu Ser Ser His Ala
1               5
```

```
<210> SEQ ID NO 136
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 136

Gln Gln Ser Ser Ile Ser Leu Ser Ser His Ala Val
1               5                   10

<210> SEQ ID NO 137
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 137

Asn Ala Ser Pro Ser Ser Leu
1               5

<210> SEQ ID NO 138
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 138

His Ser Pro Ser Ser Leu Arg
1               5

<210> SEQ ID NO 139
<211> LENGTH: 7
<212> TYPE: PRT
<213> ORGANISM: Artificial Sequence
<220> FEATURE:
<223> OTHER INFORMATION: Hair Binding Peptide Domain
<220> FEATURE:
<221> NAME/KEY: MISC_FEATURE
<222> LOCATION: (2)..(2)
<223> OTHER INFORMATION: X= H, R or N

<400> SEQUENCE: 139

Lys Xaa Ser His His Thr His
1               5

<210> SEQ ID NO 140
<211> LENGTH: 7
<212> TYPE: PRT
<213> ORGANISM: Artificial Sequence
<220> FEATURE:
<223> OTHER INFORMATION: Hair Binding Peptide Domain
<220> FEATURE:
<221> NAME/KEY: MISC_FEATURE
<222> LOCATION: (2)..(2)
<223> OTHER INFORMATION: X=H or Ror N
<220> FEATURE:
<221> NAME/KEY: MISC_FEATURE
<222> LOCATION: (2)..(2)
<223> OTHER INFORMATION: X= H, R, or N

<400> SEQUENCE: 140

Glu Xaa Ser His His Thr His
1               5

<210> SEQ ID NO 141
<211> LENGTH: 7
```

```
<212> TYPE: PRT
<213> ORGANISM: Artificial Sequence
<220> FEATURE:
<223> OTHER INFORMATION: Hair Binding Peptide Domain

<400> SEQUENCE: 141

Leu Glu Ser Thr Ser Leu Leu
1               5

<210> SEQ ID NO 142
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 142

Thr Pro Leu Thr Lys Glu Thr
1               5

<210> SEQ ID NO 143
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 143

Lys Gln Ser His Asn Pro Pro
1               5

<210> SEQ ID NO 144
<211> LENGTH: 15
<212> TYPE: PRT
<213> ORGANISM: Artificial Sequence
<220> FEATURE:
<223> OTHER INFORMATION: Hair-binding peptide

<400> SEQUENCE: 144

Ser Thr Leu His Lys Tyr Lys Ser Gln Asp Pro Thr Pro His His
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: Hair-binding peptide

<400> SEQUENCE: 145

His Asp His Lys Asn Gln Lys Glu Thr His Gln Arg His Ala Ala
1               5                   10                  15

<210> SEQ ID NO 146
<211> LENGTH: 20
<212> TYPE: PRT
<213> ORGANISM: Artificial Sequence
<220> FEATURE:
<223> OTHER INFORMATION: Hair-binding peptide

<400> SEQUENCE: 146

His Asn His Met Gln Glu Arg Tyr Thr Asp Pro Gln His Ser Pro Ser
1               5                   10                  15

Val Asn Gly Leu
            20
```

```
<210> SEQ ID NO 147
<211> LENGTH: 20
<212> TYPE: PRT
<213> ORGANISM: Artificial Sequence
<220> FEATURE:
<223> OTHER INFORMATION: Hair-binding peptide

<400> SEQUENCE: 147

Thr Ala Glu Ile Asp Ser Ser Lys Asn Pro Asn Pro His Pro Gln Arg
1               5                   10                  15

Ser Trp Thr Asn
            20

<210> SEQ ID NO 148
<211> LENGTH: 7
<212> TYPE: PRT
<213> ORGANISM: Artificial sequence
<220> FEATURE:
<223> OTHER INFORMATION: Skin Binding Peptide Domain

<400> SEQUENCE: 148

Phe Thr Gln Ser Leu Pro Arg
1               5

<210> SEQ ID NO 149
<211> LENGTH: 12
<212> TYPE: PRT
<213> ORGANISM: Artificial Sequence
<220> FEATURE:
<223> OTHER INFORMATION: Skin Binding Peptide Domain

<400> SEQUENCE: 149

Thr Pro Phe His Ser Pro Glu Asn Ala Pro Gly Ser
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Skin Binding Peptide Domain

<400> SEQUENCE: 150

Lys Gln Ala Thr Phe Pro Pro Asn Pro Thr Ala Tyr
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Skin Binding Peptide Domain

<400> SEQUENCE: 151

His Gly His Met Val Ser Thr Ser Gln Leu Ser Ile
1               5                   10

<210> SEQ ID NO 152
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 152

Leu Ser Pro Ser Arg Met Lys
1               5
```

```
<210> SEQ ID NO 153
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 153

Leu Pro Ile Pro Arg Met Lys
1               5

<210> SEQ ID NO 154
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 154

His Gln Arg Pro Tyr Leu Thr
1               5

<210> SEQ ID NO 155
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 155

Phe Pro Pro Leu Leu Arg Leu
1               5

<210> SEQ ID NO 156
<211> LENGTH: 12
<212> TYPE: PRT
<213> ORGANISM: Artificial Sequence
<220> FEATURE:
<223> OTHER INFORMATION: Nail Binding Peptide Domain

<400> SEQUENCE: 156

Ala Leu Pro Arg Ile Ala Asn Thr Trp Ser Pro Ser
1               5                   10

<210> SEQ ID NO 157
<211> LENGTH: 12
<212> TYPE: PRT
<213> ORGANISM: Artificial Sequence
<220> FEATURE:
<223> OTHER INFORMATION: Nail Binding Peptide Domain

<400> SEQUENCE: 157

Tyr Pro Ser Phe Ser Pro Thr Tyr Arg Pro Ala Phe
1               5                   10

<210> SEQ ID NO 158
<211> LENGTH: 17
<212> TYPE: PRT
<213> ORGANISM: Artificial sequence
<220> FEATURE:
<223> OTHER INFORMATION: antimicrobial peptide sequence

<400> SEQUENCE: 158

Pro Lys Gly Leu Lys Lys Leu Leu Lys Gly Leu Lys Lys Leu Leu Lys
1               5                   10                  15
```

Leu

<210> SEQ ID NO 159
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 159

```
Lys Gly Leu Lys Lys Leu Leu Lys Gly Leu Lys Lys Leu Leu Lys Leu
1               5                   10                  15
```

<210> SEQ ID NO 160
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 160

```
Lys Gly Leu Lys Lys Leu Leu Lys Leu Leu Lys Lys Leu Leu Lys Leu
1               5                   10                  15
```

<210> SEQ ID NO 161
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 161

```
Leu Lys Lys Leu Leu Lys Leu Leu Lys Lys Leu Leu Lys Leu
1               5                   10
```

<210> SEQ ID NO 162
<211> LENGTH: 12
<212> TYPE: PRT
<213> ORGANISM: Artificial Sequence
<220> FEATURE:
<223> OTHER INFORMATION: Antimicrobial peptide sequence

<400> SEQUENCE: 162

```
Leu Lys Lys Leu Leu Lys Leu Leu Lys Lys Leu Leu
1               5                   10
```

<210> SEQ ID NO 163
<211> LENGTH: 17
<212> TYPE: PRT
<213> ORGANISM: Artificial Sequence
<220> FEATURE:
<223> OTHER INFORMATION: Antimicrobial peptide sequences

<400> SEQUENCE: 163

```
Val Ala Lys Lys Leu Ala Lys Leu Ala Lys Lys Leu Ala Lys Leu Ala
1               5                   10                  15
Leu
```

<210> SEQ ID NO 164
<211> LENGTH: 13
<212> TYPE: PRT
<213> ORGANISM: Artificial Sequence
<220> FEATURE:
<223> OTHER INFORMATION: Antimicrobial peptide sequences

<400> SEQUENCE: 164

```
Phe Ala Lys Leu Leu Ala Lys Ala Leu Lys Lys Leu Leu
1               5                   10
```

<210> SEQ ID NO 165
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 165

```
Lys Gly Leu Lys Lys Gly Leu Lys Leu Leu Lys Lys Leu Leu Lys Leu
1               5                   10                  15
```

<210> SEQ ID NO 166
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 166

```
Lys Gly Leu Lys Lys Leu Leu Lys Leu Gly Lys Lys Leu Leu Lys Leu
1               5                   10                  15
```

<210> SEQ ID NO 167
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 167

```
Lys Gly Leu Lys Lys Leu Gly Lys Leu Leu Lys Lys Leu Leu Lys Leu
1               5                   10                  15
```

<210> SEQ ID NO 168
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 168

```
Lys Gly Leu Lys Lys Leu Leu Lys Leu Leu Lys Lys Gly Leu Lys Leu
1               5                   10                  15
```

<210> SEQ ID NO 169
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 169

```
Lys Gly Leu Lys Lys Leu Leu Lys Leu Leu Lys Lys Leu Gly Lys Leu
1               5                   10                  15
```

<210> SEQ ID NO 170
<211> LENGTH: 19
<212> TYPE: PRT
<213> ORGANISM: Artificial Sequence
<220> FEATURE:
<223> OTHER INFORMATION: Antimicrobial peptide sequences

<400> SEQUENCE: 170

```
Phe Ala Leu Ala Leu Lys Ala Leu Lys Lys Leu Lys Lys Ala Leu Lys
```

```
                   1               5                  10                 15

Lys Ala Leu

<210> SEQ ID NO 171
<211> LENGTH: 17
<212> TYPE: PRT
<213> ORGANISM: Artificial Sequence
<220> FEATURE:
<223> OTHER INFORMATION: Antimicrobial peptide sequence

<400> SEQUENCE: 171

Phe Ala Lys Lys Leu Ala Lys Leu Ala Lys Lys Leu Ala Lys Leu Ala
1               5                   10                  15

Leu

<210> SEQ ID NO 172
<211> LENGTH: 13
<212> TYPE: PRT
<213> ORGANISM: Artificial Sequence
<220> FEATURE:
<223> OTHER INFORMATION: Antimicrobial peptide sequences

<400> SEQUENCE: 172

Phe Ala Lys Leu Leu Ala Lys Leu Ala Lys Lys Leu Leu
1               5                   10

<210> SEQ ID NO 173
<211> LENGTH: 15
<212> TYPE: PRT
<213> ORGANISM: Artificial Sequence
<220> FEATURE:
<223> OTHER INFORMATION: Antimicrobial peptide sequences

<400> SEQUENCE: 173

Phe Ala Lys Lys Leu Ala Lys Leu Ala Leu Lys Leu Ala Lys Leu
1               5                   10                  15

<210> SEQ ID NO 174
<211> LENGTH: 10
<212> TYPE: PRT
<213> ORGANISM: Artificial Sequence
<220> FEATURE:
<223> OTHER INFORMATION: Antimicrobial peptide sequences

<400> SEQUENCE: 174

Phe Ala Lys Lys Leu Ala Lys Lys Leu Leu
1               5                   10

<210> SEQ ID NO 175
<211> LENGTH: 13
<212> TYPE: PRT
<213> ORGANISM: Artificial Sequence
<220> FEATURE:
<223> OTHER INFORMATION: Antimicrobial peptide sequence

<400> SEQUENCE: 175

Phe Ala Lys Leu Leu Ala Lys Leu Ala Lys Lys Val Leu
1               5                   10

<210> SEQ ID NO 176
<211> LENGTH: 13
<212> TYPE: PRT
<213> ORGANISM: Artificial Sequence
<220> FEATURE:
<223> OTHER INFORMATION: Antimicrobial peptide sequences
```

```
<400> SEQUENCE: 176

Lys Tyr Lys Lys Ala Leu Lys Lys Leu Ala Lys Leu Leu
1               5                   10

<210> SEQ ID NO 177
<211> LENGTH: 12
<212> TYPE: PRT
<213> ORGANISM: Artificial Sequence
<220> FEATURE:
<223> OTHER INFORMATION: Antimicrobial peptide sequences

<400> SEQUENCE: 177

Phe Ala Leu Leu Lys Ala Leu Leu Lys Lys Ala Leu
1               5                   10

<210> SEQ ID NO 178
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 178

Lys Arg Leu Phe Lys Lys Leu Lys Phe Ser Leu Arg Lys Tyr
1               5                   10

<210> SEQ ID NO 179
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 179

Lys Arg Leu Phe Lys Lys Leu Leu Phe Ser Leu Arg Lys Tyr
1               5                   10

<210> SEQ ID NO 180
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 180

Leu Leu Leu Phe Leu Leu Lys Lys Arg Lys Lys Arg Lys Tyr
1               5                   10

<210> SEQ ID NO 181
<211> LENGTH: 36
<212> TYPE: PRT
<213> ORGANISM: Hyalophora cecropia

<400> SEQUENCE: 181

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Trp Gly Gln Ala Thr
                20                  25                  30

Gln Ile Ala Lys
        35

<210> SEQ ID NO 182
<211> LENGTH: 23
<212> TYPE: PRT
<213> ORGANISM: Xenopus sp.
```

```
<400> SEQUENCE: 182

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 183
<211> LENGTH: 22
<212> TYPE: PRT
<213> ORGANISM: Xenopus sp.

<400> SEQUENCE: 183

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 184
<211> LENGTH: 12
<212> TYPE: PRT
<213> ORGANISM: Bos taurus

<400> SEQUENCE: 184

Arg Leu Cys Arg Ile Val Val Ile Arg Val Cys Arg
1               5                   10

<210> SEQ ID NO 185
<211> LENGTH: 13
<212> TYPE: PRT
<213> ORGANISM: Bos sp.

<400> SEQUENCE: 185

Ile Leu Pro Trp Lys Trp Pro Trp Trp Pro Trp Arg Arg
1               5                   10

<210> SEQ ID NO 186
<211> LENGTH: 24
<212> TYPE: PRT
<213> ORGANISM: Homo sapiens

<400> SEQUENCE: 186

Asp Ser His Ala Lys Arg His His Gly Tyr Lys Arg Lys Phe His Glu
1               5                   10                  15

Lys His His Ser His Arg Gly Tyr
            20

<210> SEQ ID NO 187
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 187

Met Pro Pro Pro Leu Met Gln
1               5

<210> SEQ ID NO 188
<211> LENGTH: 7
<212> TYPE: PRT
<213> ORGANISM: Artificial Sequence
<220> FEATURE:
<223> OTHER INFORMATION: Pigment binding peptide sequences
```

```
<400> SEQUENCE: 188

Phe His Glu Asn Trp Pro Ser
1               5

<210> SEQ ID NO 189
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 189

Arg Thr Ala Pro Thr Thr Pro Leu Leu Leu Ser Leu
1               5                   10

<210> SEQ ID NO 190
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 190

Trp His Leu Ser Trp Ser Pro Val Pro Leu Pro Thr
1               5                   10

<210> SEQ ID NO 191
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 191

Pro His Ala Arg Leu Val Gly
1               5

<210> SEQ ID NO 192
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 192

Asn Ile Pro Tyr His His Pro
1               5

<210> SEQ ID NO 193
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 193

Thr Thr Met Pro Ala Ile Pro
1               5

<210> SEQ ID NO 194
<211> LENGTH: 7
<212> TYPE: PRT
<213> ORGANISM: Artificial Sequence
<220> FEATURE:
<223> OTHER INFORMATION: Pigment binding peptide sequence
```

```
<400> SEQUENCE: 194

His Asn Leu Pro Pro Arg Ser
1               5

<210> SEQ ID NO 195
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 195

Ala His Lys Thr Gln Met Gly Val Arg Gln Pro Ala
1               5                   10

<210> SEQ ID NO 196
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 196

Ala Asp Asn Val Gln Met Gly Val Ser His Thr Pro
1               5                   10

<210> SEQ ID NO 197
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 197

Ala His Asn Ala Gln Met Gly Val Ser His Pro Pro
1               5                   10

<210> SEQ ID NO 198
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 198

Ala Asp Tyr Val Gly Met Gly Val Ser His Arg Pro
1               5                   10

<210> SEQ ID NO 199
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 199

Ser Val Ser Val Gly Met Lys Pro Ser Pro Arg Pro
1               5                   10

<210> SEQ ID NO 200
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 200
```

```
Tyr Pro Asn Thr Ala Leu Val
1               5

<210> SEQ ID NO 201
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 201

Val Ala Thr Arg Ile Val Ser
1               5

<210> SEQ ID NO 202
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 202

His Ser Leu Lys Asn Ser Met Leu Thr Val Met Ala
1               5                   10

<210> SEQ ID NO 203
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 203

Asn Tyr Pro Thr Gln Ala Pro
1               5

<210> SEQ ID NO 204
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 204

Lys Cys Cys Tyr Ser Val Gly
1               5

<210> SEQ ID NO 205
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 205

Arg His Asp Leu Asn Thr Trp Leu Pro Pro Val Lys
1               5                   10

<210> SEQ ID NO 206
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 206
```

```
Glu Ile Ser Leu Pro Ala Lys Leu Pro Ser Ala Ser
1               5                   10
```

<210> SEQ ID NO 207
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 207

```
Ser Asp Tyr Val Gly Met Arg Pro Ser Pro Arg His
1               5                   10
```

<210> SEQ ID NO 208
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 208

```
Ser Asp Tyr Val Gly Met Arg Leu Ser Pro Ser Gln
1               5                   10
```

<210> SEQ ID NO 209
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 209

```
Ser Val Ser Val Gly Ile Gln Pro Ser Pro Arg Pro
1               5                   10
```

<210> SEQ ID NO 210
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 210

```
Tyr Val Ser Val Gly Ile Lys Pro Ser Pro Arg Pro
1               5                   10
```

<210> SEQ ID NO 211
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 211

```
Tyr Val Cys Glu Gly Ile His Pro Cys Pro Arg Pro
1               5                   10
```

<210> SEQ ID NO 212
<211> LENGTH: 7
<212> TYPE: PRT
<213> ORGANISM: Artificial Sequence
<220> FEATURE:
<223> OTHER INFORMATION: Cellulose Binding Peptide

<400> SEQUENCE: 212

```
Val Pro Arg Val Thr Ser Ile
```

-continued

```
1               5

<210> SEQ ID NO 213
<211> LENGTH: 7
<212> TYPE: PRT
<213> ORGANISM: Artificial Sequence
<220> FEATURE:
<223> OTHER INFORMATION: Cellulose-Binding Peptide

<400> SEQUENCE: 213

Met Ala Asn His Asn Leu Ser
1               5

<210> SEQ ID NO 214
<211> LENGTH: 7
<212> TYPE: PRT
<213> ORGANISM: Artificial Sequence
<220> FEATURE:
<223> OTHER INFORMATION: Cellulose-Binding Peptide

<400> SEQUENCE: 214

Phe His Glu Asn Trp Pro Ser
1               5

<210> SEQ ID NO 215
<211> LENGTH: 12
<212> TYPE: PRT
<213> ORGANISM: Artificial sequence
<220> FEATURE:
<223> OTHER INFORMATION: Cellulose-Binding Peptide

<400> SEQUENCE: 215

Thr His Lys Thr Ser Thr Gln Arg Leu Leu Ala Ala
1               5                   10

<210> SEQ ID NO 216
<211> LENGTH: 12
<212> TYPE: PRT
<213> ORGANISM: Artificial sequence
<220> FEATURE:
<223> OTHER INFORMATION: Cellulose-Binding Peptide

<400> SEQUENCE: 216

Lys Cys Cys Tyr Val Asn Val Gly Ser Val Phe Ser
1               5                   10

<210> SEQ ID NO 217
<211> LENGTH: 12
<212> TYPE: PRT
<213> ORGANISM: Artificial sequence
<220> FEATURE:
<223> OTHER INFORMATION: Cellulose-Binding Peptide

<400> SEQUENCE: 217

Ala His Met Gln Phe Arg Thr Ser Leu Thr Pro His
1               5                   10

<210> SEQ ID NO 218
<211> LENGTH: 12
<212> TYPE: PRT
<213> ORGANISM: Artificial sequence
<220> FEATURE:
<223> OTHER INFORMATION: Poly(ethylene terephthalate)-Binding Peptide

<400> SEQUENCE: 218

Gly Thr Ser Asp His Met Ile Met Pro Phe Phe Asn
1               5                   10
```

<210> SEQ ID NO 219
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 219

Thr Ala Val Met Asn Val Val Asn Asn Gln Leu Ser
1               5                   10

<210> SEQ ID NO 220
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 220

Val Pro Trp Trp Ala Pro Ser Lys Leu Ser Met Gln
1               5                   10

<210> SEQ ID NO 221
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 221

Met Val Met Ala Pro His Thr Pro Arg Ala Arg Ser
1               5                   10

<210> SEQ ID NO 222
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 222

Thr Tyr Pro Asn Trp Ala His Leu Leu Ser His Tyr
1               5                   10

<210> SEQ ID NO 223
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 223

Thr Pro Trp Trp Arg Ile Thr
1               5

<210> SEQ ID NO 224
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 224

Asp Leu Thr Leu Pro Phe His
1               5

```
<210> SEQ ID NO 225
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 225

Gly Thr Ser Ile Pro Ala Met
1               5

<210> SEQ ID NO 226
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 226

His His Lys His Val Val Ala
1               5

<210> SEQ ID NO 227
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 227

His His His Lys His Phe Met
1               5

<210> SEQ ID NO 228
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 228

His His His Arg His Gln Gly
1               5

<210> SEQ ID NO 229
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 229

His His Trp His Ala Pro Arg
1               5

<210> SEQ ID NO 230
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 230

Lys Thr Pro Pro Thr Arg Pro
1               5
```

<210> SEQ ID NO 231
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 231

Val Ile Asn Pro Asn Leu Asp
1               5

<210> SEQ ID NO 232
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 232

Lys Val Trp Ile Val Ser Thr
1               5

<210> SEQ ID NO 233
<211> LENGTH: 7
<212> TYPE: PRT
<213> ORGANISM: Artificial Sequence
<220> FEATURE:
<223> OTHER INFORMATION: Nylon-Binding  Peptide

<400> SEQUENCE: 233

Ala Glu Pro Val Ala Met Leu
1               5

<210> SEQ ID NO 234
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 234

Ala Glu Leu Val Ala Met Leu
1               5

<210> SEQ ID NO 235
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 235

His Ser Leu Arg Leu Asp Trp
1               5

<210> SEQ ID NO 236
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 236

Glu Ser Ser Tyr Ser Trp Ser Pro Ala Arg Leu Ser
1               5                   10

<210> SEQ ID NO 237

```
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 237

Gly Pro Leu Lys Leu Leu His Ala Trp Trp Gln Pro
1               5                   10

<210> SEQ ID NO 238
<211> LENGTH: 7
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 238

Asn Ala Leu Thr Arg Pro Val
1               5

<210> SEQ ID NO 239
<211> LENGTH: 7
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 239

Ser Ala Pro Ser Ser Lys Asn
1               5

<210> SEQ ID NO 240
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 240

Ser Val Ser Val Gly Met Lys Pro Ser Pro Arg Pro
1               5                   10

<210> SEQ ID NO 241
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 241

Ser Tyr Tyr Ser Leu Pro Pro Ile Phe His Ile Pro
1               5                   10

<210> SEQ ID NO 242
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 242

Thr Phe Thr Pro Tyr Ser Ile Thr His Ala Leu Leu
1               5                   10

<210> SEQ ID NO 243
<211> LENGTH: 12
```

```
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 243

Thr Met Gly Phe Thr Ala Pro Arg Phe Pro His Tyr
1               5                   10

<210> SEQ ID NO 244
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 244

Thr Asn Pro Phe Pro Pro Pro Ser Ser Pro Ala
1               5                   10

<210> SEQ ID NO 245
<211> LENGTH: 27
<212> TYPE: PRT
<213> ORGANISM: artificial sequence
<220> FEATURE:
<223> OTHER INFORMATION: Clay-binding peptide

<400> SEQUENCE: 245

Gly His Gly Ser Pro Ser Asn Ser His His Gly Ser Lys Lys Cys Asp
1               5                   10                  15

Met Gly Asn Ser Arg Ala Lys Cys Lys Arg Leu
            20                  25

<210> SEQ ID NO 246
<211> LENGTH: 27
<212> TYPE: PRT
<213> ORGANISM: artificial sequence
<220> FEATURE:
<223> OTHER INFORMATION: Clay-binding peptide

<400> SEQUENCE: 246

Ser Asp Arg His Asn Leu Arg Asn Ser Trp Ser Ile Ser Arg His Cys
1               5                   10                  15

Arg Arg Lys Gln Gly Arg Cys Leu Pro Ala His
            20                  25

<210> SEQ ID NO 247
<211> LENGTH: 27
<212> TYPE: PRT
<213> ORGANISM: artificial sequence
<220> FEATURE:
<223> OTHER INFORMATION: Clay-binding peptide

<400> SEQUENCE: 247

Lys Lys Ser Asn Lys Gly His His Pro Ser Ser Lys Gly Lys Gly Pro
1               5                   10                  15

Pro Trp Ser Glu Trp Asp Lys Lys Asn Gly Pro
            20                  25

<210> SEQ ID NO 248
<211> LENGTH: 27
<212> TYPE: PRT
<213> ORGANISM: artificial sequence
<220> FEATURE:
<223> OTHER INFORMATION: Clay-binding peptide
```

<400> SEQUENCE: 248

Lys Lys Ser Asn Lys Gly Pro His Pro Ser Lys Gly Lys Gly Pro
1               5                   10                  15

Pro Trp Ser Glu Trp Asp Lys Lys Asn Gly Pro
            20                  25

<210> SEQ ID NO 249
<211> LENGTH: 22
<212> TYPE: PRT
<213> ORGANISM: artificial sequence
<220> FEATURE:
<223> OTHER INFORMATION: Clay-binding peptide

<400> SEQUENCE: 249

Val Gly Arg His His Ser Lys Ala Lys Gln Lys Arg Pro His Gly Gly
1               5                   10                  15

Lys Gly Gln Asn Lys Asn
            20

<210> SEQ ID NO 250
<211> LENGTH: 22
<212> TYPE: PRT
<213> ORGANISM: artificial sequence
<220> FEATURE:
<223> OTHER INFORMATION: Clay-binding peptide

<400> SEQUENCE: 250

Val Gly Arg His His Pro Lys Ala Lys Gln Lys Arg Pro His Gly Gly
1               5                   10                  15

Lys Gly Gln Asn Lys Asn
            20

<210> SEQ ID NO 251
<211> LENGTH: 17
<212> TYPE: PRT
<213> ORGANISM: artificial sequence
<220> FEATURE:
<223> OTHER INFORMATION: Clay-binding peptide

<400> SEQUENCE: 251

Gly Arg Arg Pro Arg Ala Arg Gly Arg Ser Arg Arg Gly Ser Thr Lys
1               5                   10                  15

Thr

<210> SEQ ID NO 252
<211> LENGTH: 19
<212> TYPE: PRT
<213> ORGANISM: artificial sequence
<220> FEATURE:
<223> OTHER INFORMATION: Clay-binding peptide

<400> SEQUENCE: 252

Leu Gly Val Ile Arg Asn His Val Val Arg Gly Arg Arg His His Gln
1               5                   10                  15

His Val Arg

<210> SEQ ID NO 253
<211> LENGTH: 27
<212> TYPE: PRT
<213> ORGANISM: artificial sequence
<220> FEATURE:
<223> OTHER INFORMATION: Clay-binding peptide

<400> SEQUENCE: 253

-continued

Gln Pro Gly Arg Pro Thr Glu Val His Pro Glu Leu Val Arg Lys Ser
1               5                   10                  15

Ala Tyr Leu Val Asn Pro Ser Glu Asp Ile Arg
            20                  25

<210> SEQ ID NO 254
<211> LENGTH: 27
<212> TYPE: PRT
<213> ORGANISM: artificial sequence
<220> FEATURE:
<223> OTHER INFORMATION: Clay-binding peptide

<400> SEQUENCE: 254

His Arg Ser Glu Lys Pro Lys Asn Val Lys Tyr Lys Arg Gly Tyr Trp
1               5                   10                  15

Glu Arg Gly Asn Gln Lys Lys His Gly Pro Gly
            20                  25

<210> SEQ ID NO 255
<211> LENGTH: 27
<212> TYPE: PRT
<213> ORGANISM: artificial sequence
<220> FEATURE:
<223> OTHER INFORMATION: Clay-binding peptide

<400> SEQUENCE: 255

Gly Ser His Lys Arg Arg Gly Ser Tyr Ala Leu Leu Arg Thr Arg Gly
1               5                   10                  15

Val Gly Arg Gln Ala Glu Leu Glu His Leu Leu
            20                  25

<210> SEQ ID NO 256
<211> LENGTH: 27
<212> TYPE: PRT
<213> ORGANISM: artificial sequence
<220> FEATURE:
<223> OTHER INFORMATION: Clay-binding peptide

<400> SEQUENCE: 256

Val Gly Glu Lys Pro Arg Arg Lys Ser Lys Gly Ala Lys Ala Lys Lys
1               5                   10                  15

Ala Arg Thr Lys Glu Gln Lys Leu Pro Lys Asn
            20                  25

<210> SEQ ID NO 257
<211> LENGTH: 27
<212> TYPE: PRT
<213> ORGANISM: artificial sequence
<220> FEATURE:
<223> OTHER INFORMATION: Clay-binding peptide

<400> SEQUENCE: 257

Asn Lys Gly His Lys Gln Ser Gly Ser Pro Arg His Ser Asn Lys Lys
1               5                   10                  15

Glu Lys Lys Thr Gln Gln Lys Arg Gly Gln Pro
            20                  25

<210> SEQ ID NO 258
<211> LENGTH: 27
<212> TYPE: PRT
<213> ORGANISM: artificial sequence
<220> FEATURE:
<223> OTHER INFORMATION: Clay-binding peptide

```
<400> SEQUENCE: 258

His Trp Gly Ser Gln His Lys Thr Gly Leu Arg Asn His Lys Arg Ser
1               5                   10                  15

Arg Arg Asp Ser Leu Gly Lys Arg Gly Thr Asp
            20                  25

<210> SEQ ID NO 259
<211> LENGTH: 27
<212> TYPE: PRT
<213> ORGANISM: artificial sequence
<220> FEATURE:
<223> OTHER INFORMATION: Clay-binding peptide

<400> SEQUENCE: 259

Lys Gly Trp Gly Ser Ser Ser Gly Pro Pro Gly Leu Thr Gly Lys Ala
1               5                   10                  15

Leu Gly Lys Gly Arg Leu Lys Pro Lys Lys Lys
            20                  25

<210> SEQ ID NO 260
<211> LENGTH: 24
<212> TYPE: PRT
<213> ORGANISM: artificial sequence
<220> FEATURE:
<223> OTHER INFORMATION: Clay-binding peptide

<400> SEQUENCE: 260

Ser Ser Lys Ser Gly Ala Pro Phe Arg Val Pro Ile Cys Phe Thr Ala
1               5                   10                  15

Pro Arg Pro Gln Lys Thr Leu Gly
            20

<210> SEQ ID NO 261
<211> LENGTH: 5
<212> TYPE: PRT
<213> ORGANISM: artificial sequence
<220> FEATURE:
<223> OTHER INFORMATION: Caspase-3 cleavage sequence
<220> FEATURE:
<221> NAME/KEY: MISC_FEATURE
<222> LOCATION: (5)..(5)
<223> OTHER INFORMATION: Xaa = any naturally occurring amino acid except
      Pro, Glu, Asp, Gln, Lys, and Arg.

<400> SEQUENCE: 261

Asp Met Gln Asp Xaa
1               5

<210> SEQ ID NO 262
<211> LENGTH: 22
<212> TYPE: PRT
<213> ORGANISM: artificial sequence
<220> FEATURE:
<223> OTHER INFORMATION: Synthetic construct. Inclusion body tag
<220> FEATURE:
<221> NAME/KEY: MISC_FEATURE
<222> LOCATION: (3)..(3)
<223> OTHER INFORMATION: Xaa = Arg, His, or Lys
<220> FEATURE:
<221> NAME/KEY: MISC_FEATURE
<222> LOCATION: (5)..(5)
<223> OTHER INFORMATION: Xaa = Gln, His, or Lys
<220> FEATURE:
<221> NAME/KEY: MISC_FEATURE
<222> LOCATION: (7)..(7)
<223> OTHER INFORMATION: Xaa = Gln, His, or Lys
<220> FEATURE:
<221> NAME/KEY: MISC_FEATURE
```

```
<222> LOCATION: (9)..(9)
<223> OTHER INFORMATION: Xaa = Glu or Gln
<220> FEATURE:
<221> NAME/KEY: MISC_FEATURE
<222> LOCATION: (10)..(10)
<223> OTHER INFORMATION: Xaa = Gln or Lys
<220> FEATURE:
<221> NAME/KEY: MISC_FEATURE
<222> LOCATION: (11)..(11)
<223> OTHER INFORMATION: Location of peptide spacer connecting glutamine
      at residue position 11 with the glutamine at residue position 12.
<220> FEATURE:
<221> NAME/KEY: MISC_FEATURE
<222> LOCATION: (14)..(14)
<223> OTHER INFORMATION: Xaa = Arg, His, or Lys
<220> FEATURE:
<221> NAME/KEY: MISC_FEATURE
<222> LOCATION: (16)..(16)
<223> OTHER INFORMATION: Xaa = Gln, His, or Lys
<220> FEATURE:
<221> NAME/KEY: MISC_FEATURE
<222> LOCATION: (18)..(18)
<223> OTHER INFORMATION: Xaa = Gln, His, or Lys
<220> FEATURE:
<221> NAME/KEY: MISC_FEATURE
<222> LOCATION: (20)..(20)
<223> OTHER INFORMATION: Xaa = Glu or Gln
<220> FEATURE:
<221> NAME/KEY: MISC_FEATURE
<222> LOCATION: (21)..(21)
<223> OTHER INFORMATION: Xaa = Gln or Lys
<220> FEATURE:
<221> NAME/KEY: MISC_FEATURE
<222> LOCATION: (22)..(22)
<223> OTHER INFORMATION: Location of additional peptide spacers
      separating additional core sequences

<400> SEQUENCE: 262

Gln Gln Xaa Phe Xaa Trp Xaa Phe Xaa Xaa Gln Gln Gln Xaa Phe Xaa
1               5                   10                  15

Trp Xaa Phe Xaa Xaa Gln
            20
```

SOLUBILITY TAGS FOR THE EXPRESSION AND PURIFICATION OF BIOACTIVE PEPTIDES

FIELD OF THE INVENTION

The invention relates to the field of protein expression and purification from microbial cells. More specifically, a family of small peptide tags is provided useful in the generation of insoluble fusion proteins.

BACKGROUND OF THE INVENTION

The efficient production of bioactive proteins and peptides has become a hallmark of the biomedical and industrial biochemical industry. Bioactive peptides and proteins are used as curative agents in a variety of diseases such as diabetes (insulin), viral infections and leukemia (interferon), diseases of the immune system (interleukins), and red blood cell deficiencies (erythropoietin) to name a few. Additionally, large quantities of proteins and peptides are needed for various industrial applications including, for example, the pulp and paper and pulp industries, textiles, food industries, personal care and cosmetics industries, sugar refining, wastewater treatment, production of alcoholic beverages and as catalysts for the generation of new pharmaceuticals.

With the advent of the discovery and implementation of combinatorial peptide screening technologies such as bacterial display (Kemp, D. J.; *Proc. Natl. Acad. Sci. USA* 78(7): 4520-4524 (1981); yeast display (Chien et al., *Proc Natl Acad Sci USA* 88(21): 9578-82 (1991)), combinatorial solid phase peptide synthesis (U.S. Pat. No. 5,449,754; U.S. Pat. No. 5,480,971; U.S. Pat. No. 5,585,275 and U.S. Pat. No. 5,639,603), phage display technology (U.S. Pat. No. 5,223,409; U.S. Pat. No. 5,403,484; U.S. Pat. No. 5,571,698; and U.S. Pat. No. 5,837,500), ribosome display (U.S. Pat. No. 5,643,768; U.S. Pat. No. 5,658,754; and U.S. Pat. No. 7,074,557), and mRNA display technology (PROFUSION™; U.S. Pat. No. 6,258,558; U.S. Pat. No. 6,518,018; U.S. Pat. No. 6,281,344; U.S. Pat. No. 6,214,553; U.S. Pat. No. 6,261,804; U.S. Pat. No. 6,207,446; U.S. Pat. No. 6,846,655; U.S. Pat. No. 6,312,927; U.S. Pat. No. 6,602,685; U.S. Pat. No. 6,416,950; U.S. Pat. No. 6,429,300; U.S. Pat. No. 7,078,197; and U.S. Pat. No. 6,436,665) new applications for peptides having specific binding affinities have been developed. In particular, peptides are being looked to as linkers in biomedical fields for the attachment of diagnostic and pharmaceutical agents to surfaces (see Grinstaff et al, U.S. Patent Application Publication No. 2003/0185870 and Linter in U.S. Pat. No. 6,620,419), as well as in the personal care industry for the attachment of benefit agents to body surfaces such as hair and skin (see commonly owned U.S. patent application Ser. No. 10/935,642, and Janssen et al. U.S. Patent Application Publication No. 2003/0152976), and in the printing industry for the attachment of pigments to print media (see commonly owned U.S. patent application Ser. No. 10/935,254).

In some cases commercially useful proteins and peptides may be synthetically generated or isolated from natural sources. However, these methods are often expensive, time consuming and characterized by limited production capacity. The preferred method of protein and peptide production is through the fermentation of recombinantly constructed organisms, engineered to over-express the protein or peptide of interest. Although preferable to synthesis or isolation, recombinant expression of peptides has a number of obstacles to be overcome in order to be a cost-effective means of production. For example, peptides (and in particular short peptides) produced in a cellular environment are susceptible to degradation from the action of native cellular proteases. Additionally, purification can be difficult, resulting in poor yields depending on the nature of the protein or peptide of interest.

One means to mitigate the above difficulties is the use the genetic chimera for protein and peptide expression. A chimeric protein or "fusion protein" is a polypeptide comprising at least one portion of the desired protein product fused to at least one portion comprising a peptide tag. The peptide tag may be used to assist protein folding, assist post expression purification, protect the protein from the action of degradative enzymes, and/or assist the protein in passing through the cell membrane.

In many cases it is useful to express a protein or peptide in insoluble form, particularly when the peptide of interest is rather short, normally soluble, and/or subject to proteolytic degradation within the host cell. Production of the peptide in insoluble form both facilitates simple recovery and protects the peptide from the undesirable proteolytic degradation. One means to produce the peptide in insoluble form is to recombinantly produce the peptide as part of an insoluble fusion protein by including in the fusion construct at least one peptide tag (i.e., an inclusion body tag) that induces inclusion body formation. Typically, the fusion protein is designed to include at least one cleavable peptide linker so that the peptide of interest can be subsequently recovered from the fusion protein. The fusion protein may be designed to include a plurality of inclusion body tags, cleavable peptide linkers, and regions encoding the peptide of interest.

Fusion proteins comprising a peptide tag that facilitate the expression of insoluble proteins are well known in the art. Typically, the tag portion of the chimeric or fusion protein is large, increasing the likelihood that the fusion protein will be insoluble. Example of large peptide tides typically used include, but are not limited to chloramphenicol acetyltransferase (Dykes et al., *Eur. J. Biochem.*, 174:411 (1988), β-galactosidase (Schellenberger et al., *Int. J. Peptide Protein Res.*, 41:326 (1993); Shen et al., *Proc. Nat. Acad. Sci. USA* 281: 4627 (1984); and Kempe et al., *Gene*, 39:239 (1985)), glutathione-S-transferase (Ray et al., *Bio/Technology*, 11:64 (1993) and Hancock et al. (WO94/04688)), the N-terminus of L-ribulokinase (U.S. Pat. No. 5,206,154 and Lai et al., *Antimicrob. Agents & Chemo.*, 37:1614 (1993), bacteriophage T4 gp55 protein (Gramm et al., *Bio/Technology*, 12:1017 (1994), bacterial ketosteroid isomerase protein (Kuliopulos et al., *J. Am. Chem. Soc.* 116:4599 (1994), ubiquitin (Pilon et al., *Biotechnol. Prog.*, 13:374-79 (1997), bovine prochymosin (Naught et al., *Biotechnol. Bioengineer.* 57:55-61 (1998), and bactericidal/permeability-increasing protein ("BPI"; Better, M. D. and Gavit, P D., U.S. Pat. No. 6,242,219). The art is replete with specific examples of this technology, see for example U.S. Pat. No. 6,613,548, describing fusion protein of proteinaceous tag and a soluble protein and subsequent purification from cell lysate; U.S. Pat. No. 6,037,145, teaching a tag that protects the expressed chimeric protein from a specific protease; U.S. Pat. No. 5,648,244, teaching the synthesis of a fusion protein having a tag and a cleavable linker for facile purification of the desired protein; and U.S. Pat. No. 5,215,896; U.S. Pat. No. 5,302,526; U.S. Pat. No. 5,330,902; and US 2005221444, describing fusion tags containing amino acid compositions specifically designed to increase insolubility of the chimeric protein or peptide.

Shorter inclusion body tags have recently been developed from the *Zea mays* zein protein (co-owned U.S. patent application Ser. No. 11/641,936), the *Daucus carota* cystatin (co-owned U.S. patent application Ser. No. 11/641,273), and an amyloid-like hypothetical protein from *Caenorhabditis* elegans (co-owned U.S. patent application Ser. No. 11/516, 362; each hereby incorporated by reference in their entirety.) The use of short inclusion body tags increases the yield of the target peptide produced within the recombinant host cell.

The problem to be solved is to provide solubility tags that are effective in preparing fusion proteins comprising a peptide of interest.

SUMMARY OF THE INVENTION

The stated problem has been solved though the discovery of a set of structurally similar short inclusion body tags (IBTs) useful for synthesizing fusion proteins for increased expression and simple purification of short peptides ("peptides of interest").

The invention relates to a set of peptide inclusion body tags that may be linked to a peptide of interest to be expressed to facilitate insolubility and subsequent recovery of the expressed peptide.

Accordingly, the invention provides an inclusion body tag comprising the structure:

Gln-Gln-Xaa1-Phe-Xaa2-Trp-Xaa3-Phe-Xaa4-Xaa5-Gln-Spacer-[[Gln-Gln-Xaa1-Phe-Xaa2-Trp-Xaa3-Phe-Xaa4-Xaa5-Gln]-[Spacer]$_m$]$_n$ wherein
Xaa1=Arg, His, or Lys;
Xaa2=Gln, His, or Lys;
Xaa3=Gln, His, or Lys;
Xaa4=Glu or Gln;
Xaa5=Gln or Lys;
n=1 to 10;
m=n−1; and
wherein the Spacer=is a peptide comprising amino acids selected from the group consisting of proline, arginine, glycine, glutamic acid, and cysteine.

In a further embodiment, the present inclusion body tags comprise at least two copies of the core sequence (Gln-Gln-Xaa1-Phe-Xaa2-Trp-Xaa3-Phe-Xaa4-Xaa5-Gln; SEQ ID NO: 58) wherein Xaa1=Arg, His, or Lys; Xaa2=Gln, His, or Lys; Xaa3=Gln, His, or Lys; Xaa4=Glu or Gln; and Xaa5=Gln or Lys; wherein the core sequence is separated by at least one spacer as defined above.

In another embodiment, the inclusion body tag further comprises at least one cross-linkable tetracysteine moiety (CCPGCC; SEQ ID NO: 33). In a further embodiment, the cross-linkable cysteine moiety is located on the amino and/or carboxy terminus of the inclusion body tag defined above.

In another embodiment, the inclusion body tag is selected from the group consisting of IBT103 (SEQ ID NO: 15), IBT138 (SEQ ID NO: 19), IBT 139 (SEQ ID NO: 21), IBT139.CCPGCC (SEQ ID NO: 31); IBT 182 (SEQ ID NO: 39), IBT 183 (SEQ ID NO: 41), IBT184 (SEQ ID NO: 43), IBT185 (SEQ ID NO: 45), IBT 186 (SEQ ID NO: 27), IBT 187a (SEQ ID NO: 47), and IBT187b (SEQ ID NO: 49).

In another embodiment, an insoluble fusion peptide is provided comprising the present inclusion body tag (IBT) operably linked to a peptide of interest (POI) and separated by at least once cleavable peptide linker sequence (CS).

In another embodiment, the peptide of interest is selected from the group consisting of hair-binding peptides, nail-binding peptides, skin-binding peptides, polymer-binding peptides, clay-binding peptides, antimicrobial peptides, pigment-binding peptides, and cellulose-binding peptides.

In yet another embodiment, the peptide of interest is a multi-block peptide.

In a further embodiment, the invention provides a method for expressing a peptide of interest in insoluble form comprising:
a) synthesizing a genetic construct encoding a fusion peptide comprising a first portion encoding the inclusion body tag of the invention operably linked to a second portion encoding a peptide of interest;
b) transforming an expression host cell with the genetic construct of (a);
c) growing the transformed host cell of (b) under conditions wherein the genetic construct is expressed and the encoded fusion peptide is produced in an insoluble form; and
d) recovering said fusion peptide in said insoluble form.

In another embodiment, a method for the production of a peptide of interest is provided comprising:
a) synthesizing a genetic construct encoding a fusion peptide comprising a first portion comprising present inclusion body tag operably linked to a second portion comprising a peptide of interest; wherein said first portion and said second portion are separated by at least one cleavable peptide linker;
b) transforming an expression host cell with the genetic construct of (a);
c) growing the transformed host cell of (b) under conditions wherein the genetic construct is expressed and the encoded fusion peptide is produced in an insoluble form;
d) recovering the fusion peptide in said insoluble form;
e) cleaving said at least one cleavable peptide linker whereby said first portion of the fusion peptide is no longer fused to said second portion; and
f) recovering said peptide of interest.

In another embodiment, the invention provides a chimeric genetic construct encoding a fusion protein comprising at least one of the present inclusion body tags and at least one peptide of interest.

In yet another embodiment, the invention provides expression vectors and microbial host cells comprising the present chimeric genetic constructs.

BRIEF DESCRIPTION OF THE FIGURES

FIG. 1 is a CLUSTALW alignment of the present inclusion body tags. The regions representing the core sequence are underlined.

BRIEF DESCRIPTION OF THE BIOLOGICAL SEQUENCES

Figure 2:
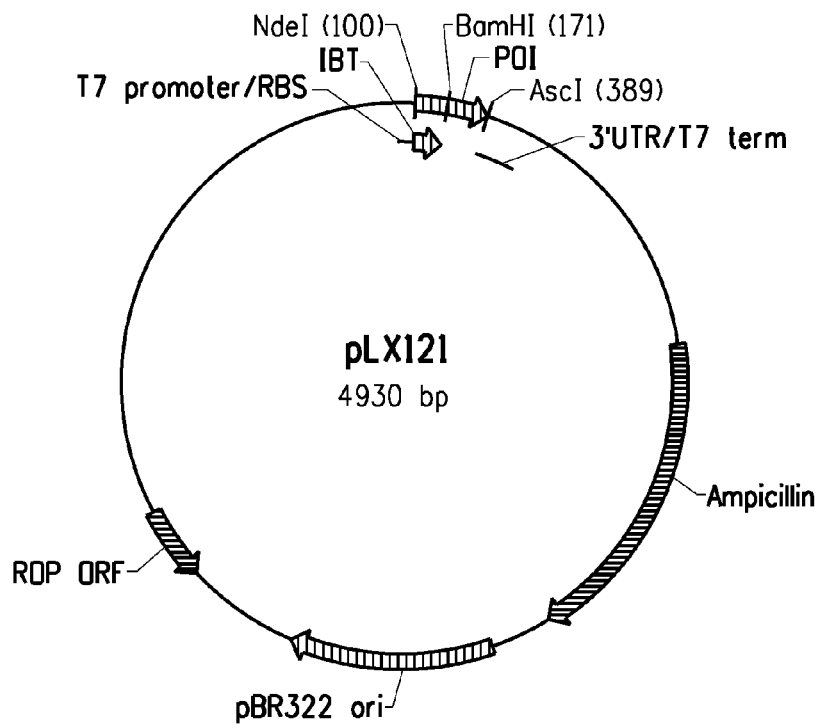
FIG. 2 is a diagram of expression plasmid pLX121. Construction of pLX121 is described U.S. patent application Ser. No. 11/516,362; herein incorporated by reference.

The following sequences comply with 37 C.F.R. 1.821-1.825 ("Requirements for patent applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPC and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

SEQ ID NO: 1 is the nucleotide sequence of plasmid pLX121.

SEQ ID NO: 2 is the nucleotide sequence of plasmid pSF032.

SEQ ID NO: 3 is the amino acid sequence of hair-binding peptide A09.

SEQ ID NO: 4 is the amino acid sequence of hair-binding peptide KF11.

SEQ ID NO: 5 is the amino acid sequence of hair-binding peptide D21'.

SEQ ID NO: 6 is the nucleic acid sequence encoding HC77607.

SEQ ID NO: 7 is the amino acid sequence of HC77607.

SEQ ID NO: 8 is the nucleic acid sequence encoding HC77638.

SEQ ID NO: 9 is the amino acid sequence of HC77638.

SEQ ID NO: 10 is the nucleic acid sequence encoding HC77643.

SEQ ID NO: 11 is the amino acid sequence of HC77643.

SEQ ID NO: 12 is the nucleic acid sequence encoding HC77681.

SEQ ID NO: 13 is the amino acid sequence of HC77681.

SEQ ID NO: 14 is the nucleic acid sequence encoding IBT103.

SEQ ID NO: 15 is the amino acid sequence of IBT103.

SEQ ID NO: 16 is the nucleic acid sequence encoding IBT136.

SEQ ID NO: 17 is the amino acid sequence of IBT136 and the $P_{11}$-II peptide described in Aggeli et al. (*PNAS* 98(21): 11857-11862 (2001).

SEQ ID NO: 18 is the nucleic acid sequence encoding IBT138.

SEQ ID NO: 19 is the amino acid sequence of IBT138.

SEQ ID NO: 20 is the nucleic acid sequence encoding IBT139.

SEQ ID NO: 21 is the amino acid sequence of IBT139.

SEQ ID NO: 22 is the nucleic acid sequence encoding HC776124.

SEQ ID NO: 23 is the amino acid sequence of HC776124.

SEQ ID NO: 24 is the nucleic acid sequence encoding fusion peptide IBT139.HC776124.

SEQ ID NO: 25 is the amino acid sequence of IBT139.HC776124.

SEQ ID NO: 26 is the nucleic acid sequence encoding IBT186.

SEQ ID NO: 27 is the amino acid sequence of IBT186.

SEQ ID NO: 28 is the nucleic acid sequence encoding fusion peptide IBT186.HC776124.

SEQ ID NO: 29 is the amino acid sequence of IBT186.HC776124.

SEQ ID NO: 30 is the nucleic acid sequence encoding IBT139.CCPGCC.

SEQ ID NO: 31 is the amino acid sequence of IBT139.CCPGCC.

SEQ ID NO: 32 is the nucleic acid sequence encoding the cross-linkable cysteine moiety CCPGCC.

SEQ ID NO: 33 is the amino acid sequence of the cross-linkable cysteine moiety CCPGCC.

SEQ ID NOs: 34-35 are the nucleic acid sequences of oligonucleotides used to prepare IBT139.CCPGCC.

SEQ ID NO: 36 is the nucleic acid sequence of fusion peptide IBT139.CCPGCC.HC776124.

SEQ ID NO: 37 is the nucleic acid sequence of fusion peptide IBT139.CCPGCC.HC776124.

SEQ ID NO: 38 is the nucleic acid sequence encoding IBT182.

SEQ ID NO: 39 is the amino acid sequence of IBT182.

SEQ ID NO: 40 is the nucleic acid sequence encoding IBT183.

SEQ ID NO: 41 is the amino acid sequence of IBT183.

SEQ ID NO: 42 is the nucleic acid sequence encoding IBT184

SEQ ID NO: 43 is the amino acid sequence of IBT184.

SEQ ID NO: 44 is the nucleic acid sequence encoding IBT185

SEQ ID NO: 45 is the amino acid sequence of IBT185.

SEQ ID NO: 46 is the nucleic acid sequence encoding IBT187a

SEQ ID NO: 47 is the amino acid sequence of IBT187a.

SEQ ID NO: 48 is the nucleic acid sequence encoding IBT187b

SEQ ID NO: 49 is the amino acid sequence of IBT187b.

SEQ ID NO: 50 is the nucleic acid sequence of plasmid pSF043.

SEQ ID NO: 51 is the nucleic acid sequence of plasmid pLR186.

SEQ ID NO: 52 is the nucleic acid sequence of the KSI (C4).

SEQ ID NO: 53 is the amino acid sequence of KSI(C4).

SEQ ID NO: 54 is the nucleic acid sequence encoding the fusion peptide KSI(C4)-HC7643.

SEQ ID NO: 55 is the amino acid sequence of fusion peptide KSI(C4)-HC77643.

SEQ ID NOs: 56-57 are the amino acid sequences of spacers used in the present inclusion body tags.

SEQ ID NO: 58 is the amino acid sequence of the core sequence found in the present inclusion body tags SEQ ID NOs: 59-147 are the amino acid sequences of hair binding peptides.

SEQ ID NOs: 148-155 are the amino acid sequences of skin binding peptides.

SEQ ID NOs: 156-157 are the amino acid sequences of nail-binding peptides.

SEQ ID NOs: 158-186 are the amino acid sequences of antimicrobial peptides.

SEQ ID NOs: 187-211 are the amino acid sequences of pigment binding peptides. Specifically, SEQ ID NOs: 187-190 bind to carbon black, SEQ ID NOs: 191-199 bind to CROMOPHTAL® yellow (Ciba Specialty Chemicals, Basel, Switzerland), SEQ ID NOs: 200-202 bind to SUNFAST® magenta (Sun Chemical Corp., Parsippany, N.J.), and SEQ ID NOs: 203-211 bind to SUNFAST® blue.

SEQ ID NOs: 212-217 are cellulose-binding peptides.

SEQ ID NOs: 218-244 are the amino acid sequences of polymer binding peptides. Specifically, SEQ ID NO: 218 binds to poly(ethylene terephthalate), SEQ ID NOs: 219-229 bind to poly(methyl methacrylate), SEQ ID NOs: 230-235 bind to Nylon, and SEQ ID NOs: 236-244 bind to poly(tetrafluoroethylene).

SEQ ID NOs: 245-260 are the amino acid sequences of clay binding peptides.

SEQ ID NO: 261 is the amino acid sequence of the Caspase-3 cleavage sequence.

SEQ ID NO: 262 is the amino acid sequence of the preferred inclusion body tag of the invention comprising a spacer.

DETAILED DESCRIPTION OF THE INVENTION

The present invention describes a set of peptide tags (inclusion body tags) that may be coupled with a peptide of interest to form a fusion peptide. The fusion peptide, so assembled, is expressed in insoluble form and accumulated in inclusion bodies in the expressing host cell. The inclusion bodies are recovered and subsequently cleaved to separate the peptide of interest from the inclusion body tag. In a preferred embodiment, the fusion protein comprises at least one cleavable peptide linker separating the inclusion body tag from the peptide of interest. In another preferred embodiment, the cleavable peptide linker comprises at least one acid cleavable aspartic acid-proline moiety.

In a further embodiment, the inclusion body tag comprises an effective number of cross-linkable cysteine residues useful during subsequent processing to separate the inclusion body tag from the peptide of interest. In yet a further embodiment, the inclusion body tag comprises at least one cross-linkable cysteine moiety CCPGCC (SEQ ID NO: 33) on the amino and/or carboxy terminus of the IBT.

The invention is useful for the expression and recovery of any bioactive peptides and proteins that are recombinantly expressed. Such proteins typically have high value in any number of applications including, but not limited to medical, biomedical, diagnostic, personal care, and affinity applications where the peptides of interest are used as linkers to various surfaces.

The following definitions are used herein and should be referred to for interpretation of the claims and the specification. Unless otherwise noted, all U.S. patents and U.S. patent applications referenced herein are incorporated by reference in their entirety.

As used herein, the term "comprising" means the presence of the stated features, integers, steps, or components as referred to in the claims, but that it does not preclude the presence or addition of one or more other features, integers, steps, components or groups thereof.

As used herein, the term "about" refers to modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

As used herein, the term "pigment" refers to an insoluble, organic or inorganic colorant.

As used herein, the term "hair" as used herein refers to human hair, eyebrows, and eyelashes.

As used herein, the term "skin" as used herein refers to human skin, or substitutes for human skin, such as pig skin, VITRO-SKIN® and EPIDERM™. Skin, as used herein, will refer to a body surface generally comprising a layer of epithelial cells and may additionally comprise a layer of endothelial cells.

As used herein, the term "nails" as used herein refers to human fingernails and toenails.

As used herein, "PBP" means polymer-binding peptide. As used herein, the term "polymer-binding peptide" refers to peptide sequences that bind with high affinity to a specific polymer (U.S. patent application Ser. No. 11/516,362). Examples include peptides that bind to poly(ethylene terephthalate) (SEQ ID NO: 218), poly(methyl methacrylate) (SEQ ID NOs: 219-229), Nylon (SEQ ID NOs: 230-235), and poly (tetrafluoroethylene) (SEQ ID NOs: 236-244).

As used herein, "HBP" means hair-binding peptide. As used herein, the term "hair-binding peptide" refers to peptide sequences that bind with high affinity to hair. The hair-binding peptide may be comprised of a single hair-binding domain or multiple binding domains wherein at least one of the binding-domains binds to hair (i.e. multi-block peptides). Examples of hair binding peptides have been reported (U.S. patent application Ser. No. 11/074,473 to Huang et al.; WO 0179479; U.S. Patent Application Publication No. 2002/0098524 to Murray et al.; Janssen et al., U.S. Patent Application Publication No. 2003/0152976 to Janssen et al.; WO 2004048399; U.S. application Ser. No. 11/512,910, and U.S. patent application Ser. No. 11/696,380). Examples of hair-binding peptides are provided as SEQ ID NOs: 3-5, 7, 9, 11, 13, 23, and 59-147.

As used herein, "SBP" means skin-binding peptide. As used herein, the term "skin-binding peptide" refers to peptide sequences that bind with high affinity to skin. Examples of skin binding peptides have also been reported (U.S. patent application Ser. No. 11/069,858 to Buseman-Williams; Rothe et. al., WO 2004/000257; and U.S. patent application Ser. No. 11/696,380). Skin as used herein as a body surface will generally comprise a layer of epithelial cells and may additionally comprise a layer of endothelial cells. Examples of skin-binding peptides are provided as SEQ ID NOs: 148-155.

As used herein, "NBP" means nail-binding peptide. As used herein, the term "nail-binding peptide" refers to peptide sequences that bind with high affinity to nail. Examples of nail binding peptides have been reported (U.S. patent application Ser. No. 11/696,380). Examples of nail-binding peptides are provided as SEQ ID NOs: 156-157.

As used herein, an "antimicrobial peptide" is a peptide having the ability to kill microbial cell populations (U.S. patent application Ser. No. 11/516,362). Examples of antimicrobial peptides are provided as SEQ ID NOs: 158-186.

As used herein, "cellulose-binding peptide" refers to a peptide that binds with high affinity to cellulose. Examples of cellulose-binding peptides are provided as SEQ ID NOs: 212 to 217.

As used herein, "clay-binding peptide" refers to a peptide that binds with high affinity to clay (U.S. patent application Ser. No. 11/696,380). Examples of clay-binding peptides are provided as SEQ ID NOs: 245 to 260.

As used herein, "multi-block peptides" refers to a peptide comprising at least two binding moieties. Each binding moiety has an affinity for a target substrate (e.g. hair, skin, a pigment, etc). The binding moieties may have an affinity for the same or different substrates (for example, a hair-binding moiety fused to a pigment binding moiety for targeted delivery of a pigment to hair or a peptide having a plurality of hair-binding moieties).

As used herein, the term "inclusion body tag" will be abbreviated "IBT" and will refer a polypeptide that facilitates formation of inclusion bodies when fused to a peptide of interest. The peptide of interest is typically soluble within the host cell and/or host cell lysate when not fused to an inclusion body tag. Fusion of the peptide of interest to the inclusion body tag produces a fusion protein that agglomerates into intracellular bodies (inclusion bodies) within the host cell.

As used herein, the term "spacer" will refer to a peptide within the present inclusion body tags used to separate the core sequences (SEQ ID NO: 58). In one embodiment, the spacer is 2-10 amino acids in length, preferably 3 to 6 amino acids in length, and most preferably 3 to 4 amino acids in length and is comprised of amino acids selected from the group consisting of proline, glycine, cysteine, arginine, and glutamic acid. In one embodiment, the spacer is selected from the group consisting of Pro-Arg-Gly, Pro-Cys-Gly, Pro-Arg-Cys-Gly (SEQ ID NO: 56), Pro-Glu-Gly, and Pro-Glu-Cys-Gly (SEQ ID NO: 57).

As used herein, "cleavable linker elements", "peptide linkers", "cleavable peptide linkers", and "cleavage site" will be used interchangeably and refer to cleavable peptide segments located between the inclusion body tag and the peptide of interest. After the inclusion bodies are separated and/or partially-purified or purified from the cell lysate, the cleavable linker elements can be cleaved chemically and/or enzymatically to separate the inclusion body tag from the peptide of interest. The fusion peptide may also include a plurality of regions encoding one or more peptides of interest separated by one or more cleavable peptide linkers. The peptide of interest can then be isolated from the inclusion body tag, if necessary. In one embodiment, the inclusion body tag(s) and the peptide of interest exhibit different solubilities in a defined medium (typically an aqueous medium), facilitating separation of the inclusion body tag from the polypeptide of interest. In a preferred embodiment, the inclusion body tag is insoluble in an aqueous solution while the protein/polypeptide of interest is appreciably soluble in an aqueous solution. The pH, temperature, and/or ionic strength of the aqueous solution can be adjusted to facilitate recovery of the peptide of interest. In a preferred embodiment, the differential solubility between the inclusion body tag and the peptide of interest occurs in an aqueous solution having a pH of 5 to 10 and a temperature range of 15° C. to 50° C. The cleavable peptide linker may be from 1 to about 50 amino acids, preferably from 1 to about 20 amino acids in length. An example of an enzymatically cleavable peptide linker is provided by SEQ ID NO: 261 (Caspase-3 cleavage sequence). In a preferred embodiment, the cleavage site is an acid cleavable aspartic acid-proline dipeptide (D-P) moiety. The cleavable peptide linkers may be incorporated into the fusion proteins using any number of techniques well known in the art. In a further embodiment, the present inclusion body tag comprises an effective number of cross-linkable cysteine residues whereby oxidative cross-linking can be used to selective precipitate the IBT once cleaved from the POI (co-pending U.S. Provisional Patent Application No. 60/951,754 entitled "Recombinant Peptide Production Using A Cross-Linkable Solubility Tag").

As used herein, the terms "effective number of cysteine residues" and "effective number of cross-linkable cysteine residues" are used to describe the number of cysteine residues required to obtain oxidative cross-linking when the IBTs are subjected to oxidizing conditions. One of skill in the art will recognize that the use of oxidative cross-linking to selectively precipitate the IBT from the POI (post cleavage of the fusion peptide) will require a POI that is devoid of cysteine residues. It is well within the skill of one in the art to vary the number and/or location of the cysteine residues within the fusion peptide to practice the present process. In one embodiment, the effective number of cysteine residues is at least 3, preferably at least 4. In another embodiment, the effective number of cysteine residues is 3 to about 20, preferably 3 to about 10, more preferably 4 to about 6, more preferably 4 to about 5, and most preferably 4 cross-linkable cysteine residues.

As used herein, the terms "cross-linking", "oxidative cross-linking", and "cysteine cross-linking" refers to the process of cross-linking the thiol groups of cysteine residues (i.e. forming intermolecular and intramolecular disulfide bonds) under oxidizing conditions. By definition, the formation of intermolecular disulfide bonds occurs between two or more molecules (i.e. a "plurality") comprising an effective number cross-linkable cysteine residues. As used herein, a "plurality" of molecules will alternatively be referred to herein as a "population" of molecules. In order to promoter intermolecular cross-linking, an effective number (i.e. at least 3) cross-linkable cysteine residues are incorporated into the inclusion body tag with the proviso that the portion comprising the POI is devoid of cross-linkable cysteine residues. In a preferred embodiment, the cross-linkable cysteine residues are engineered into the inclusion body tag so that the peptide of interest (which does not contain a cross-linkable cysteine residue) is isolated as a soluble peptide from the insoluble, cross-linked, inclusion body tags.

As used herein, the term "oxidizing conditions" refers to reaction conditions which favor and promoter the formation of disulfide bonds between cysteine residues. Disulfide bond formation can be induced by any number of means well known in the art including, but not limited to contacting the cross-linkable cysteine residues with a gas comprised of oxygen (i.e. diatomic and/or triatomic oxygen) and/or the addition of chemical oxidants. The use of gas comprising molecular oxygen is preferred. In a further embodiment, a gas comprising diatomic and/or triatomic oxygen is bubbled and/or sparged through the aqueous reaction solution for a period of time to achieve effective oxidative cross-linking. The oxidative cross-linking step may optionally include the act of mixing and/or stirring of the aqueous reaction mixture for optimal results. Examples of chemical oxidants are well-known in the art and may include, but are not limited to peroxide compounds, hypochlorite, halogens, and permanganate salts; to name a few.

As used herein, the term "reducing conditions" refers to reaction conditions which favor and promoter the reduction of disulfide bonds between cysteine residues (i.e. breaks disulfide bond used for cross-linking). Disulfide bonds can be reduced by any number of means well known such as the use of nitrogen purge and/or a chemical reducing agent such as $Na_2SO_3$, DTT (dithiothreitol), TCEP (tris(2-carboxyethyl) phosphine), 2-mercaptoethanol, 2-mercaptoethylamine, and mixtures thereof. Generally reducing agents include those that contain thiol groups, those that are phosphines and their derivatives as well as sulfites and thiosulfites.

As used herein, the term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). In a further embodiment, the definition of "operably linked" may also be extended to describe the products of chimeric genes, such as fusion peptides. As such, "operably linked" will also refer to the linking of an inclusion body tag to a peptide of interest to be produced and recovered. The inclusion body tag is "operably linked" to the peptide of interest if upon expression the fusion protein is insoluble and accumulates as inclusion bodies in the expressing host cell.

As used herein, the terms "fusion protein", "fusion peptide", "chimeric protein", and "chimeric peptide" will be used interchangeably and will refer to a polymer of amino acids (peptide, oligopeptide, polypeptide, or protein) comprising at least two portions, each portion comprising a distinct function. At least one first portion of the fusion peptide comprises at least one of the present inclusion body tags. At least one second portion of the fusion peptide comprises at least one peptide of interest.

Means to prepare the present peptides (inclusion body tags, cleavable peptide linkers, peptides of interest, spacer peptides, and fusion peptides) are well known in the art (see, for example, Stewart et al., Solid Phase Peptide Synthesis, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). The various components of the fusion peptides (inclusion body tag, peptide of interest, and the cleavable linker/cleavage sequence) described herein can be combined using carbodiimide coupling agents (see for example, Hermanson, Greg T., *Bioconjugate Techniques*, Academic Press, New York (1996)), diacid chlorides, diisocyanates and other difunctional coupling reagents that are reactive to terminal amine and/or carboxylic acid groups on the peptides. However, chemical synthesis is often limited to peptides of less than about 50 amino acids length due to cost and/or impurities. In a preferred embodiment, the biological molecules (IBTs, POIs, fusion peptides, etc) described herein are prepared using standard recombinant DNA and molecular cloning techniques.

As used herein, the terms "polypeptide" and "peptide" will be used interchangeably to refer to a polymer of two or more amino acids joined together by a peptide bond, wherein the peptide is of unspecified length, thus, peptides, oligopeptides, polypeptides, and proteins are included within the present definition. In one aspect, this term also includes post expression modifications of the polypeptide, for example, glycosylations, acetylations, phosphorylations and the like. Included within the definition are, for example, peptides containing one or more analogues of an amino acid or labeled amino acids and peptidomimetics. In a preferred embodiment, the present IBTs are comprised of L-amino acids.

As used herein, the terms "protein of interest", "polypeptide of interest", "peptide of interest", "targeted protein", "targeted polypeptide", "targeted peptide", "expressible protein", and "expressible polypeptide" will be used interchangeably and refer to a protein, polypeptide, or peptide that is bioactive and may be expressed by the genetic machinery of a host cell.

As used herein, the term "bioactive" or "peptide of interest activity" refers to the activity or characteristic associated with the peptide and/or protein of interest. The bioactive peptides may be used in a variety of applications including, but not limited to curative agents for diseases (e.g., insulin, interferon, interleukins, anti-angiogenic peptides (U.S. Pat. No. 6,815,426), and polypeptides that bind to defined cellular targets (with the proviso that the peptide of interest is not an antibody or the $F_{ab}$ fragment of an antibody) such as receptors, channels, lipids, cytosolic proteins, and membrane proteins, to name a few), peptides having antimicrobial activity, peptides having an affinity for a particular material (e.g., hair binding polypeptides, skin binding polypeptides, nail binding polypeptides, cellulose binding polypeptides, polymer binding polypeptides, clay binding polypeptides, silicon binding polypeptides, carbon nanotube binding polypeptides, and peptides that have an affinity for particular animal or plant tissues) for targeted delivery of benefit agents. The peptide of interest is typically no more than 300 amino acids in length, preferably less than 200 amino acids in length, and most preferably less than 100 amino acids in length. In a preferred embodiment, the peptide of interest is a peptide selected from a combinatorially generated library wherein the peptide is selected based on a specific affinity for a target substrate.

As used herein, the "benefit agent" refers to a molecule that imparts a desired functionality to a complex involving the peptide of interest for a defined application. The benefit agent may be peptide of interest itself or may be one or more molecules bound to (covalently or non-covalently), or associated with, the peptide of interest wherein the binding affinity of the targeted polypeptide is used to selectively target the benefit agent to the targeted material. In another embodiment, the targeted polypeptide comprises at least one region having an affinity for at least one target material (e.g., biological molecules, polymers, hair, skin, nail, clays, other peptides, etc.) and at least one region having an affinity for the benefit agent (e.g., pharmaceutical agents, pigments, conditioners, dyes, fragrances, etc.). In another embodiment, the peptide of interest comprises a plurality of regions having an affinity for the target material and a plurality of regions having an affinity for the benefit agent. In yet another embodiment, the peptide of interest comprises at least one region having an affinity for a targeted material and a plurality of regions having an affinity for a variety of benefit agents wherein the benefit agents may be the same of different. Examples of benefits agents may include, but are not limited to conditioners for personal care products, pigments, dyes, fragrances, pharmaceutical agents (e.g., targeted delivery of cancer treatment agents), diagnostic/labeling agents, ultraviolet light blocking agents (i.e., active agents in sunscreen protectants), and antimicrobial agents (e.g., antimicrobial peptides), to name a few.

As used herein, an "inclusion body" is an intracellular amorphous deposit comprising aggregated protein found in the cytoplasm of a cell. Peptides of interest that are typically soluble with the host cell and/or cell lysates can be fused to one or more of the present inclusion body tags to facilitate formation of an insoluble fusion protein. In an alternative embodiment, the peptide of interest may be partially insoluble in the host cell, but produced at relatively lows levels where significant inclusion body formation does not occur. As such, the formation of inclusion bodies will increase peptide production. In a further embodiment, fusion of the peptide of interest to one or more inclusion body tags (IBTs) increases the amount of protein produced in the host cell. Formation of the inclusion body facilitates simple and efficient purification of the fusion peptide from the cell lysate using techniques well known in the art such as centrifugation and filtration. In another embodiment, the inclusion body tag comprises an effective number of cross-linkable cysteine residues useful for separating the IBT from the peptide of interest (post cleavage into a mixture of peptide fragments) with the proviso that the peptide of interest is devoid of cysteine residues. The fusion protein typically includes one or more cleavable peptide linkers used to separate the protein/polypeptide of interest from the inclusion body tag(s). The cleavable peptide linker is designed so that the inclusion body tag(s) and the protein/polypeptide(s) of interest can be easily separated by cleaving the linker element. The peptide linker can be cleaved chemically (e.g., acid hydrolysis) or enzymatically (i.e., use of a protease/peptidase that preferentially recognizes an amino acid cleavage site and/or sequence within the cleavable peptide linker).

"Codon degeneracy" refers to the nature in the genetic code permitting variation of the nucleotide sequence without affecting the amino acid sequence of an encoded polypeptide. Accordingly, the instant invention relates to any nucleic acid fragment that encodes the present amino acid sequences. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, the term "solubility" refers to the amount of a substance that can be dissolved in a unit volume of a liquid under specified conditions. In the present application, the term "solubility" is used to describe the ability of a peptide (inclusion body tag, peptide of interest, or fusion peptides) to be resuspended in a volume of solvent, such as a biological buffer. In one embodiment, the peptides targeted for production ("peptides of interest") are normally soluble in the cell and/or cell lysate under normal physiological conditions. Fusion of one or more inclusion body tags (IBTs) to the target peptide results in the formation of a fusion peptide that is insoluble under normal physiological conditions, resulting in the formation of inclusion bodies. In one embodiment, the peptide of interest is insoluble in an aqueous matrix having a pH range of 5-12, preferably 6-10; and a temperature range of 5° C. to 50° C., preferably 10° C. to 40° C.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any naturally-occurring amino acid (or as defined by the formulas described herein) | Xaa | X |

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences "Chimeric gene" refers to any gene that is not a native gene, comprising regulatory and coding sequences (including coding regions engineered to encode fusion peptides) that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes.

As used herein, the term "coding sequence" refers to a DNA sequence that encodes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, ribosomal binding sites, translation leader sequences, introns, polyadenylation recognition sequences, RNA processing site, effector binding sites, and stem-loop structures. One of skill in the art recognizes that selection of suitable regulatory sequences will depend upon host cell and/or expression system used.

As used herein, the term "genetic construct" refers to a series of contiguous nucleic acids useful for modulating the genotype or phenotype of an organism. Non-limiting examples of genetic constructs include but are not limited to a nucleic acid molecule, and open reading frame, a gene, a plasmid and the like.

As used herein, the term "expression ranking" means the relative yield of insoluble fusion protein estimated visually and scored on a relative scale of 0 (no insoluble fusion peptide) to 3 (highest yield of insoluble fusion peptide). Any number of means may be used by one of skill in the art to assess inclusion body formation with a recombinant host cell. As described in the present examples, the relative yield of insoluble fusion peptide was estimated visually from stained polyacrylamide gels. Any IBT capable of generating an expression ranking above zero (i.e. 1, 2, or 3) is considered to be an effective solubility tag. Conversely, effective solubility tags may also be identified using a qualitative assessment (i.e. observed inclusion bodies).

As used herein, the term "host cell" refers to cell which has been transformed or transfected, or is capable of transformation or transfection by an exogenous polynucleotide sequence.

As used herein, the terms "plasmid", "vector" and "cassette" refer to an extrachromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5$^{th}$ Ed. Current Protocols and John Wiley and Sons, Inc., N.Y., 2002.

Inclusion Body Tags

Amyloid-like proteins tend to have amyloid fibrillar morphologies and the aggregated proteins often exhibit β-sheet tape architecture. An 11 amino acid synthetic peptide (i.e. peptide "PII-2"; also known as peptide "DN1") capable of self-assembly into β-sheet tapes, ribbons, fibrils, and fibers in water has been described (Aggeli et al., *J. Amer. Chem. Soc.*, 125:9619-9628 (2003); Aggeli et al., *PNAS*, 98(21):11857-11862 (2001); Aggeli et al., *Nature*, 386:259-262 (1997); and Aggeli et al., *J. Mater Chem*, 7(7):1135-1145 (1997).

The P11-2 peptide (identical to IBT-136; SEQ ID NO: 17) was selected as the starting material for preparation of a family of structurally-related inclusion body tags comprising at least two copies of the core sequence Gln-Gln-Xaa1-Phe-Xaa2-Trp-Xaa3-Phe-Xaa4-Xaa5-Gln (SEQ ID NO: 58) wherein Xaa1=Arg, His, or Lys; Xaa2=Gln, His, or Lys; Xaa3=Gln, His, or Lys; Xaa4=Glu or Gln; and Xaa5=Gln or Lys (see bolded portion of Formula 1, below).

A series of IBT-136 analogues were prepared and evaluated. Several approaches were taken including varying copy number, altering the charge of the tag, altering the composition of the spacer elements separating the core sequences, and altering the number of cross-linkable cysteine residues/moieties. A short spacer sequence was inserted between the core sequences. In one embodiment, the "spacer" of Formula 1 is a peptide of 2 to 10 amino acids length, preferably 3 to 6 amino acids in length, and most preferably 3 to 4 amino acids in length and is comprised of amino acids selected from the group consisting of proline, glycine, cysteine, arginine, and glutamic acid. In a further embodiment, the "spacer" sequences are selected from the group consisting of Pro-Arg-Gly, Pro-Cys-Gly, Pro-Arg-Cys-Gly (SEQ ID NO: 56), Pro-Glu-Gly, and Pro-Glu-Cys-Gly (SEQ ID NO: 57).

The structure of the present inclusion body tags is defined by Formula 1 (3-letter abbreviations of the various amino acids are used unless otherwise noted).

```
Formula 1.
                                    (SEQ ID NO: 262)
Gln-Gln-Xaa1-Phe-Xaa2-Trp-Xaa3-Phe-Xaa4-Xaa5-Gln- Spacer-[[Gln-Gln-Xaa1-Phe-Xaa2-Trp-Xaa3-Phe-Xaa4-

Xaa5-Gln]-[Spacer]_m]_n
``` wherein
   Xaa1=Arg, His, or Lys;
   Xaa2=Gln, His, or Lys;
   Xaa3=Gln, His, or Lys;
   Xaa4=Glu or Gln;
   Xaa5=Gln or Lys;
   n=1 to 10;
   m=n−1; and
   wherein the Spacer=is a peptide comprising amino acids selected from the group consisting of proline, arginine, glycine, glutamic acid, and cysteine.

In a preferred embodiment, n=1 to 3.

Each of the present inclusion body tags was operably linked to a short peptide of interest (POI) that is appreciably soluble in the host cell under normal physiological conditions. The resulting fusion proteins/peptides were produced as insoluble inclusion bodies. Each fusion peptide was recombinantly expressed in an appropriate host cell and evaluated for insoluble fusion peptide formation. Means to determine inclusion body formation are known in the art including, but not limited to gel separation and analysis techniques (e.g., SDS-PAGE).

In another embodiment, the inclusion body tag further comprises at least one cross-linkable cysteine moiety (CCPGCC; SEQ ID NO: 33). In a further embodiment, the at least one cross-linkable cysteine moiety is located on the amino and/or carboxy terminus of the inclusion body tag defined by Formula 1.

In another embodiment, the inclusion body tag is selected from the group consisting of IBT103 (SEQ ID NO: 15), IBT138 (SEQ ID NO: 19), IBT 139 (SEQ ID NO: 21), IBT138.CCPGCC (SEQ ID NO: 31), IBT 182 (SEQ ID NO: 39), IBT 183 (SEQ ID NO: 41), IBT184 (SEQ ID NO: 43), IBT185 (SEQ ID NO: 45), IBT 186 (SEQ ID NO: 27), IBT 187a (SEQ ID NO: 47), and IBT187b (SEQ ID NO: 49). A CLUSTALW alignment of the present inclusion body tags is provided in FIG. 1 (the repeated core sequence is underlined).

In another embodiment, an insoluble fusion protein is provided comprising at least one of present inclusion body tags (IBT) operably linked to a peptide of interest (POI) and separated by at least once cleavable peptide linker sequence (CS). In a preferred aspect, the cleavable peptide linker (CS) comprises at least one acid cleavable aspartic acid-proline (Asp-Pro) moiety.

IBT-CS-POI
      or
   POI-CS-IBT

In another embodiment, the fusion peptide comprises an inclusion body tag comprising an effective number of cross-linkable cysteine residues. As described in co-pending U.S. Provisional Patent Application No. 60/951,754 entitled "Recombinant Peptide Production Using a Cross-Linkable Solubility Tag", the inclusion of an effective number of cross-linkable cysteine residues is useful to selectively precipitate and separate the inclusion body tag from the peptide of interest during processing. Upon cleavage of the fusion peptide, the mixture of fragments (IBTs and POIs) is subjected to oxidizing conditions for a period of time sufficient to cross-link the effective number of cysteine residues incorporated into the IBT. The oxidative cross-linking selectively precipitates the IBTs from the soluble peptide of interest with the proviso that the peptide of interest is devoid of cross-linkable cysteine residues.

IBTs comprising cysteine residues may be effectively used a solubility tags in combination with a peptide of interest having cross-linkable cysteine residues. However, in such situations an oxidative-cross linking step will typically be omitted during subsequent POI isolation.

Expressible Peptides of Interest

The peptide of interest ("expressible peptide") targeted for production using the present method is one that is appreciably soluble in the host cell and/or host cell liquid lysate under normal physiological conditions. In a preferred aspect, the peptides of interest are generally short (<300 amino acids in length) and difficult to produce in sufficient amounts due to proteolytic degradation. Fusion of the peptide of interest to at least one of the present inclusion body forming tags creates a fusion peptide that is insoluble in the host cell and/or host cell lysate under normal physiological conditions. Production of the peptide of interest is typically increased when expressed and accumulated in the form of an insoluble inclusion body as the peptide is generally more protected from proteolytic degradation. Furthermore, the insoluble fusion protein can be easily separated from the host cell lysate using centrifugation or filtration.

In general, the present inclusion body tags can be used in a process to produce any peptide of interest that is (1) typically soluble in the cell and/or cell lysate under typical physiological conditions and/or (2) those that can be produced at significantly higher levels when expressed in the form of an inclusion body. In a preferred embodiment, the peptide of interest is appreciably soluble in the host cell and/or corresponding cell lysate under normal physiological and/or process conditions.

The length of the peptide of interest may vary as long as (1) the peptide is appreciably soluble in the host cell and/or cell lysate, and/or (2) the amount of the targeted peptide produced is significantly increased when expressed in the form of an insoluble fusion peptide/inclusion body (i.e. expression in the form of a fusion protein protect the peptide of interest from proteolytic degradation). Typically the peptide of interest is less than 300 amino acids in length, preferably less than 100 amino acids in length, more preferably less than 75 amino acids in length, even more preferably less than 50 amino acids in length, and most preferably less than 25 amino acids in length.

The function of the peptide of interest is not limited by the present method and may include, but is not limited to bioactive molecules such as curative agents for diseases (e.g., insulin, interferon, interleukins, peptide hormones, anti-angiogenic peptides, and peptides (with the proviso that the peptide is not an antibody or an $F_{ab}$ portion of an antibody) that bind to and affect defined cellular targets such as receptors, channels, lipids, cytosolic proteins, and membrane proteins; see U.S. Pat. No. 6,696,089,), peptides having an affinity for a particular material (e.g., biological tissues, biological molecules, hair binding peptides (U.S. patent application Ser. No. 11/074,473; WO 0179479; U.S. Patent Application Publication No. 2002/0098524; U.S. Patent Application Publication No. 2003/0152976; WO 04048399; U.S. patent application Ser. No. 11/512,910; U.S. patent application Ser. No. 11/516, 362; and U.S. patent application Ser. No. 11/696,380), skin binding peptides (U.S. patent application Ser. No. 11/069, 858; WO 2004/000257; U.S. patent application Ser. No. 11/516,362; and U.S. patent application Ser. No. 11/696, 380), nail binding peptides (U.S. patent application Ser. No. 11/074,473; U.S. patent application Ser. No. 11/696,380), cellulose binding peptides, polymer binding peptides (U.S. patent application Ser. Nos. 11/607,723, 11/607,792, 11/607, 734, 11/607,672, and 11/607,673), and clay binding peptides (U.S. patent application Ser. No. 11/696,380), for targeted delivery of at least one benefit agent (see U.S. patent application Ser. No. 10/935,642; U.S. patent application Ser. No. 11/074,473; and U.S. patent application Ser. No. 11/696, 380).

In a preferred aspect, the peptide of interest is an affinity peptide identified from a combinatorially generated peptide library. In a further aspect, the peptide is selected from a combinatorially generated library wherein said library was prepared using a technique selected from the group consisting of phage display, yeast display, bacterial display, ribosomal display and mRNA display.

In a preferred aspect, the peptide of interest is selected from the group of hair binding peptides, skin binding peptides, nail binding peptides, antimicrobial peptides, pigment binding peptides, clay-binding peptides, and polymer binding peptides. In another preferred aspect, the peptide of interest is selected from the group consisting of a hair-binding peptide comprising an amino acid sequence selected from the group consisting of SEQ ID NOs: 3, 4, 5, 7, 9, 11, 13, 23, and 59-147, a skin binding peptide comprising an amino acid sequence selected from the group consisting of SEQ ID NOs: 148 to 155, and a nail binding peptide comprising an amino acid sequence selected from the group consisting of SEQ ID NOs: 156 and 157. In a further embodiment, the peptide of interest is a multi-block hair-binding peptide. Examples of multi-block hair-binding peptides include, but are not limited to HC77607 (SEQ ID NO: 7), HC77638 (SEQ ID NO: 9), HC77643 (SEQ ID NO: 11), HC77681 (SEQ ID NO: 13), and HC776124 (SEQ ID NO: 23).

Affinity peptides are particularly useful to target benefit agents imparting a desired functionality to a target material (e.g., hair, skin, etc.) for a defined application (U.S. patent application Ser. No. 10/935,642; U.S. Patent application Ser. No. 11/074,473; U.S. patent application Ser. No. 11/512,910; and U.S. patent application Ser. No. 11/696,380 for a list of typical benefit agents such as conditioners, pigments/colorants, fragrances, etc.). The benefit agent may be peptide of interest itself or may be one or more molecules bound to (covalently or non-covalently), or associated with, the peptide of interest wherein the binding affinity of the peptide of interest is used to selectively target the benefit agent to the targeted material. In another embodiment, the peptide of interest comprises at least one region having an affinity for at least one target material (e.g., biological molecules, polymers, hair, skin, nail, other peptides, etc.) and at least one region having an affinity for the benefit agent (e.g., pharmaceutical agents, antimicrobial agents, pigments, conditioners, dyes, fragrances, etc.). In another embodiment, the peptide of interest comprises a plurality of regions having an affinity for the target material and a plurality of regions having an affinity for one or more benefit agents. In yet another embodiment, the peptide of interest comprises at least one region having an affinity for a targeted material and a plurality of regions having an affinity for a variety of benefit agents wherein the benefit agents may be the same of different. Examples of benefits agents may include, but are not limited to conditioners for personal care products, pigments, dye, fragrances, pharmaceutical agents (e.g., targeted delivery of cancer treatment agents), diagnostic/labeling agents, ultraviolet light blocking agents (i.e., active agents in sunscreen protectants), and antimicrobial agents (e.g., antimicrobial peptides), to name a few.

Cleavable Peptide Linkers

The use of cleavable peptide linkers (i.e. cleavage sites or cleavage sequences) is well known in the art. Fusion peptides comprising the present inclusion body tags will typically include at least one cleavable sequence separating the inclusion body tag from the polypeptide of interest. The cleavable sequence facilitates separation of the inclusion body tag(s) from the peptide(s) of interest. In one embodiment, the cleavable sequence may be provided by a portion of the inclusion body tag and/or the peptide of interest (e.g., inclusion of an acid cleavable aspartic acid-proline moiety). In a preferred embodiment, the cleavable sequence is provided by including (in the fusion peptide) at least one cleavable peptide linker between the inclusion body tag and the peptide of interest.

Means to cleave the peptide linkers are well known in the art and may include chemical hydrolysis, enzymatic cleavage agents, and combinations thereof. In one embodiment, one or more chemically cleavable peptide linkers are included in the fusion construct to facilitate recovery of the peptide of interest from the inclusion body fusion protein. Examples of chemical cleavage reagents include cyanogen bromide (cleaves methionine residues), N-chloro succinimide, iodobenzoic acid or BNPS-skatole [2-(2-nitrophenylsulfenyl)-3-methylindole] (cleaves tryptophan residues), dilute acids (cleaves at aspartyl-prolyl bonds), and hydroxylamine (cleaves at asparagine-glycine bonds at pH 9.0); see Gavit, P. and Better, M., *J. Biotechnol.*, 79:127-136 (2000); Szoka et al., *DNA*, 5(1):11-20 (1986); and Walker, J. M., *The Proteomics Protocols Handbook*, 2005, Humana Press, Totowa, N.J.)). In a preferred embodiment, one or more aspartic acid-proline acid cleavable recognition sites (i.e., a cleavable peptide linker comprising one or more D-P dipeptide moieties) are included in the fusion protein construct to facilitate separation of the inclusion body tag(s) form the peptide of interest. In another embodiment, the fusion peptide may include multiple regions encoding peptides of interest separated by one or more cleavable peptide linkers.

In another embodiment, one or more enzymatic cleavage sequences are included in the fusion protein construct to facilitate recovery of the peptide of interest. Proteolytic enzymes and their respective cleavage site specificities are well known in the art. In a preferred embodiment, the proteolytic enzyme is selected to specifically cleave only the peptide linker separating the inclusion body tag and the peptide of interest. Examples of enzymes useful for cleaving the peptide linker include, but are not limited to Arg-C proteinase, Asp-N endopeptidase, chymotrypsin, clostripain, enterokinase, Factor Xa, glutamyl endopeptidase, Granzyme B, Achromobacter proteinase I, pepsin, proline endopeptidase, proteinase K, Staphylococcal peptidase I, thermolysin, thrombin, trypsin, and members of the Caspase family of proteolytic enzymes (e.g. Caspases 1-10) (Walker, J. M., supra). An example of a cleavage site sequence is provided by SEQ ID NO: 261 (Caspase-3 cleavage site; Thornberry et al. *J. Biol. Chem.*, 272:17907-17911 (1997) and Tyas et al., *EMBO Reports*, 1(3):266-270 (2000)).

Typically, the cleavage step occurs after the insoluble inclusion bodies and/or insoluble fusion peptides are isolated from the cell lysate. The cells can be lysed using any number of means well known in the art (e.g. mechanical and/or chemical lysis). Methods to isolate the insoluble inclusion bodies/fusion peptides from the cell lysate are well known in the art (e.g., centrifugation, filtration, and combinations thereof). Once recovered from the cell lysate, the insoluble inclusion bodies and/or fusion peptides can be treated with a cleavage agent (chemical or enzymatic) to cleavage the inclusion body tag from the peptide of interest. In one embodiment, the fusion protein and/or inclusion body is diluted and/or dissolved in a suitable solvent prior to treatment with the cleavage agent. In a further embodiment, the cleavage step may be omitted if the inclusion body tag does not interfere with the activity of the peptide of interest.

After the cleavage step, and in a preferred embodiment, the peptide of interest can be separated and/or isolated from the fusion protein and the inclusion body tags based on a differential solubility of the components. Parameters such as pH, salt concentration, and temperature may be adjusted to facilitate separation of the inclusion body tag from the peptide of interest. In one embodiment, the peptide of interest is soluble while the inclusion body tag and/or fusion protein is insoluble in the defined process matrix (typically an aqueous matrix). In another embodiment, the peptide of interest is insoluble while the inclusion body tag is soluble in the defined process matrix.

In a preferred embodiment, the inclusion body tag comprises an effective number of cross-linkable cysteine residues with the proviso that the peptide of interest is devoid of cysteine residues (See co-pending U.S. Provisional Patent Application No. 60/951,754 entitled "Recombinant Peptide Production Using a Cross-Linkable Solubility Tag". Upon cleavage, oxidative cross-linking is used to selective cross-link the IBTs (typically insoluble). The conditions are controlled so that the cross-linked IBTs are insoluble while the peptide of interest remains soluble. The soluble peptide of interest is subsequently separated from the cross-linked IBTs using a simple separation technique such as centrifugation and/or filtration.

In an optional embodiment, the peptide of interest may be further purified using any number of well known purification techniques in the art such as ion exchange, gel purification techniques, and column chromatography (see U.S. Pat. No. 5,648,244), to name a few.

Fusion Peptides

The present inclusion body tags are used to create chimeric polypeptides ("fusion peptides" or "fusion proteins") that are insoluble within the host cell, forming inclusion bodies. Synthesis and expression of expressible genetic constructs encoding the present fusion peptides is well known to one of skill in the art given the present inclusion body tags.

The present fusion peptides will include at least one of the present inclusion body tags (IBTs) operably linked to at least one peptide of interest. Typically, the fusion peptides will also include at least one cleavable peptide linker having a cleavage site between the inclusion body tag and the peptide of interest. In one embodiment, the inclusion body tag may include a cleavage site whereby inclusion of a separate cleavable peptide linker may not be necessary. In a preferred embodiment, the cleavage method is chosen to ensure that the peptide of interest is not adversely affected by the cleavage agent(s) employed. In a further embodiment, the peptide of interest may be modified to eliminate possible cleavage sites with the peptide so long as the desired activity of the peptide is not adversely affected.

One of skill in the art will recognize that the elements of the fusion protein can be structured in a variety of ways. Typically, the fusion protein will include at least one IBT, at least one peptide of interest (POI), and at least one cleavable peptide linker (CL) comprising a cleavage site (CS) located between the IBT and the POI. The inclusion body tag may be organized as a leader sequence or a terminator sequence relative to the position of the peptide of interest within the fusion peptide. In another embodiment, a plurality of IBTs, POIs, and CLs are used when engineering the fusion peptide. In a further embodiment, the fusion peptide may include a plurality of IBTs (as defined herein), POIs, and CLs that are the same or different.

The fusion peptide should be insoluble in an aqueous matrix at a temperature of 10° C. to 50° C., preferably 10° C. to 40° C. The aqueous matrix typically comprises a pH range of 5 to 12, preferably 6 to 10, and most preferably 6 to 8. The temperature, pH, and/or ionic strength of the aqueous matrix can be adjusted to obtain the desired solubility characteristics of the fusion peptide/inclusion body.

Method to Make a Peptide of Interest Using Insoluble Fusion Peptides

The present inclusion body tags are used to make fusion peptides that form inclusion bodies within the production host. This method is particularly attractive for producing significant amounts of soluble peptide of interest that (1) are difficult to isolation from other soluble components of the cell lysate and/or (2) are difficult to product in significant amounts within the target production host.

In the present methods, a peptide of interest is fused to at least one of the present inclusion body tags, forming an insoluble fusion protein. Expression of the genetic construct encoding the fusion protein produces an insoluble form of the peptide of interest that accumulates in the form of inclusion bodies within the host cell. The host cell is grown for a period of time sufficient for the insoluble fusion peptide to accumulate within the cell.

The host cell is subsequently lysed using any number of techniques well known in the art. The insoluble fusion peptide/inclusion bodies are then separated from the soluble components of the cell lysate using a simple and economical technique such as centrifugation and/or membrane filtration.

The insoluble fusion peptide/inclusion body can then be further processed in order to isolate the peptide of interest. Typically, this will include resuspension of the fusion peptide/inclusion body in a liquid matrix suitable for cleaving the fusion peptide, separating the inclusion body tag from the peptide of interest. The fusion protein is typically designed to include a cleavable peptide linker separating the inclusion body tag from the peptide of interest. The cleavage step can be conducted using any number of techniques well known in the art (chemical cleavage, enzymatic cleavage, and combinations thereof). The peptide of interest can then be separated from the inclusion body tag(s) and/or fusion peptides using any number of techniques well known in the art (centrifugation, filtration, precipitation, column chromatography, etc.). Preferably, the peptide of interest (once cleaved from fusion peptide) has a solubility that is significantly different than that of the inclusion body tag and/or remaining fusion peptide. In a further preferred embodiment, oxidative cross-linking is used to selective precipitate the IBT (comprising an effective number of cross-linkable cysteine residues) from the peptide of interest (when devoid of cross-linkable cysteine residues). As shown herein, derivatives of IBT-136 (i.e. IBT139.CCPGCC, IBT185, and IBT186) were designed to include an effective number of cross-linkable cysteine residues.

Transformation and Expression

Once the inclusion body tag has been identified and paired with the appropriate peptide of interest, construction of cassettes and vectors that may be transformed in to an appropriate expression host is common and well known in the art. Typically, the vector or cassette contains sequences directing transcription and translation of the relevant chimeric gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Transcription initiation control regions or promoters, which are useful to drive expression of the genetic constructs encoding the fusion peptides in the desired host cell, are numerous and familiar to those skilled in the art. Virtually any promoter capable of driving these constructs is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara (pBAD), tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary; however, it is most preferred if included.

Preferred host cells for expression of the present fusion peptides are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid molecules encoding the fusion peptides. Because of transcription, translation, and the protein biosynthetic apparatus is the same irrespective of the cellular feedstock, genes are expressed irrespective of the carbon feedstock used to generate the cellular biomass. Large-scale microbial growth and functional gene expression may utilize a wide range of simple or complex carbohydrates, organic acids and alcohols (i.e. methanol), saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include, but are not limited to fungal or yeast species such as *Aspergillus, Trichoderma, Saccharomyces, Pichia, Yarrowia, Candida, Hansenula*, or bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. Preferred bacterial host strains include *Escherichia, Pseudomonas*, and *Bacillus*. In a highly preferred aspect, the bacterial host strain is *Escherichia coli*.

Fermentation Media

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the expression of the present fusion peptides.

Culture Conditions

Suitable culture conditions can be selected dependent upon the chosen production host. Typically, cells are grown at a temperature in the range of about 25° C. to about 40° C. in an appropriate medium. Suitable growth media may include common, commercially-prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are typically between pH 5.0 to pH 9.0, where pH 6.0 to pH 8.0 is preferred.

Fermentations may be performed under aerobic or anaerobic conditions where aerobic conditions are generally preferred.

Industrial Batch and Continuous Fermentations

A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass. (hereinafter "Brock"), or Deshpande, Mukund V., *Appl. Biochem. Biotechnol.*, 36:227 (1992).

Although the present invention is typically performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmol" means micromole(s), "pmol" means picomole(s), "g" means gram(s), "µg" means microgram(s), "mg" means milligram(s), "g" means the gravitation constant, "rpm" means revolutions per minute, "DTT" means dithiothreitol, and "cat#" means catalog number.

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5$^{th}$ Ed. Current Protocols and John Wiley and Sons, Inc., N.Y., 2002.

Materials and Methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or in Brock (supra). All reagents, restriction enzymes and materials used for the growth and maintenance of bacterial cells were obtained from BD Diagnostic Systems (Sparks, Md.), Invitrogen (Carlsbad, Calif.), Life Technologies (Rockville, Md.), QIAGEN (Valencia, Calif.) or Sigma-Aldrich Chemical Company (St. Louis, Mo.), unless otherwise specified.

Example 1

Construction of Expression Plasmids

Several expression systems were used to produce the fusion proteins in an *E. coli* host cell. One expression system was based on *E. coli* strain BL21-AI (Invitrogen) in combination with a T7-based expression vector (pLX121; SEQ ID NO: 1; FIG. 2) wherein expression of the T7 RNA polymerase is controlled by the araBAD promoter. Another expression system was based on *E. coli* MG1655 (ATCC 46076™) derived strain in combination with a pBAD-based expression vector (pSF032, FIG. 3, SEQ ID NO: 2 and pLR186, FIG. 4, SEQ ID NO: 51) wherein the endogenous chromosomal copy of the araBAD operon was deleted (the modified *E. coli* MG1655 strain comprising a disruption in the endogenous araBAD operon is referred to herein as *E. coli* strain KK2000). The 3' region downstream and operably linked to the respective promoter in each of the vectors was designed to facilitate simple swapping of the DNA encoding the respective inclusion body tag and/or the peptide of interest. NdeI and BamHI restriction sites flanked the region encoding the inclusion body tag (IBT). BamHI and AscI restriction sites flanked the region encoding the peptide of interest (POI).

The nucleic acid molecules encoding the various fusion peptides were designed to include at least one region encoding an inclusion body tag (IBT) linked to a peptide of interest (POI). As described above, the nucleic acid molecules encoding the components of the fusion peptide was designed to include the appropriate NdeI/BamHI (region encoding the inclusion body tag) and BamHI/AscI restriction sites (region encoding the peptide of interest) to facilitate insertion in the expression vector. Insertion of the nucleic acid molecules created a chimeric gene encoding a fusion peptide operably linked to the respective promoter. The fusion peptide was designed to have an inclusion body tag (IBT) linked to a peptide of interest (POI) where the two components were separated by a cleavable peptide linker (CS; for example, an acid cleavable DP moiety):

Construction of pLX121 Expression Plasmid (T7-Based Expression):

A genetic construct was prepared for evaluating the performance of the inclusion body tags when fused to a soluble peptide of interest. A plasmid (pLX121; FIG. 2; SEQ ID NO: 1) containing a pBR322 origin of replication and the bla gene to confer ampicillin resistance was used. Expression of the chimeric gene was driven by a T7 promoter. Construction of this plasmid is previously described in co-pending U.S. patent application Ser. No. 11/516,362, herein incorporated by reference.

Briefly, the pLX121 expression vector was designed from the destination plasmid pDEST17 (Invitrogen. Carlsbad, Calif.). The expression vector was modified so that the chimeric gene encoding the fusion protein was expressed under the control of the T7 promoter. NdeI and BamHI restriction sites were used for easy swapping of the various inclusion body tags. BamHI and AscI restriction sites were used to facilitate swapping of various peptides of interest. The sequence encoding the junction between the inclusion body tag and the peptide of interest was designed to encode an acid cleavable D-P moiety.

Construction of Expression Vector pSF043

The vector pKSI(C4)-HC77623 was derived from the commercially available vector pDEST17 (Invitrogen). Construction of this vector has been previously described in co-pending U.S. patent application Ser. No. 11/389,948, herein incorporated by reference. It includes sequences derived from the commercially available vector pET31b (Novagen, Madison, Wis.) that encode a fragment of the enzyme ketosteroid isomerase (KSI; Kuliopulos, A. and Walsh, C. T., *J. Am. Chem. Soc.* 116:4599-4607 (1994)). The KSI fragment used as an inclusion body tag to promote partition of the peptides into insoluble inclusion bodies in *E. coli*. The nucleic acid molecule encoding the KSI sequence from pET31b was modified using standard mutagenesis procedures (Quick-Change II, Stratagene, La Jolla, Calif.) to include three additional cysteine codons, in addition to the one cysteine codon found in the wild type KSI sequence, resulting in the inclusion body tag KSI(C4) (SEQ ID NOs: 52 and 53). The plasmid pKSI(C4)-HC77623 was constructed using standard recombinant DNA methods well known to those skilled in the art. The BamHI and AscI restriction sites facilitated swapping of nucleic acid molecules encoding the various peptides of interest. The inserts were designed to encode an acid cleavable DP moiety useful in separating the inclusion body tag from the peptide of interest.

Figure 5:
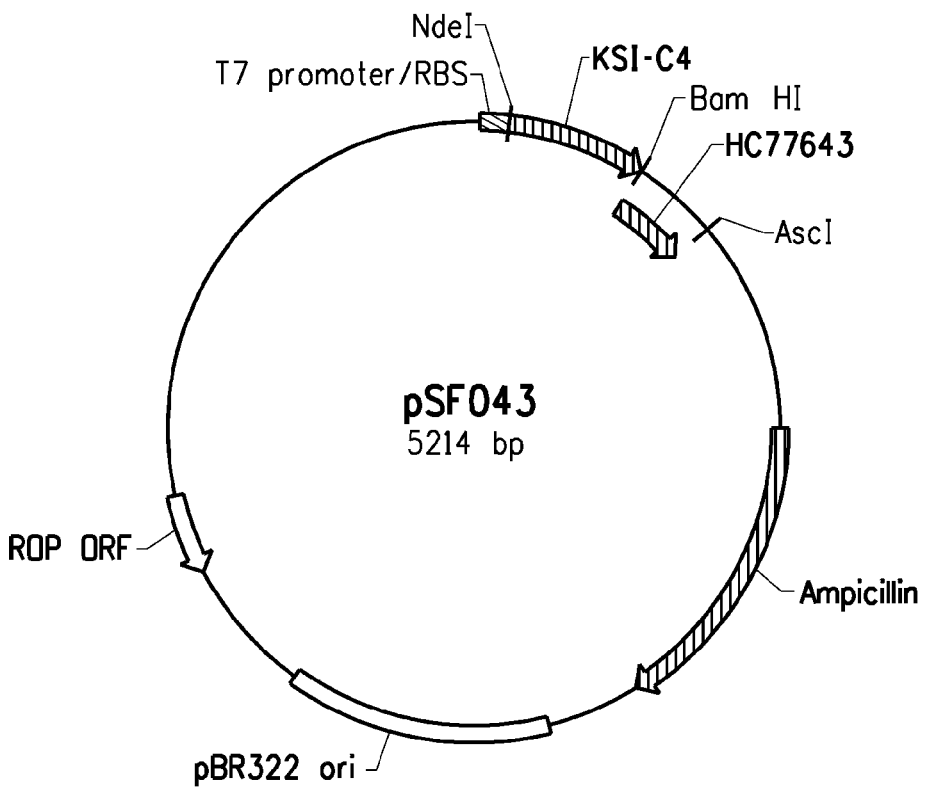
FIG. 5 is a diagram of expression plasmid pSF043.

The HC77643 gene was synthesized by DNA 2.0 with appropriate restriction sites on either end and cloned into the KSI(C4)-HC77623 vector as described above, creating pSF043 (SEQ ID NO: 50; FIG. 5). The sequences of the chimeric gene and the corresponding gene product (fusion peptide KSI(C4)-HC77643) are provided as SEQ ID NOs: 54 and 55, respectively).

Construction of pSF032 Expression Plasmid (pBAD-Based Expression)

Figure 3:
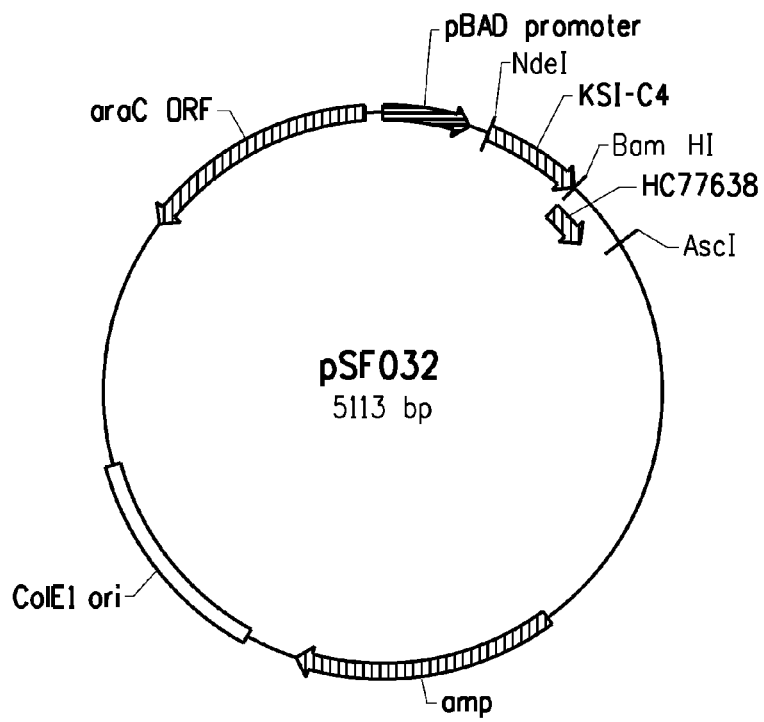
FIG. 3 is a diagram of expression plasmid pSF032.

Plasmid pSF032 (SEQ ID NO: 2; FIG. 3) contains a ColE1 type origin of replication and the bla gene to confer ampicillin resistance. The tag/peptide fusion construct is driven by the araBAD promoter. The plasmid also encodes the gene for the araC regulator.

Plasmid pSF032 was derived from the commercially available plasmid pBAD-HisA (Invitrogen). Briefly, a modified multiple cloning site (MCS) was cloned in pBAD-HisA and the NdeI restriction site at position 2844 was removed to create a single NdeI site downstream of the pBAD promoter. The resulting plasmid was named pBAD-HisA_MCSmod. The NdeI/EcoRI fragment of plasmid pKSIC4-HC77623 was inserted into the NdeI/EcoRI site of pBAD-HisA_MCSmod, creating plasmid pSF004_pBAD-KSIC4-HC77623. Plasmid pSF032 was created from plasmid pSF004 by removing the coding region for the HC77623 peptide and inserting the coding region for peptide HC77638 (see Example 2).

Figure 4:
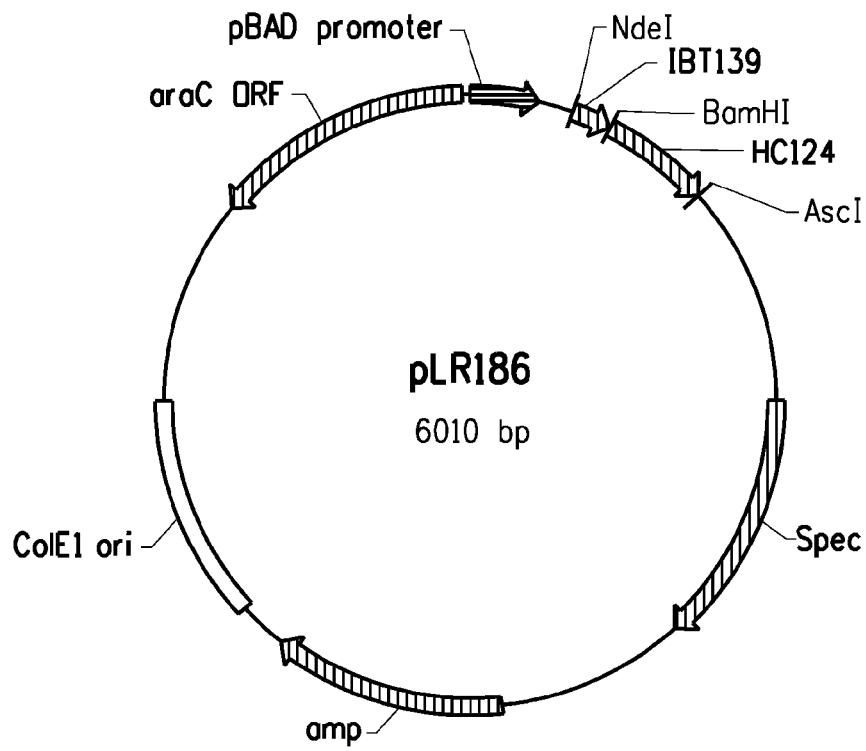
FIG. 4 is a diagram of expression plasmid pLR186.

Construction of pLR186 Expression Plasmid (araBAD Based Expression):

Plasmid pLR186 (SEQ ID NO: 51; FIG. 4) contains a ColE1 type origin of replication, the bla gene to confer ampicillin resistance and the aadA-1 gene to confer spectinomycin one or more hair binding domains. The functional binding domains are provided in Table 1. Hair-binding domains (bold) include A09 (IPWWNIRAPLNA; SEQ ID NO: 3; also found to bind to polymethylmethacrylate), KF11 (NTSQLST; SEQ ID NO: 4), and D21' (RTNAADHP; SEQ ID NO: 5). The affinity domains with the multi-block peptides are typically separated by short peptide spacers. The DP acid cleavable moieties are italicized.

TABLE 1

Soluble Peptides of Interest Used to Evaluate the Present Inclusion Body Tags

| Peptide Name | Formula (Functional Binding Domains in Bold) | Amino acid Sequence | Amino acid SEQ ID NO: | Nucleic Acid SEQ ID NO: |
|---|---|---|---|---|
| HC77607 | GSDP-KF11-GGG-D21'-KCGGG-KF11-GGG-D21'-KCGGG-KF11-GGG-D21'-KC | GS*DP*NTSQLSTGGGRTNAADHPKCGGGNTSQLSTGGG RTNAADHPKCGGGNTSQLSTGGGRTNAADHPKC | 6 | 7 |
| HC77638 | GS[DPG-KF11-GKG-KF11-GKG-KF11-GKGWG]$_2$D | GS*DP*GNTSQLSTGKGNTSQLSTGKGNTSQLSTGKGWG *DP*GNTSQLSTGKGNTSQLSTGKGNTSQLSTGKGWGD | 8 | 9 |
| HC77643 | GSDPG-A09-GAG-A09-GGSGPGSGG-KF11-GGG-KF11-GGPKK | GS*DP*GIPWWNIRAPLNAGAGIPWWNIRAPLNAGGSGPG SGGNTSQLSTGGGNTSQLST GGPKK | 10 | 11 |
| HC77681 | GSDP-KF11-GGGHGHQKQHGLGHGHK HGHGHGHGHGK | GS*DP*NTSQLSTGGGGHGHQKQHGLGHGHKHGHGHGH GHGK | 12 | 13 |

(Spec) resistance. The tag/peptide fusion construct is driven by the araBAD promoter. The plasmid also encodes the gene for the araC regulator.

Plasmid pLR186 was derived from the commercially available plasmid pBAD-HisA (Invitrogen). Briefly, a modified multiple cloning site (MCS) was cloned in pBAD-HisA and the NdeI restriction site at position 2844 was removed to create a single NdeI site downstream of the pBAD promoter. The resulting plasmid was named pBAD-HisA_MCSmod. The NdeI/EcoRI fragment of plasmid pKSIC4-HC77623 (U.S. patent application Ser. No. 11/389,948) was inserted into the NdeI/EcoRI site of pBAD-HisA_MCSmod, creating plasmid pSF004_pBAD-KSIC4-HC77623. The HindIII fragment of plasmid pCL 1920 (Lerner and Inouye, *Nucleic Acids Research*, 18:4631 (1990); GENBANK® Accession No. AB236930) comprising the spectinomycin resistance gene (aadA-1) was inserted into pSF004_pBAD-KSI4-HC77623, creating plasmid pLR042. Plasmid pLR186 (FIG. 4; SEQ ID NO: 49) was created from plasmid pLR042 by removing the coding region for the KSIC4-HC77623 fusion peptide and inserting the coding region for fusion peptide IBT139-HC776124 (i.e. a fusion peptide comprising inclusion body tag IBT-139 linked to the HC776124 peptide of interest; see Example 4).

Example 2

Construction of Various Peptides of Interest

Five multi-block hair binding peptides were designed with the following amino acid sequences. Construction of multi-block hair binding peptides have been reported (see co-pending U.S. patent application Ser. Nos. 11/389,948 and 11/074,473). The soluble multi-block peptides (i.e. the "peptides of interest") were used to evaluate the present inclusion body tags. Each of the multi-block hair binding peptides comprises Example 3

Identification of Inclusion Body Tags

Several fusion partner sequences ("inclusion body tags") were evaluated for their ability to drive the resulting fusion peptides (when operably linked to a short, generally soluble peptide of interest) into intracellular insoluble inclusion bodies. Various hair-binding peptide constructs (HC77607, HC77638, HC77643, and HC77681) were cloned into the tag library (parent plasmid pLX121, see sequence below). Expression of the fusion products are driven from a T7 promoter. In *E. coli* BL21-AI, expression of the T7 RNA polymerase gene is under control of the araBAD promoter (i.e. arabinose inducible expression). In addition, HC77638 was also cloned into a tag library composed of the same tags, but different parent plasmid (parent pSF032, see sequence below) that drives expression of the fusion products from a araBAD promoter. The genes encoding the soluble hair binding peptides (e.g., peptides of interest) were cloned downstream of the tag sequences in a batch cloning approach using restriction enzyme sites BamHI at the 5' and AscI at the 3' end.

All constructs in parent plasmid pLX121 were transformed into *E. coli* BL21-AI cells (Invitrogen), constructs in parent plasmid pSF032 were transformed into *E. coli* MG1655 (ATCC 46076™) with a deletion in the endogenous chromosomal copy of the araBAD operon. About 1000 transformants were screened for each library. Positive hits were run on SDS-PAGE gels. To confirm the results, 3 mL growths in LB (plus 100 μg/mL of ampicillin) were inoculated with 30 μL of an overnight culture of the respective constructs. The cultures were grown to OD$_{600}$ of about 0.4 and induced with 0.2% arabinose and grown for 3 hours. To determine soluble versus insoluble cell content, the cells were lysed and soluble and insoluble fractions were run on an SDS-PAGE gel.

Upon analysis of the results it became apparent that for every library that was screened, at least one of four inclusion body tags that were composed of similar sequences was able to drive the fusion proteins into inclusion bodies (Table 2). Not only was a member of this tag family able to drive each tested peptide into insoluble Bs, it was also able to do that in different *E. coli* strains and with different promoters driving the expression.

Construction of Fusion Peptide IBT139.HC776124

The nucleic acid molecule (SEQ ID NO: 22) encoding HC776124 (SEQ ID NOs: 23) was ordered by DNA2.0 (Menlo Park, Calif.) and cloned into restriction sites BamHI (5') and AscI (3') of parent plasmid pLR042, creating plasmid pLR186 (SEQ ID NO: 49). The nucleic acid molecule encoding IBT139 (SEQ ID NO: 20) was cloned into restriction sites

TABLE 2

Summary of results obtained by the several IB tags. Information of the tags is shown in the left half of the table. The right half of the table shows the expression level obtained for each of the HC construct in its respective *E. coli* strain. The value 1 refers to medium expression level, 2 refers to high expression level. nd = not detected in screen.

| Inclusion Body Tag | | Peptide of Interest and Expression System and the Relative Expression Ranking | | | | |
|---|---|---|---|---|---|---|
| Solubility Tag | Amino Acid Sequence (SEQ ID NO:) | HC77607 | HC77638 | HC77638 | HC77643 | HC77681 |
| IBT103 | QQRFQWQFEQQPRGQQRFQ WQFEQQPEGQQRFQWQFEQQ (SEQ ID NO: 15) | 2 | 1 | 2 | 1 | nd |
| IBT136 | QQRFQWQFEQQ (SEQ ID NO: 17) | 1 | nd | nd | nd | nd |
| IBT138 | QQRFQWQFEQQPEGQQRF QWQFEQQ (SEQ ID NO: 19) | 2 | nd | nd | nd | 2 |
| IBT139 | QQRFQWQFEQQPRGQQR FQWQFEQQPRGQQRFQW QFEQQPEGQQRFQWQFEQQ (SEQ ID NO: 21) | 1 | nd | nd | 2 | nd |

Example 4

Use of IBT139 to Drive Additional Peptides of Interest into Inclusion Bodies

To determine whether this family of tags is generally useful in driving proteins into inclusion bodies, the largest member of this family, IBT139, was further evaluated with a protein that has not undergone the screening process with the tag library.

NdeI (5') and BamHI (3'), resulting in a chimeric gene (SEQ ID NO: 24) encoding fusion protein IBT139.HC776124 (SEQ ID NO: 25).

Construct: IBT139.HC776124

The design of peptide HC776124 is provided in Table 3. Peptide HC776124 (a dimer of HC77643) is comprised of several hair binding domains including A09 (SEQ ID NO: 3) and KF11 (SEQ ID NO: 4) (bold). The acid cleavable DP moieties are italicized (Table 3).

TABLE 3

Organization of HC776124.

| Peptide Name | Formula | Amino acid Sequence | Nucleic Acid SEQ ID NO: | Amino Acid SEQ ID NO: |
|---|---|---|---|---|
| HC776124 | GSD(PG-A09-GAG-A09-GGSGPGSGG-KF11-GGG-KF11-GGPKKPGD)2 | GSDPGIPWWNIRAP LNAGAGIPWWNIRA PLNAGGSGPGSGG NTSQLSTGGGNTS QLSTGGPKKPGDP GIPWWNIRAPLNAG AGIPWWNIRAPLNA GGSGPGSGGNTSQ LSTGGGNTSQLSTG GPKKPGD | 22 | 23 |

Strain Growth and IB Analysis.

A 3 mL growth in LB (plus 100 µg/mL of ampicillin) was inoculated with 30 µL of an overnight culture of the respective constructs. The culture was grown to $OD_{600}$ of about 0.4 and induced with 0.2% arabinose and grown for 3 hours. To determine soluble versus insoluble cell content, the cells were lysed and soluble and insoluble fractions were run on an SDS-PAGE gel.

Result:

The fusion protein IBT139.HC776124 was produced in the form of insoluble inclusion bodies.

Example 5

Small Inclusion Body Tag (IBT186) Comprising an Effective Number of Cross-Linkable Cysteines can be Separated from the Cleaved Peptide Mixture by Oxidative Cross-Linking and Precipitation The purpose of this example is to show that a small tag inclusion body tag (e.g. IBT186; SEQ ID NOs: 26 and 27) containing an effective number of cross-linkable cysteine residues (IBT186 contains 4 cysteine residues) can drive both inclusion body formation while being easy to separate using oxidative cross-linking. The example also shows that a small inclusion body tag previously shown to be effective in inducing inclusion body formation can be modified to contain an effective amount of cross-linkable cysteine residues (IBT186 is derived from small tag IBT139 (Examples 3-4) with four cross-linkable cysteines distributed within its sequence) while maintaining its ability to effective drive inclusion body formation. The presence of four cysteines allows simple precipitation of the tag after cleavage of tag and peptide.

Construction, Cloning and Initial Analysis of IBT186.HC776124:

The nucleic acid molecule (SEQ ID NO: 26) encoding IBT186 was synthesized by DNA2.0 (Menlo Park, Calif.) and cloned into restriction sites NdeI (5') and BamHI (3') of plasmid pLR186 (expression driven off pBAD promoter) to make a fusion with the HC776124 construct, creating a chimeric gene (SEQ ID NO: 28) encoding fusion peptide IBT186.HC776124 (SEQ ID NO: 29). The resulting plasmid (pLR238) was transformed into *E. coli* MG1655 (ATCC 46076™) with the araBAD operon deleted.

A 3-mL growth in LB (plus 100 µg/mL of ampicillin) was inoculated with 30 µL of an overnight culture. The culture was grown to $OD_{600}$ of about 0.4 and induced with 0.2% arabinose and grown for 3 hours. To determine soluble versus insoluble cell content, the cells were lysed and soluble and insoluble fractions were run on an SDS-PAGE gel. The fusion protein was produced in the form of insoluble inclusion bodies.

Large Scale Preparation and Isolation of Fusion Protein IBT186.HC776124:

Growth Conditions:

*E. coli* cells were fermented in a 10-L vessel unless otherwise noted. The fermentation proceeded in three stages:

1. Preparation of 125-mL of seed inoculum. Cells containing the construct of interest were inoculated in 125-mL of 2YT seed medium (10 g/L yeast extract, 16 g/L tryptone, 5 g/L NaCl and appropriate antibiotic) and grown for several hours at 37° C.
2. Growth in batch phase. The 125-mL of inoculum was added to 6 L of batch medium (9 g/L $KH_2PO_4$, 4 g/L $(NH_4)_2HPO_4$ 1.2 g/L $MgSO_4.7H_2O$, 1.7 g/L citric acid, 5 g/L yeast extract, 0.1 mL/L Biospumex 153K antifoam, 4.5 mg/L Thiamine.HCl, 23 g/L glucose, 10 mL/L trace elements, 50 mg/L uracil, appropriate antibiotic, pH 6.7) at 37° C.
3. Growth in fed batch phase. After about 12 hours of growth in the batch phase, the fed-batch phase was initiated. Fed-batch medium (2 g/L $MgSO_4.7H_2O$, 4 g/L $(NH_4)_2HPO_4$ 9 g/L $KH_2PO_4$, 1-2 g/min Glucose) was added at a constant rate to the reactor for about 15 hours at 37° C. 4 hours before the end of the fed-batch phase the cells were induced to express the POI by adding 2 g/L L-arabinose.

Fermentation Broth Processing, Oxidative Cross-Linking and Analysis

The whole fermentation broth was passed through an APV model 2000 Gaulin type homogenizer at 12,000 psi (82,700 kPa) for three passes. The broth was cooled to below 5° C. prior to each homogenization. The homogenized broth was immediately processed through a Westfalia WHISPERFUGE™ (Westfalia Separator Inc., Northvale, N.J.) stacked disc centrifuge at 600 mL/min and 12,000 relative centrifugal force (RCF) to separate inclusion bodies from suspended cell debris and dissolved impurities. The recovered paste was re-suspended at 15 g/L (dry basis) in water and the pH adjusted to about 10.0 using NaOH. The suspension was passed through the APV 2000 Gaulin type homogenizer at 12,000 psi (82,700 kPa) for a single pass to provide rigorous mixing. The homogenized pH 10 suspension was immediately processed in a Westfalia WHISPERFUGE™ stacked disc centrifuge at 600 mL/min and 12,000 RCF to separate the washed Inclusion bodies from suspended cell debris and dissolved impurities. The recovered paste was resuspended at 15 gm/L (dry basis) in pure water. The suspension was passed through the APV 2000 Gaulin type homogenizer at 12,000 psi (82,700 kPa) for a single pass to provide rigorous washing. The homogenized suspension was immediately processed in a Westfalia WHISPERFUGE™ stacked disc centrifuge at 600 mL/min and 12,000 RCF to separate the washed Inclusion bodies from residual suspended cell debris and NaOH. The recovered paste was resuspended in pure water at 25 gm/L (dry basis) and the pH or the mixture adjusted to 2.2 using HCl. The acidified suspension was heated to 70° C. for 14 hours to complete cleavage of the DP site separating the fusion peptide from the product peptide. The product was pH neutralized (note: the pH used may vary depending upon the solubility of the peptide being recovered) and cooled to ~5° C. and held for 12 hours. During this step the suspension was held in a 500-mL or 1-L bottle no more than ¾ full to ensure adequate presence of oxygen to ensure cysteine cross linking through disulfide formation. The mixture was then centrifuged at 9000 RCF for 30 minutes and the supernatant decanted for HPLC analysis.

HPLC Analysis

The supernatant was filtered with a 0.2 micron membrane. The filtered product was loaded in a 22×250 mm reverse phase chromatography column GraceVydac® (218TP1022) containing 10 micron C18 media which was preconditioned with 10% acetonitrile (ACN), 90% water with 0.1% v/v trifluoroacetic acid (TFA). The product was recovered in a purified state by eluting the column with a gradient of water and acetonitrile (ACN) ramping from 10% to 25% acetonitrile (ACN) in water with TFA at 0.1% v/v at room temperature and approximately 10 mL/min. Spectrophotometric detection at 220 nm was used to monitor and track elution of the product peptide.

Oxidative Cross-Linking to Separate the IBT from the Peptide of Interest

The protein was purified as described above. After the acid cleavage and pH neutralization, the mixture was stored at ~5° C. for about 6 hours to allow the cysteines to form cross-linked bonds. Ambient air exposure provided oxygen to cause cysteine cross-linking. The mixture was centrifuged at 9000 RCF for 30 minutes and the precipitated inclusion body tag was separated from the soluble peptide of interest.

Results after Oxidative Cross-Linking:

SDS-PAGE gel analysis of both the precipitate paste and the remaining soluble fraction showed the presence of IBT186 in the insoluble paste and HC776124 remaining in the soluble fraction. This was further confirmed by HPLC, which showed only the presence of HC776124 in the soluble fraction (see Table 4).

Example 6

Introduction of Multiple Cysteines to the Terminus of an Inclusion Body Tag Promotes Oxidative Cross-Linking while Retaining the Ability to Effectively Drive Fusion Peptides into Inclusion Bodies The purpose of this example is to show that the addition of at least one cross-linkable cysteine motif comprising effective number of cysteine residues to the terminus of an inclusion body tag creates a cross-linkable IBT, even when the cysteines are spaced closely together. A cross-linkable cysteine motif was added to an inclusion body tag normally devoid of cross-linkable cysteine residues (i.e. IBT139; SEQ ID NO: 21), creating cysteine modified tag "IBT139.CCPGCC" (SEQ ID NOs: 30-31). The addition of the motif did not alter the IBT's ability to drive inclusion body formation while the modification facilitated simple separation of the tag using oxidative cross-linking. The results of the cross-linking experiments are summarized in Table 4.

Cloning and Initial Analysis of Fusion Peptide IBT139.CCPGCC. HC776124:

To facilitate crosslinking, the tetracysteine tag CCPGCC (SEQ ID NOs: 32-33) was introduced at the end of the inclusion body promoting sequence IBT139 (SEQ ID NO: 21) which does not naturally contain cysteine residues, resulting in IBT139.CCPGCC (SEQ ID NOs: 30 and 31). The CCPGCC tetracysteine tag is the LUMIO™ biarsenical dye binding motif. The LUMIO™ Green detection kit was obtained from Invitrogen (Invitrogen, Carlsbad, Calif.).

The oligonucleotides encoding the tetracysteine tag were synthesized by Sigma Genosys. The top strand oligo 5'-GATCTTGCTGTCCGGGCTGTTGCG-3' (SEQ ID NO: 34) and the bottom strand oligo 5'-GATCCGCAACAGC-CCGGACAGCAA-3' (SEQ ID NO: 35) were annealed with a Bg/II overhang at the 5' end and a BamHI overhang at the 3' end. The annealed double stranded fragment was cloned into the BamHI site of a peptide expression plasmid pLR186, creating plasmid pLR199. Plasmid pLR199 contained the peptide of interest HC776124 fused to the inclusion body promoting sequence IBT139 expressed by the $P_{BAD}$ promoter. The resulting clone contained the tetracysteine tag CCPGCC (SEQ ID NO: 33) inserted after the inclusion body promoting sequence and before the acid cleavage site. The nucleic acid molecule encoding fusion peptide IBT139.CCPGCC.HC776124 is provided as SEQ ID NO:36 and the resulting fusion peptide is provided as SEQ ID NO: 37.

Introduction of the tetracysteine moiety did not affect expression or localization of the peptides by running an equivalent number of cells on a protein gel and seeing same levels of expression. The overexpressed protein was shown to be in the form of inclusion bodies by treating the cells with CELLYTIC™ Express and verifying that they were in the insoluble fraction. The inclusion body promoting sequence IBT139 with addition of the cross-linkable CCPGCC tag did not alter the inclusion body tag's ability to form inclusion bodies (Table 4).

Production of Product Protein:

The protein was produced purified as described in Example 5. After the acid cleavage and pH neutralization, the mixture was stored at ~5° C. for at least 6 hours to allow the cysteines to form cross-linked bonds. Ambient air exposure provided oxygen to cause cysteine cross-linking. The mixture was centrifuged at 9000 RCF for 30 minutes and the precipitated tag was separated from the soluble peptide.

Results:

SDS-PAGE gel analysis of both the precipitated paste and the remaining soluble fraction showed the presence of the inclusion body tag (IBT139.CCPGCC) in the insoluble paste and the peptide of interest (HC776124) remaining in the soluble fraction. This was further confirmed by HPLC analysis, which showed only the presence of HC776124 in the soluble fraction. The results of the cross-linking experiments are summarized in Table 4.

TABLE 4

Summary of Cross-Linking Results

| Construct Evaluated | IBT Induces IB Formation in Cell | Number of Cysteines in the inclusion body tag | Separation via Oxidative Cross-linking and Centrifugation |
|---|---|---|---|
| IBT139.HC776124 | Yes | None | No |
| IBT186.HC776124 | Yes | 4 | Yes |
| IBT139.CCPGCC.HC776124 | Yes | 4 | Yes |

Example 7

Preparation of Additional Inclusion Body Tags

Additional inclusion body tags were designed based on the IBT136. The overall scheme to test fusion partner sequences (IBT182, IBT183, IBT184, IBT185, IBT186 (also evaluated with HC776124 as described above), IBT187a, and IBT187b) was to design DNA oligonucleotides that when annealed generate the stick-ends required for directional cloning of the fusion partner in-frame with the test expression peptide, HC77643.

Various combinations of synthetic, complementary oligonucleotides were assembled having *E. coli* codon biased codons. The oligonucleotide pairs were designed to test various sequence modification based on the sequence of IBT136 (Table 5).

Generation of Putative IBTs

An example of the methodology used to generate, test putative fusion partners follows. A nucleic acid molecule (SEQ ID NO: 38) encoding the amino acid sequence of IBT182 (QQHFHWHFQQQPRGQQHFHWH-FQQQPEGQQHFHWHFQQQ; SEQ ID NO: 39) was assembled from two complementary synthetic *E. coli* codon biased oligonucleotides (Sigma-Genosys). Overhangs were included in each oligonucleotide as to generate cohesive end compatible with the restriction sites NdeI and BamHI.

The oligonucleotides were annealed by combining 100 pmol of each oligonucleotide in deionized water into one tube and heated in a water bath set at 99° C. for 10 minutes after which the water bath was turned off. The oligonucleotides were allowed to anneal slowly until the water bath reached room temperature (20-25° C.). The annealed oligonucleotides were diluted in 100 μL water prior to ligation into the test vector. The vector pSF043 (SEQ ID NO: 50) comprises the HC77643 peptide of interest linked to the KSI(C4) (SEQ ID NOs: 52-53) inclusion body tag, resulting in fusion peptide KSI(C4).HC77643 (SEQ ID NOs: 54-55). The vector was digested in Buffer 2 (New England Biolabs, Beverly Mass.) comprising 10 mM Tris-HCl, 10 mM MgCl$_2$, 50 mM NaCl, 1 mM dithiothreitol (DTT); pH ~7.9) with the NdeI and BamHI restriction enzymes to release a 381 by fragment corresponding to IBT KSI(C4).

The NdeI-BamHI fragments from the digested plasmid were separated by agarose gel electrophoresis and the vector was purified from the gel by using Qiagen QiAquick® Gel Extraction Kit (QIAGEN Valencia, Calif.; cat# 28704).

The diluted and annealed oligonucleotides (approximately 0.2 pmol) were ligated with T4 DNA Ligase (New England Biolabs Beverly, Mass.; catalog #M0202) to NdeI-BamHI digested, gel purified, plasmid (approximately 50 ng) at 12° C. for 18 hours. DNA sequence analysis confirmed the expected plasmid sequence.

The expression vector comprising the chimeric gene encoding IBT182 fused to the HC77643 peptide of interest was transformed into the arabinose inducible expression strain *E. coli* BL21-A1 (Invitrogen). To produce the recombinant protein, 3 mL of LB-ampicillin broth (10 g/L bacto-tryptone, 5 g/L bacto-yeast extract, 10 g/L NaCl, 100 mg/L ampicillin; pH 7.0) was inoculated with one colony of the transformed bacteria and the culture was shaken at 37° C. until the OD$_{600}$ reached 0.6. Expression was induced by adding 0.03 mL of 20% L-arabinose (final concentration 0.2%, Sigma-Aldrich, St. Louis, Mo.) to the culture and shaking was continued for another 3 hours. For whole cell analysis, 0.1 OD$_{600}$ mL of cells were collected, pelleted, and 0.06 mL SDS PAGE sample buffer (1×LDS Sample Buffer (Invitrogen cat# NP0007), 6 M urea, 100 mM DTT) was added directly to the whole cells. The samples were heated at 99° C. for 10 minutes to solubilize the proteins. The solubilized proteins were then loaded onto 4-12% gradient MES NUPAGE® gels (NUPAGE® gels cat #NP0322, MES Buffer cat# NP0002; Invitrogen) and visualized with a COOMASSIE® G-250 stain (SimplyBlue™ SafeStain; Invitrogen; cat# LC6060) for inclusion body formation.

The above cloning and expression scheme was repeated for IBT183, IBT184, IBT185, IBT186, IBT187a, and IBT187b. IBT187b was generated as a cloning artifact from IBT187a. The presence or absence of the fusion peptide in the form of inclusion bodies was determined. The sequence of the various inclusion body tags as well as their ability to drive inclusion body formation of a normally soluble peptide of interest (HC77643) was determined and reported in Table 5.

Table 5: Summary of the results obtained by additional IBTs derived from the IBT136. The presence or absence of inclusion body formation was determined.

TABLE 5

| Solubility Tag | Amino Acid Sequence (SEQ ID NO.) | Inclusion Body Formation with HC77643 |
|---|---|---|
| IBT182 | QQHFHWHFQQQPRGQQHFHWHFQQQPEGQ QHFHWHFQQQ (SEQ ID NO: 39) | Yes |
| IBT183 | QQHFHWHFQQQPRGQQKFKWKFQQQPEGQ QHFHWHFQQQ (SEQ ID NO: 41) | Yes |
| IBT184 | QQKFHWHFQQQPRGQQKFHWHFQQQPEGQ QKFHWHFQQQ (SEQ ID NO: 43) | Yes |
| IBT185 | MASPCGQQRFQWQFEQQPCGQQRFQWQFE QQPCGQQRFQWQFEQQPCG (SEQ ID NO: 45) | Yes |
| IBT186 | MASCGQQRFQWQFEQQPRCGQQRFQWQFE QQPECGQQRFQWQFEQQPC (SEQ ID NO: 27) | Yes |
| IBT187a | QQKFKWKFQQQPRGQQKFKWKFQQQPEGQ QKFKWKFQQQ (SEQ ID NO: 47) | Yes |
| IBT187b | QQKFKWKFQQQPRGQQKFKWKFQQQPRGQ QKFKWKFQQQPEGQQKFKWKFQKQ (SEQ ID NO: 49) | Yes |

What is claimed is:

1. A nucleic acid molecule encoding a fusion peptide comprising an inclusion body tag operably linked to at least one peptide of interest; wherein the inclusion body tag comprises the structure:

SEQ ID NO: 58-Spacer-[[SEQ ID NO: 58]-[Spacer]$_m$]$_n$ wherein

SEQ ID NO: 58 is Gln-Gln-Xaa1-Phe-Xaa2-Trp-Xaa3-Phe-Xaa4-Xaa5-Gln;

Xaa1=Arg, His, or Lys;
Xaa2=Gln, His, or Lys;
Xaa3=Gln, His, or Lys;
Xaa4=Glu or Gln;
Xaa5=Gln or Lys;
n=1 to 10;
m=n−1; and
Spacer=is a peptide comprising the amino acids selected from the group consisting of proline, arginine, glycine, glutamic acid, and cysteine.

2. An expression cassette comprising the nucleic acid molecule of claim 1.

3. A vector comprising the expression cassette of claim 2.

4. A microbial host cell comprising the vector of claim 3.

5. The microbial host cell of claim 4, wherein the host cell is selected from the group consisting of *Aspergillus, Trichoderma, Saccharomyces, Pichia, Yarrowia, Candida, Hansenula, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus.*

6. A method for expressing a peptide in insoluble form comprising:

a) synthesizing an expressible genetic construct encoding a fusion peptide comprising a first portion encoding an inclusion body tag operably linked to a second portion encoding a peptide of interest;

b) transforming an expression host cell with the genetic construct of (a);

c) growing the transformed host cell of (b) under conditions wherein the expressible genetic construct is expressed and the encoded fusion peptide is produced in an insoluble form; and d) recovering said fusion peptide in said insoluble form; wherein the inclusion body tag comprises the structure:
SEQ ID NO: 58-Spacer-[[SEQ ID NO: 58]-[Spacer]$_m$]$_n$
wherein SEQ ID NO: 58 is
Gln-Gln-Xaa1-Phe-Xaa2-Trp-Xaa3-Phe-Xaa4-Xaa5-Gln;

Xaa1=Arg, His, or Lys;
Xaa2=Gln, His, or Lys;
Xaa3=Gln, His, or Lys;
Xaa4=Glu or Gln;
Xaa5=Gln or Lys;
n=1 to 10;
m=n−1; and
Spacer=is a peptide comprising the amino acids selected from the group consisting of proline, arginine, glycine, glutamic acid, and cysteine.

7. A method for the production of a peptide of interest comprising:
   a) synthesizing a genetic construct encoding a fusion peptide comprising a first portion encoding an inclusion body tag operably linked to a second portion encoding at least one peptide of interest; wherein said first portion and said second portion are separated by at least one cleavable peptide linker;
   b) transforming an expression host cell with the genetic construct of (a);
   c) growing the transformed host cell of (b) under conditions wherein the genetic construct is expressed and the encoded fusion peptide is produced in an insoluble form;
   d) recovering the fusion peptide in said insoluble form;
   e) cleaving said fusion peptide said at least one cleavable peptide linker whereby said first portion of the fusion peptide is no longer fused to said second portion; and
   f) recovering said peptide of interest; wherein the inclusion body tag comprises the structure:
SEQ ID NO: 58-Spacer-[[SEQ ID NO: 58]-[Spacer]$_m$]$_n$
wherein SEQ ID NO: 58 is
Gln-Gln-Xaa1-Phe-Xaa2-Trp-Xaa3-Phe-Xaa4-Xaa5-Gln;

Xaa1=Arg, His, or Lys;
Xaa2=Gln, His, or Lys;
Xaa3=Gln, His, or Lys;
Xaa4=Glu or Gln;
Xaa5=Gln or Lys;
n=1 to 10;
m=n−1; and
Spacer=is a peptide comprising the amino acids selected from the group consisting of proline, arginine, glycine, glutamic acid, and cysteine.

8. The method according to claim 7 wherein the cleavable peptide linker is cleaved using chemical hydrolysis, enzymatic hydrolysis, or combinations thereof.

9. The method according to claim 7 wherein the peptide of interest is selected from the group consisting of a polymer-binding peptide, a hair-binding peptide, a nail-binding peptide, a skin-binding peptide, a clay-binding peptide, a pigment-binding peptide, a cellulose-binding peptide, and an antimicrobial peptide.

10. The method according to claim 9 wherein the hair-binding peptide is selected from the group consisting of SEQ ID NOs: 3, 4, 5, 7, 9, 11, 13, 23, and 59-147.

11. The method according to claim 9 wherein the skin-binding peptide is selected from the group consisting of SEQ ID NOs: 148 to 155.

12. The method according to claim 9 wherein the nail-binding peptide is selected from the group consisting of SEQ ID NOs: 156 to 157.

13. The method according to claim 9 wherein the polymer binding peptide is selected from the group consisting of SEQ ID NOs: 218 to 244.

14. The method according to claim 9 wherein the clay-binding peptide is selected from the group consisting of SEQ ID NOs: 245 to 260.

15. The method according to claim 9 wherein the antimicrobial peptide is selected from the group consisting of SEQ ID NOs: 158 to 186.

* * * * *